US012703752B2

(12) United States Patent
Tietz et al.

(10) Patent No.: US 12,703,752 B2
(45) Date of Patent: Aug. 11, 2026

(54) MULTISPECIFIC ANTIBODIES HAVING SPECIFICITY FOR IL-4R AND IL-31, ENCODING NUCLEIC ACIDS THEREOF AND METHODS OF TREATING

(71) Applicant: CILAG GMBH INTERNATIONAL, Zug (CH)

(72) Inventors: Julia Tietz, Schlieren (CH); Tea Gunde, Zurich (CH); Maria Johansson, Denges (CH); Stefan Warmuth, Au (CH); Alexandre Simonin, Rosenau (FR); Christian Hess, Zurich (CH); Noriko Shiraishi, Tokyo (JP); Yoshio Arakawa, Tokyo (JP); Yoshihide Miyake, Tokyo (JP)

(73) Assignee: CILAG GMBH INTERNATIONAL, Zug (CH)

( * ) Notice: Subject to any disclaimer, the term of this patent is extended or adjusted under 35 U.S.C. 154(b) by 16 days.

(21) Appl. No.: 18/258,858

(22) PCT Filed: Dec. 23, 2021

(86) PCT No.: PCT/EP2021/087561
§ 371 (c)(1),
(2) Date: Jun. 22, 2023

(87) PCT Pub. No.: WO2022/136669
PCT Pub. Date: Jun. 30, 2022

(65) Prior Publication Data

US 2025/0282879 A1 Sep. 11, 2025

(30) Foreign Application Priority Data

Dec. 23, 2020 (EP) .................................... 20216957

(51) Int. Cl.
*C07K 16/28* (2006.01)
*C07K 16/24* (2006.01)

(52) U.S. Cl.
CPC ........ *C07K 16/2866* (2013.01); *C07K 16/244* (2013.01); *C07K 2317/31* (2013.01); *C07K 2317/33* (2013.01); *C07K 2317/622* (2013.01); *C07K 2317/76* (2013.01); *C07K 2317/92* (2013.01)

(58) Field of Classification Search
CPC .............. C07K 16/2866; C07K 16/244; C07K 2317/31; C07K 2317/33; C07K 2317/622; C07K 2317/76; C07K 2317/92
See application file for complete search history.

(56) References Cited

U.S. PATENT DOCUMENTS 4,458,066 A 7/1984 Caruthers et al.
4,881,175 A 11/1989 Ladner
5,013,653 A 5/1991 Huston et al.
5,091,513 A 2/1992 Huston et al.
5,132,405 A 7/1992 Huston et al.
5,258,498 A 11/1993 Huston et al.
5,260,203 A 11/1993 Ladner et al.
5,455,030 A 10/1995 Ladner et al.
5,476,786 A 12/1995 Huston
5,482,858 A 1/1996 Huston et al.
5,766,886 A 6/1998 Studnicka et al.
2024/0043547 A1 2/2024 Tietz et al.

FOREIGN PATENT DOCUMENTS

EP 4019090 A1 6/2022
EP 4019546 A1 6/2022
WO 1999057150 A2 11/1999
WO 2004042072 A2 5/2004
WO 2004092219 A2 10/2004
WO 2008/028192 A2 3/2008
WO 2014039461 A1 3/2014
WO 2019057787 A1 3/2019
WO 2020/135471 A1 7/2020

OTHER PUBLICATIONS

Agrawal et al., "Role of Periostin, Feno, IL-13, Lebrikzumab, Other IL-13 Antagonist and Dual IL-4/IL-13 Antagonist in Asthma", Expert Opinion on Biological Therapy, vol. 14, No. 2, pp. 165-181, 2014.
Bieber, Thomas "Atopic Dermatitis: an Expanding Therapeutic Pipeline for a Complex Disease", Nature review Drug Discovery, vol. 21, pp. 21-40, 2021.
Bodoor et al., "IL-33/13 Axis and IL-4/31 Axis Play Distinct Roles in Inflammatory Process and Itch in Psoriasis and Atopic Dermatitis", Clinical, Cosmetic and Investigational Dermatology, vol. 13, pp. 419-424, 2020.
Brinkmann et al., "The Making of Bispecific Antibodies", MABS, vol. 9, No. 2, pp. 182-212, 2017.
Furue et al., "Pathogenesis of Atopic Dermatitis: Current Paradigm", Iranian Journal of Immunology, vol. 16, No. 2, pp. 97-107, Jun. 2019.
Godar et al., "A Bispecific Antibody Strategy to Target Multiple Type 2 Cytokines in Asthma", Journal of Allergy and Clinical Immunology, vol. 142, No. 4, pp. 1185-1193.e4, Oct. 2018.

(Continued)

*Primary Examiner* — Robert S Landsman
(74) *Attorney, Agent, or Firm* — Troutman Pepper Locke LLP

(57) ABSTRACT

The present invention relates to a multispecific antibody comprising one or two binding domains, which specifically bind to IL-4R (IL4R-BDs), and one or two binding domains, which specifically bind to IL-31 (IL31-BDs), wherein the multispecific antibody comprises an immunoglobulin Fc region. The present invention further relates to nucleic acids encoding said multispecific antibody, vector(s) comprising said nucleic acids, host cell(s) comprising said nucleic acids or said vector(s), and a method of producing said multispecific antibody. Additionally, the present invention relates to pharmaceutical compositions comprising said multispecific antibody and methods of use thereof.

36 Claims, 13 Drawing Sheets

Specification includes a Sequence Listing.

(56) References Cited

OTHER PUBLICATIONS

Katoh, Norito "Emerging Treatments for Atopic Dermatitis", The Journal of Dermatology, vol. 48, pp. 152-157, 2020.
Litman, Thomas "Personalized Medicine-concepts, Technologies, and Applications in Inflammatory Skin Diseases", APMIS, vol. 127, pp. 386-424, 2019.
Nie et al., "Biology Drives the Discovery of Bispecific Antibodies as Innovative Therapeutics", Antibody Therapeutics, vol. 3, No. 1, pp. 18-62, 2020.
Nygaard et al., "Emerging Treatment Options in Atopic Dermatitis: Systemic Therapies", Dermatology, vol. 233, pp. 344-357, 2017.
Oetjen et al., "Sensory Neurons Co-opt Classical Immune Signaling Pathways to Mediate Chronic Itch", Cell, vol. 171, pp. 217-228.e13, pp. Sep. 21, 2017.
O'Shea et al., "Chapter 9—Cytokines and Cytokine Receptors", Clinical Immunology, pp. 127-155.e1, 2019.
Rossolini et al., "Use of Deoxyinosine-Containing Primers Vs. Degenerate Primers for Polymerase Chain Reaction Based on Ambiguous Sequence Information," Mol. Cell Probes (Apr. 1994) vol. 8, Issue 2, pp. 91-98.
Ruzicka et al., "Anti-Interleukin-31 Receptor A Antibody for Atopic Dermatitis," N. Engl. J. Med. (Mar. 2, 2017) vol. 376 (9), pp. 826-835.
Scharf et al., "Heat Stress Promoters and Transcription Factors," Results Probl. Cell Differ. (1994) vol. 20, pp. 125-162.
Shields et al., "High Resolution Mapping of the Binding Site on Human IgG1 for FcyRI, FcyRII, FcyRIII, and FcRn and Design of IgG1 Variants with Improved Binding to the FcyR," J. Biol. Chem (2001) vol. 9, No. 2, pp. 6591-6604.
Smith, "Viral Vectors in Gene Therapy," Annu. Rev. Microbiol. (1995) vol. 49, pp. 807+. (17 pgs.).
Spiess et al., "Development of a Human IgG4 Bispecific Antibody for Dual Targeting of Interleukin-4 (IL-4) and Interleukin-13 (IL-13) Cytokines," J. Biol. Chem. (Sep. 13, 2013) vol. 288, No. 37, pp. 26583-26593.
Suresh et al., "[17] Bispecific Monoclonal Antibodies from Hybrid Hybridomas," Methods Enzymol. (1986) vol. 121, pp. 210-228.
Verhoeyen et al., "Reshaping Human Antibodies: Grafting an Antilysozyme Activity," Science (Mar. 25, 1988) vol. 239, Issue 4847, pp. 1534-1536.
Wong et al., "The Dye SYPRO Orange Binds to Amylin Amyloid Fibrils but Not Pre-Fibrilar Intermediates," Protein Science (2016) vol. 25, pp. 1834-1840.
Xia et al., "Recent Developments in CCR2 Antagonists," Expert Opinion on Therapeutic Patents (2009) vol. 19(3), pp. 295-303.
Zhu et al., "Tumor Localization and Therapeutic Potential of an Antitumor-Anti-CD3 Heteroconjugate Antibody in Human Renal Cell Carcinoma Xenograft Models," Cancer Lett. (Oct. 28, 1994) vol. 86, Issue 1, pp. 127-134.
Al-Lazikani et al., "Standard Conformations for the Canonical Structures of Immunoglobulins," J. Mol. Biol. (1997) vol. 273, pp. 927-948.
Bagci et al., "IL-31: A New Key Player in Dermatology and Beyond," J. Allergy Clin. Immunol. (Mar. 2018) vol. 141, No. 3, pp. 858-866.
Batzer et al., "Enhanced Evolutionary PCR Using Oligonucleotides with Inosine at the 3'-Terminus," Nucleic Acids Res. (1991) vol. 19, p. 5081.
Beaucage et al., "Deoxynucleoside Phosphoramidites - A New Class of Key Intermediates for Deoxypolynucleotide Synthesis," Tetra. Lett. (1981) vol. 22, No. 20, pp. 1859-1862.
Bittner et al., "[33] Expression and Secretion Vectors for Yeast," Meth. Enzymol. (1987) vol. 153, pp. 516-544.
Brennan et al., "Preparation of Bispecific Antibodies by Chemical Recombination of Monoclonal Immunoglobulin G1 Fragments," Science (Jul. 5, 1985) vol. 229, Issue 4708, pp. 81-83.
Brown et al., "[8] Chemical Synthesis and Cloning of a Tyrosine tRNA Gene," Meth. Enzymol. (1979) vol. 68, pp. 109-151.
Capel et al., "Heterogeneity of Human IgG Fc Receptors," Immunomethods (1994) vol. 4, pp. 25-34.
Chames et al., "Antibody Engineering and Its Applications in Tumor Targeting and Intracellular Immunization," FEMS Microbiol. Letters (Aug. 2000) vol. 189, Issue 1, pp. 1-8.
Daeron, "Fc Receptor Biology," Annu. Rev. Immunol. (1997) vol. 15, pp. 203-234.
De Haas et al., "Fc Gamma Receptors of Phagocytes," J. Lab. Clin. Med (Oct. 1995) vol. 126(4), pp. 330-341.
Dillon et al., "Interleukin 31, A Cytokine Produced by Activated T Cells, Induces Dermatitis in Mice," Nature Immunol. (Jul. 2004) vol. 5, No. 7, pp. 752-760.
Eckert et al., "DNA Polymerase Fidelity and the Polymerase Chain Reaction" PCR Methods and Applications (1991) 1:17-24.
Egan et al., "Novel Multispecific Heterodimeric Antibody Format Allowing Modular Assembly of Variable Domain Fragments," MABS (2017) vol. 9, No. 1, pp. 68-84.
Egeberg et al., "Anti-Interleukin-31 Receptor A Antibody for Atopic Dermatitis," N. Engl. J. Med. (May 25, 2017) vol. 376(21), pp. 2092-2093.
Elliott et al., "Intercellular Trafficking and Protein Delivery by a Herpesvirus Structural Protein," Cell (Jan. 24, 1997) vol. 88, Issue 2, pp. 223-233.
Fischer et al., "Bispecific Antibodies: Molecules That Enable Novel Therapeutic Strategies," Pathobiology (2007) vol. 74, pp. 3-14.
Ghetie et al., "FcRn: the MHC Class I-Related Receptor that is More than an IgG Transporter," Immunol. Today (Dec. 1997) vol. 18, No. 12, pp. 592-598.
Ghetie et al., "Increasing the Serum Persistence of an IgG Fragment by Random Mutagenesis," Nature Biotechnology (Jul. 1997) vol. 15(7), pp. 637-640.
Glennie et al., "Preparation and Performance of Bispecific F(ab'gamma)2 Antibody Containing Thioether-Linked Fab'gamma Fragments," J. Immunol. (Oct. 1987) vol. 139, Issue 7, pp. 2367-2375.
Guyer et al., "Immunoglobulin Binding by Mouse Intestinal Epithelial Cell Receptors," J. Immunol. (Aug. 1976) vol. 117, No. 2, pp. 587-593.
Harrington et al., "Formation of De Novo Centromeres and Construction of First-Generation Human Artificial Microchromosomes," Nat Genet. (Apr. 1997) vol. 15, pp. 345-355.
Hinton et al., "Engineered Human IgG Antibodies with Longer Serum Half-Lives in Primates," J. Biol. Chem. (Feb. 2004) vol. 279, No. 8, pp. 6213-6216.
Honegger et al., "Yet Another Numbering Scheme for Immunoglobulin Variable Domains: An Automatic Modeling and Analysis Tool," J. Mol. Biol. (2001) vol. 309, pp. 657-670.
Hornig et al., "Production of Bispecific Antibodies: Diabodies and Tandem scFv," Methods Mol. Biol. (2012) vol. 907, pp. 713-727.
International Search Report and Written Opinion for International PCT Application No. PCT/EP2021/087561 dated Apr. 5, 2022.
Karpovsky et al., "Production of Target-Specific Effector Cells Using Hetero-Cross-Linked Aggregates Containing Anti-Target Cell and Anti-Fc Gamma Receptor Antibodies," J. Exp. Med. (1984) 160(6), pp. 1686-1701.
Kim et al., "Localization of the Site of the Murine IgG1 Molecule That is Involved in Binding to the Murine Intestinal Fc Receptor," Eur. J. Immunol. (Oct. 1994) vol. 24(10), pp. 2429-2434.
Knappik et al., "Fully Synthetic Human Combinatorial Antibody Libraries (HuCAL) Based on Modular Consensus Frameworks and CDRs Randomized with Trinucleotides," J. Mol. Biol. (2000) vol. 296, pp. 57-86.
Kruif et al., "Generation of Stable Cell Clones Expressing Mixtures of Human Antibodies," Biotechnol. Bioeng. (Aug. 2010) vol. 106, No. 5, pp. 741-750.
Kwiatkowski et al., "Dinucleotide Repeat Polymorphism at the ABL Locus (9q34)," Nucleic Acids Res. (Feb. 25, 1991) vol. 19(4), p. 967.
Labrijn et al., "Efficient Generation of Stable Bispecific IgG1 by Controlled Fab-arm Exchange," Proc. Natl. Acad. Sci. USA (Mar. 13, 2013) vol. 110, No. 13, pp. 5145-5150.

(56) References Cited

OTHER PUBLICATIONS

Lefranc, "The IMGT Unique Numbering for Immunoglobulins, T-Cell Receptors, and Ig-Like Domains," The Immunologist (1999) vol. 7/4, pp. 132-136.
Lefranc et al., "IMGT Unique Numbering for Immunoglobulin and T Cell Receptor Variable Domains and Ig Superfamily V-Like Domains," Dev. Comp. Immunol. (2003) vol. 27(1), pp. 55-77.
Lewis et al., "Interleukin (IL) 31 Induces in Cynomolgus Monkeys a Rapid and Intense Itch Response that can be Inhibited by an IL-31 Neutralizing Antibody," J. Eur. Acad. of Dermatol. Venereol. (Jan. 2017) vol. 31, Issue 1, pp. 142-150.
Lui et al., "Heteroantibody Duplexes Target Cells for Lysis by Cytotoxic T Lymphocytes," Proc. Natl. Acad. Sci. USA (Dec. 1985) vol. 82, pp. 8648-8652.
Lundstrom, "Viral Vectors in Gene Therapy," Diseases (2018) 6, 42, 20 pgs.
Morrison et al., "Chimeric Human Antibody Molecules: Mouse Antigen-Binding Domains with Human Constant Region Domains," Proc. Natl. Acad. Sci. USA (No. 1984) vol. 81, pp. 6851-6855.
Morrison et al., "Genetically Engineered Antibody Molecules," Adv. Immunol. (1989) vol. 44, pp. 65-92.
Narang et al., "[6] Improved Phosphotriester Method for the Synthesis of Gene Fragments," Meth. Enzymol. (1979) vol. 68, pp. 90-98.
Niesen et al., "The Use of Differential Scanning Fluorimetry to Detect Ligand Interactions that Promote Protein Stability," Nature Protocols (2007) vol. 2 No. 9, pp. 2212-2221.
Ohtsuka et al., "An Alternative Approach to Deoxyoligonucleotides as Hybridization Probes by Insertion of Deoxyinosine at Ambiguous Codon Positions," J. Biol. Chem. (Mar. 10, 1985) vol. 260, Issue 5, pp. 2605-2608.
Padlan, "A Possible Procedure for Reducing the Immunogenicity of Antibody Variable Domains While Preserving Their Ligand-Binding Properties," Molec. Immun. (1991) vol. 28, No. 4/5, pp. 489-498.
Padlan, "Anatomy of the Antibody Molecule," Molec. Immun. (Feb. 1994) vol. 31, Issue 3, pp. 169-217.
Paulus, "Preparation and Biomedical Applications of Bispecific Antibodies," Behring Inst. Mitt. (Dec. 1985) No. 78, pp. 118-132.
Queen et al., "Cell-Type Specific Regulation of a K Immunoglobulin Gene by Promoter and Enhancer Elements," Immunol. Rev. (Apr. 28, 1986) No. 89, pp. 49-68.
Ravetch et al., "Fc Receptors," Annu. Rev. Immunol. (1991) vol. 9, pp. 457-492.
Reddel et al., "Transformation of Human Bronchial Epithelial Cells by Infection with SV40 or Adenovirus-12 SV40 Hybrid Virus, or Transfection via Strontium Phosphate Coprecipitation with a Plasmid Containing SV40 Early Region Genes," Cancer Research (Apr. 1988) vol. 48(7), pp. 1904-1909.
Ridgway et al., "'Knobs-into-Holes' Engineering of Antibody CH3 Domains for Heavy Chain Heterodimerization," Protein Eng. (Jul. 1996) vol. 9, Issue 7, pp. 617-621.
Rosenfeld et al., "In Vivo Transfer of the Human Cystic Fibrosis Transmembrane Conductase Regulator Gene to the Airway Epithelium," Cell (Jan. 10, 1992) vol. 68, No. 1, pp. 143-155.

Figure 1:
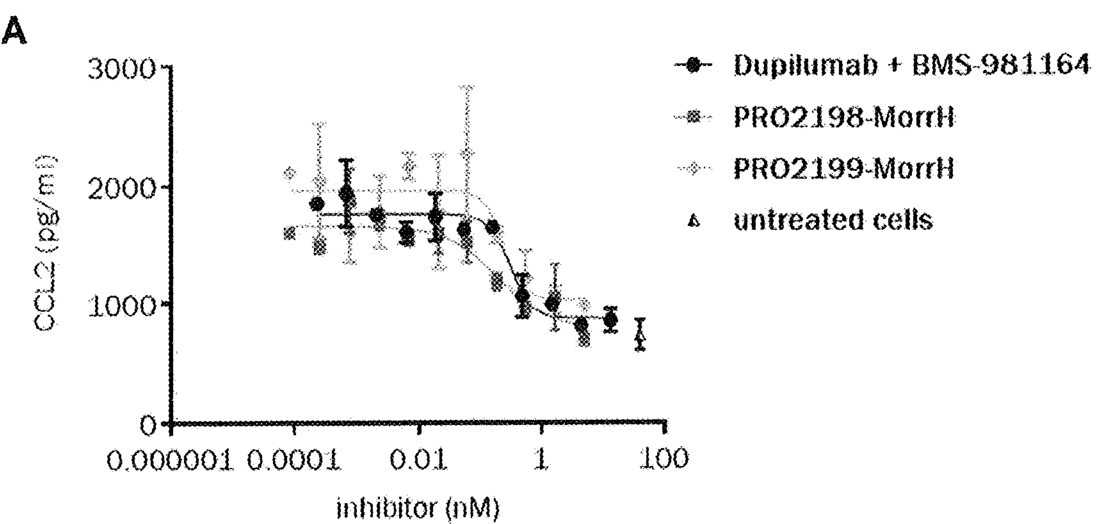
| | Dupilumab + BMS-981164 | PRO2198-MorrH | PRO2199-MorrL |
|---|---|---|---|
| IC50 | 0.3082 | 0.1960 | 0.2408 |
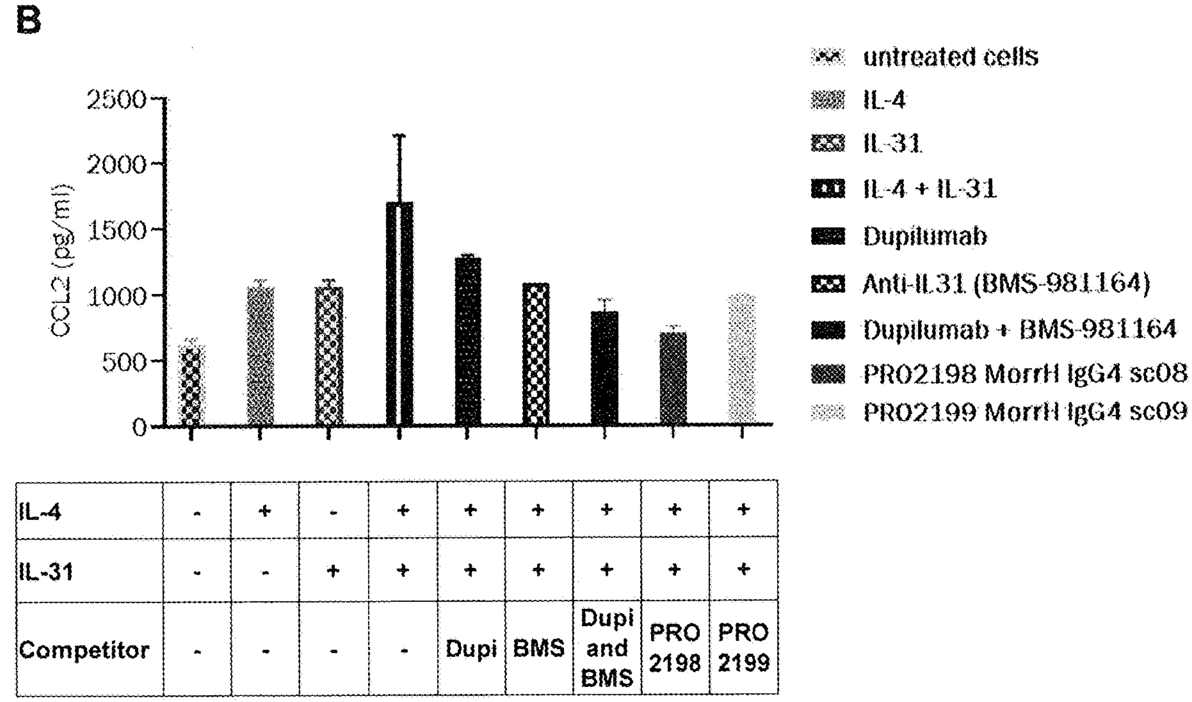
| IL-4 | - | + | - | + | + | + | + | + | + |
|---|---|---|---|---|---|---|---|---|---|
| IL-31 | - | - | + | + | + | + | + | + | + |
| Competitor | - | - | - | - | Dupi | BMS | Dupi and BMS | PRO 2198 | PRO 2199 |

Figure 3:
A
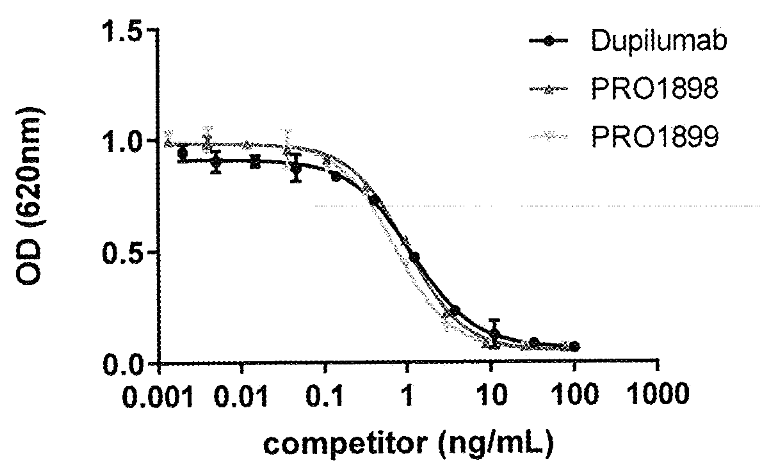
B
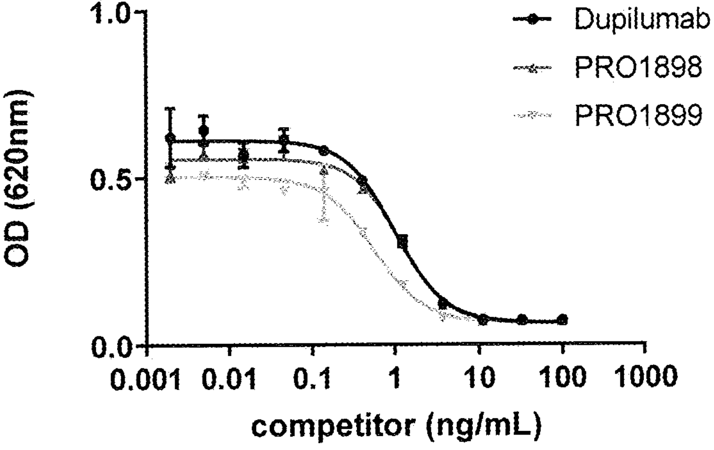

Figure 4:
A
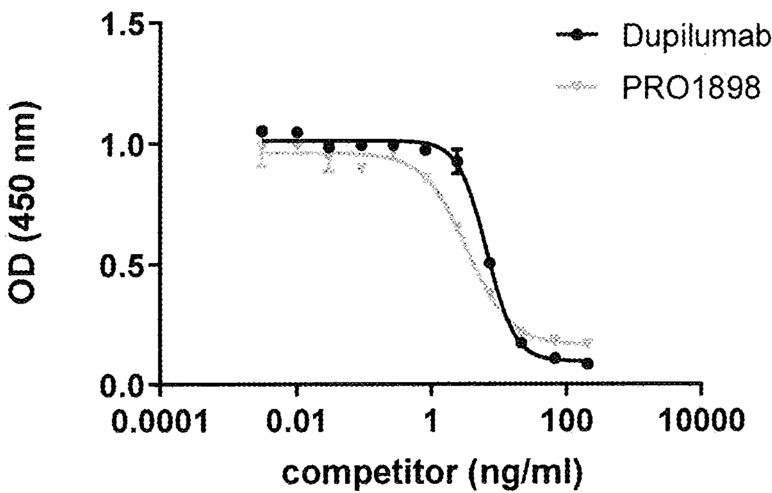
B
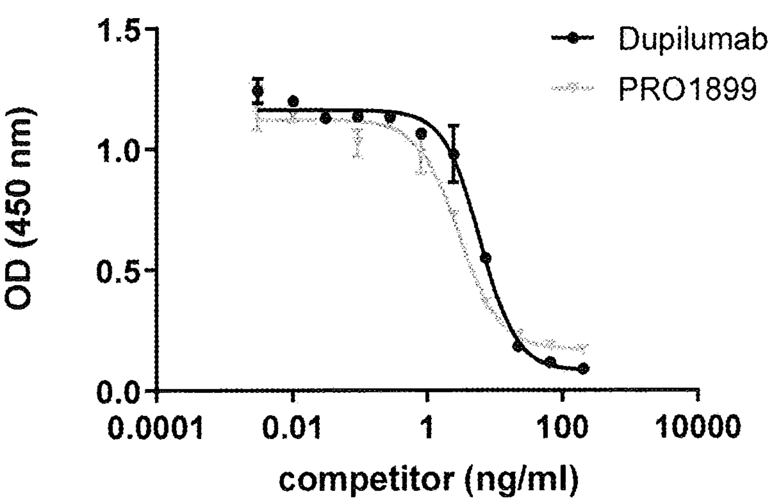

Figure 5:
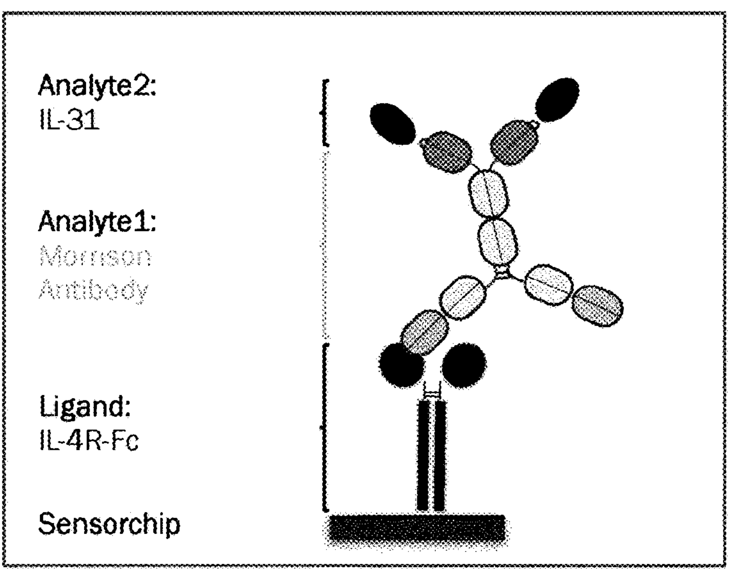
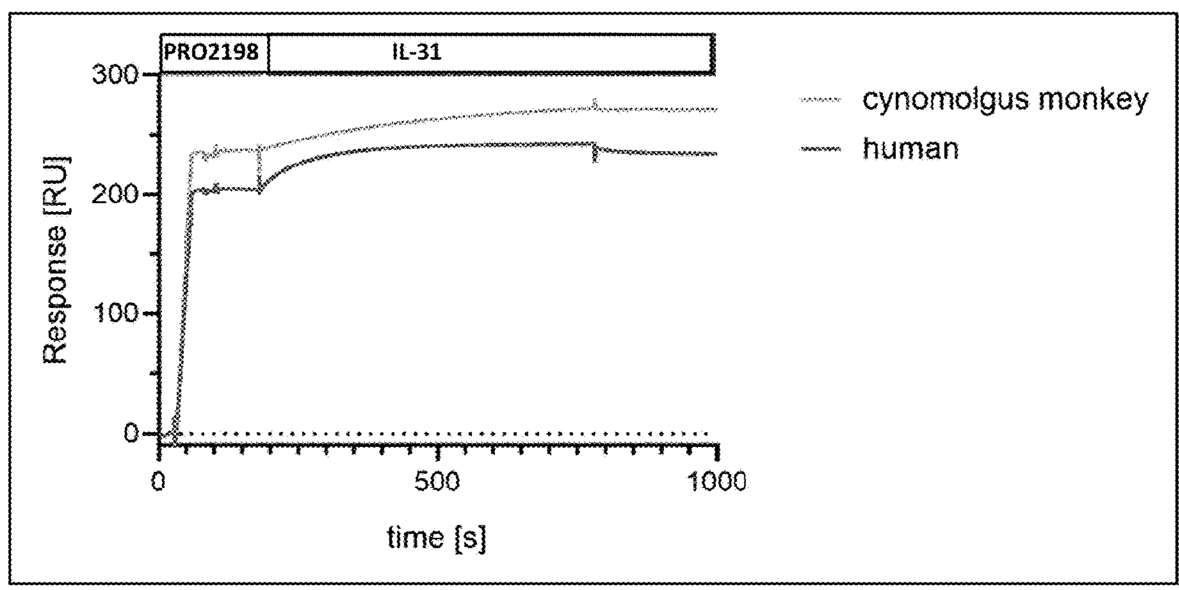

Figure 6:
A
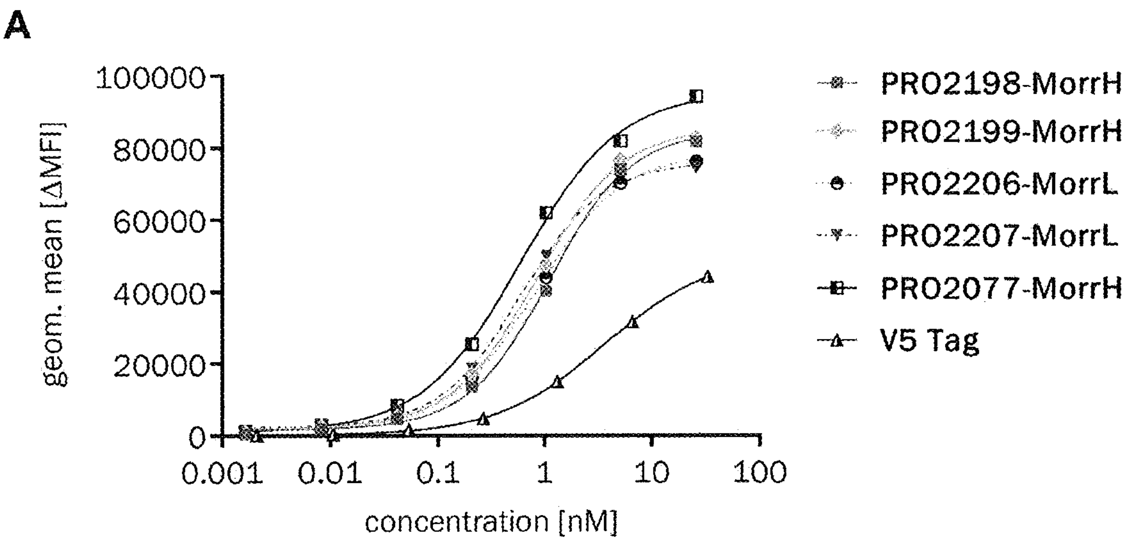
B
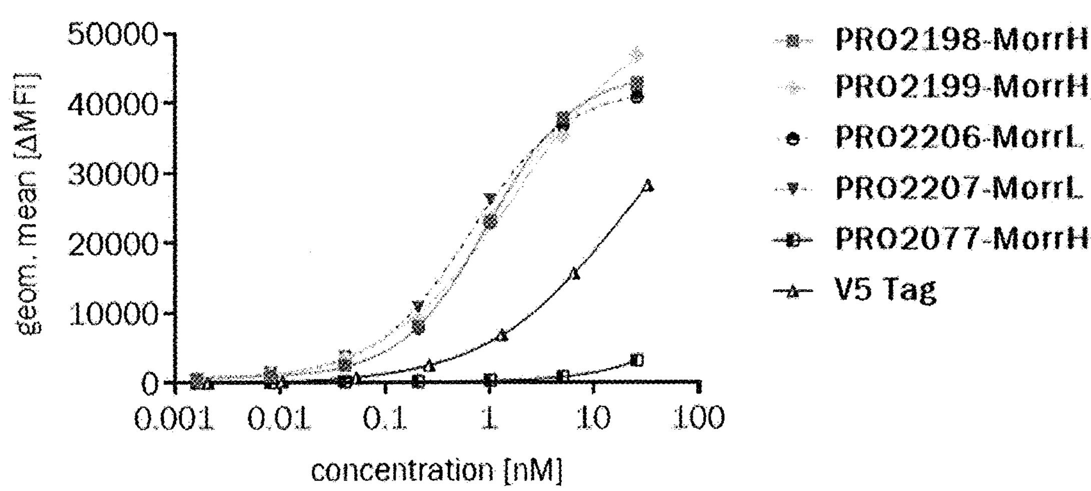

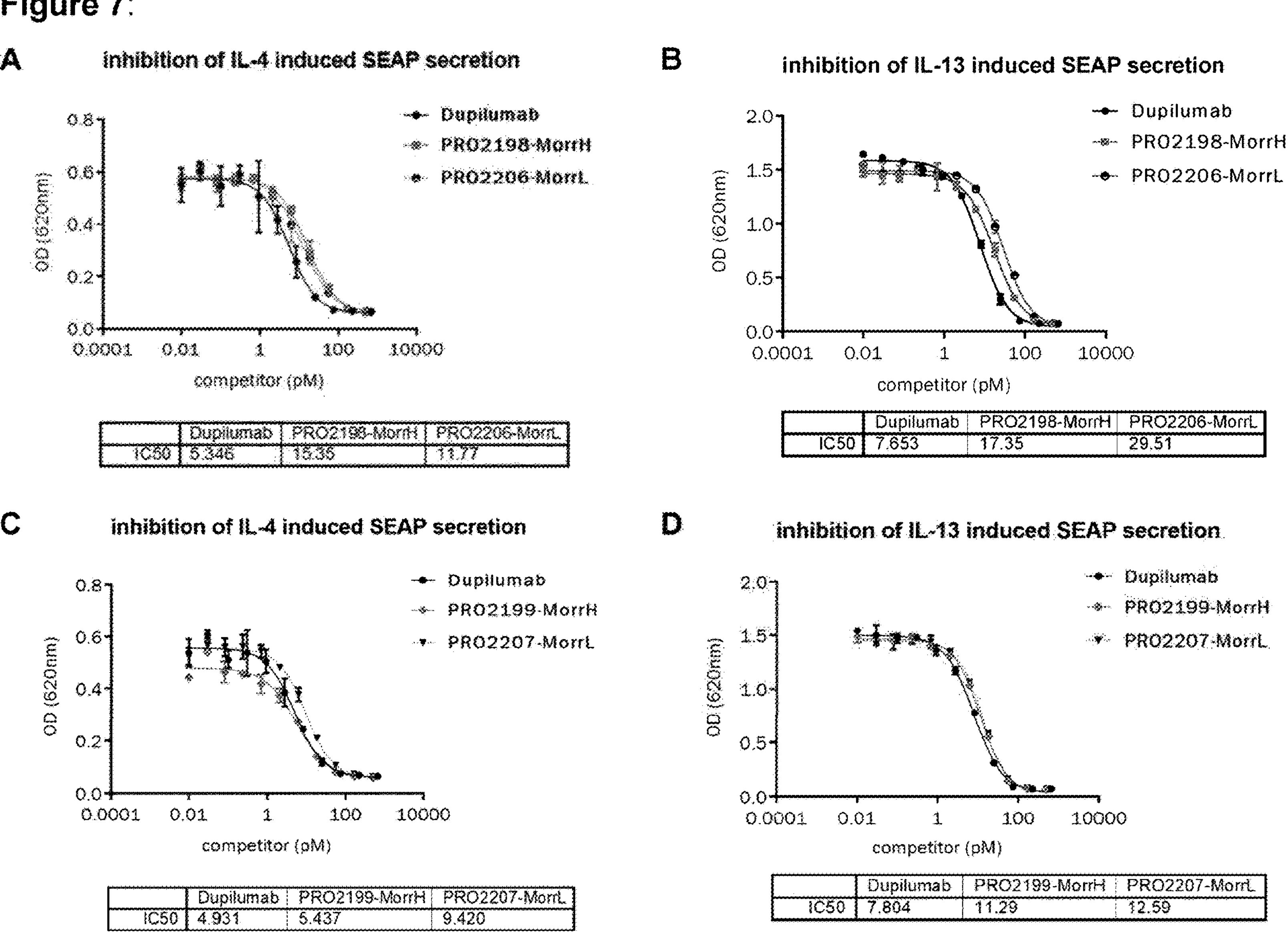
Figure 7:
A
inhibition of IL-4 induced SEAP secretion
Dupilumab
PRO2198-MorrH
PRO2206-MorrL
OD (620nm)
0.8
0.6
0.4
0.2
0.0
0.0001
0.01
1
100
10000
competitor (pM)
Dupilumab | PRO2198-MorrH | PRO2206-MorrL
IC50 | 5.346 | 15.35 | 11.77
B
inhibition of IL-13 induced SEAP secretion
Dupilumab
PRO2198-MorrH
PRO2206-MorrL
OD (620nm)
2.0
1.5
1.0
0.5
0.0
0.0001
0.01
1
100
10000
competitor (pM)
Dupilumab | PRO2198-MorrH | PRO2206-MorrL
IC50 | 7.653 | 17.35 | 29.51
C
inhibition of IL-4 induced SEAP secretion
Dupilumab
PRO2199-MorrH
PRO2207-MorrL
OD (620nm)
0.8
0.6
0.4
0.2
0.0
0.0001
0.01
1
100
10000
competitor (pM)
Dupilumab | PRO2199-MorrH | PRO2207-MorrL
IC50 | 4.931 | 5.437 | 9.420
D
inhibition of IL-13 induced SEAP secretion
Dupilumab
PRO2199-MorrH
PRO2207-MorrL
OD (620nm)
2.0
1.5
1.0
0.5
0.0
0.0001
0.01
1
100
10000
competitor (pM)
Dupilumab | PRO2199-MorrH | PRO2207-MorrL
IC50 | 7.804 | 11.29 | 12.59

A
inhibition of IL-4 induced SEAP secretion
Dupilumab
PRO2198-MorrH
PRO2198-MorrH + IL-31
OD (620nm)
2.5
2.0
1.5
1.0
0.5
0.0
0.0001
0.01
1
100
10000
competitor (pM)
IC50
Dupilumab 15.23
PRO2198-MorrH 21.87
PRO2198-MorrH + IL-31 30.66
B
inhibition of IL-4 induced SEAP secretion
Dupilumab
PRO2199-MorrH
PRO2199-MorrH + IL-31
OD (620nm)
competitor (pM)
IC50
Dupilumab 14.02
PRO2199-MorrH 5.403
PRO2199-MorrH + IL-31 4.312

A
Inhibition of IL-31 induced signaling
BMS-981164
PRO2198-MorrH
PRO2206-MorrL
RLU
40000
30000
20000
10000
0
0.01
1
100
10000
1000000
competitor [pM]
B
Inhibition of IL-31 induced signaling
BMS-981164
PRO2199-MorrH
PRO2207-MorrL
RLU
40000
30000
20000
10000
0
0.01
1
100
10000
1000000
competitor [pM]
C
Inhibition of IL-31 induced signaling
BMS-981164
PRO2198-MorrH
PRO2198-MorrH + IL-4R
RLU
25000
20000
15000
10000
5000
0
0.01
1
100
10000
1000000
competitor [pM]
D
Inhibition of IL-31 induced signaling
BMS-981164
PRO2199-MorrH
PRO2199-MorrH + IL-4R
RLU
25000
20000
15000
10000
5000
0
0.01
1
100
10000
1000000
competitor [pM]

| | BMS-981164 | PRO2198-MorrH | PRO2199-MorrH |
|---|---|---|---|
| IC50 | 177.8 | 959.1 | 1211 |

Figure 11:
A
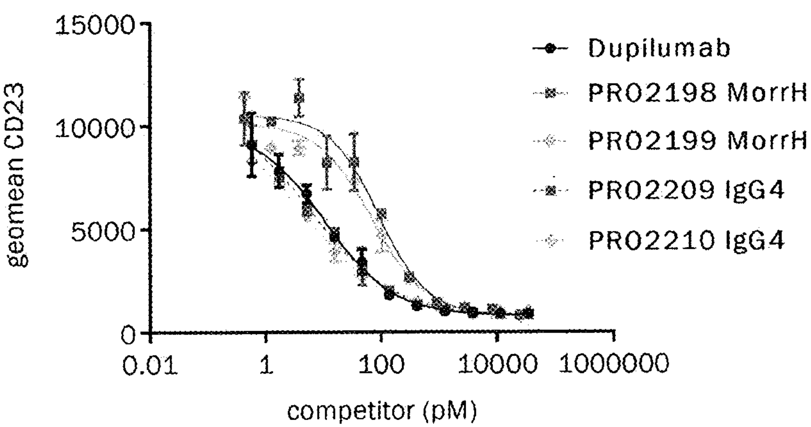
B
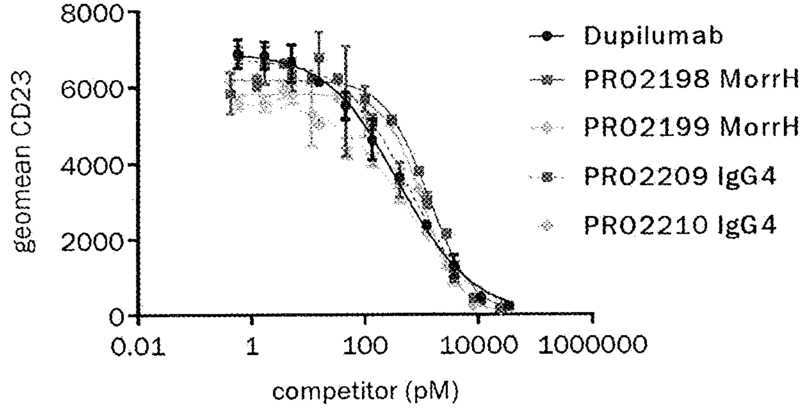
C
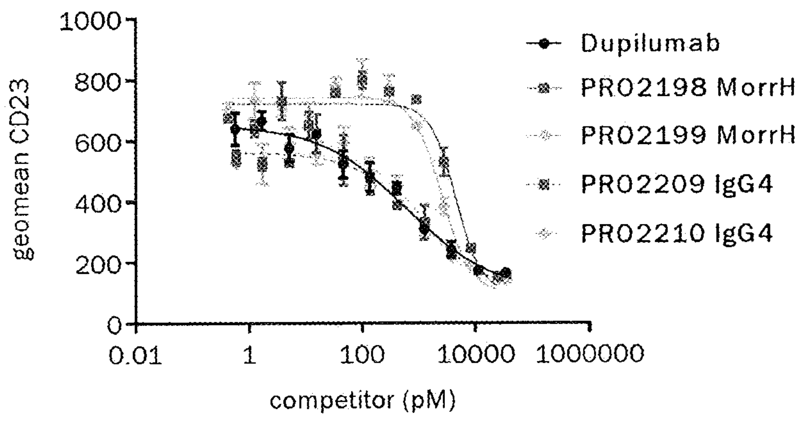

MULTISPECIFIC ANTIBODIES HAVING SPECIFICITY FOR IL-4R AND IL-31, ENCODING NUCLEIC ACIDS THEREOF AND METHODS OF TREATING

CROSS-REFERENCE TO RELATED APPLICATIONS

This application is a 371 National Phase of International Patent Application No. PCT/EP2021/087561 filed on Dec. 23, 2021, which claims priority to European Patent Application No. 20216957.9 filed on Dec. 23, 2020, the content of each of which applications is incorporated herein by reference.

INCORPORATION OF SEQUENCE LISTING

This application contains a sequence listing submitted electronically via EFS-web, which serves as both the paper copy and the computer readable form (CRF) and consists of a file entitled "WRN23NP_seqlist.txt", which was created on Jun. 21, 2023, which is 76,839 bytes in size, and which is herein incorporated by reference in its entirety.

FIELD OF THE INVENTION

The present invention relates to a multispecific antibody comprising one or two binding domains, which specifically bind to IL-4R (IL4R-BDs), and one or two binding domains, which specifically bind to IL-31 (IL31-BDs), wherein the multispecific antibody comprises an immunoglobulin Fc region. The present invention further relates to nucleic acids encoding said multispecific antibody, vector(s) comprising said nucleic acids, host cell(s) comprising said nucleic acids or said vector(s), and a method of producing said multispecific antibody. Additionally, the present invention relates to pharmaceutical compositions comprising said multispecific antibody and methods of use thereof.

BACKGROUND OF THE INVENTION

The interleukin-4 receptor IL-4Rα, herein also referred to as IL-4R or IL4R, is a type I receptor. It binds interleukin 4 (IL-4) either upon direct interaction with the common cytokine receptor gamma chain ($\gamma_c$) or by forming receptor complexes with type II receptors, such as in particular with the type II receptor IL-13Rα1. This IL-4R/IL-13Rα1 receptor complex can bind interleukin 4 (IL-4) as well as interleukin 13 (IL-13) to regulate IgE antibody production in B cells. IL-4 binding to IL-4R is further known to activate macrophages and to promote differentiation of type 2 helper T-cells (Th2-cells), leading to Th2-driven inflammation. IL-4 and/or IL-13 binding to IL-4Rα/$\gamma_c$ and/or IL-4R/IL-13Rα1 leads to the activation of Janus kinase (JAK)1, JAK2, signal transducer and activator of transcription (STAT)1, STAT3, STAT6, and STAT dimerization, which in turn induces the transcription of specific genes.

IL-4R signaling has been shown to be associated with a number of human diseases, such as inflammatory and autoimmune disorders, including atopic dermatitis, prurigo nodularis, nasal polyposis, chronic urticaria, asthma and chronic obstructive pulmonary disease.

Several monoclonal antibodies, which reduce or block IL4R-mediated signaling by either binding the cytokines IL-4 and/or IL-13 or to the IL-4R, have been described in the prior art for the treatment of such diseases. For example, dupilumab (Dupixent®) developed by Regeneron Pharmaceuticals and Sanofi Genzyme, which bind to and antagonizes IL-4R, has been approved for the treatment of moderate-to-severe atopic dermatitis and for the treatment of chronic rhinosinusitis with nasal polyposis (CRSwNP). It is also being evaluated for treatment of persistent asthma in adults and adolescents.

Atopic dermatitis (AD) is a chronic inflammatory skin disease characterized by intense pruritus (e.g., severe itch) and by scaly and dry eczematous lesions. Severe disease can be extremely disabling due to major psychological problems, significant sleep loss, and impaired quality of life, leading to high socioeconomic costs. AD often begins in childhood before age 5 and may persist into adulthood.

The pathophysiology of AD is influenced by a complex interplay between immunoglobulin E (IgE)-mediated sensitization, the immune system, and environmental factors. The primary skin defect may be an immunological disturbance that causes IgE-mediated sensitization, with epithelial-barrier dysfunction that is the consequence of both genetic mutations and local inflammation.

Typical treatments for AD include topical lotions and moisturizers, topical corticosteroid ointments, creams or injections. Most treatment options, however, offer only temporary, incomplete symptom relief. Moreover, many patients with moderate-to-severe AD become resistant to treatment by topical corticosteroids or by calcineurin inhibitors. Therefore, more targeted therapies for the treatment and/or prevention of AD have been developed, such as monoclonal anti-IL4R antibodies that antagonize IL4R function.

For example, WO 2014/039461 describes anti-IL4R antagonistic antibodies for use in the treatment of atopic dermatitis.

Furthermore, as already indicated above, the anti-IL-4R monoclonal antibody dupilumab (Dupixent®) received approval from the United States Food and Drug Administration for moderate-to-severe atopic dermatitis in 2017 and for asthma in 2018.

However, anti-IL-4R therapies have significant limitations. For example, their efficacy in the atopic diseases of interest is often limited and the response rates are often low to moderate. Furthermore, anti-IL-4R therapies do not directly address itching. Itching, however, is a common symptom in skin-associated inflammatory and autoimmune disorders, such as in the case of AD. Itch-associated scratching generally promotes inflammation and worsening of the disease-related symptoms. Thus, there is a critical need for additional treatment options for patients living with moderate to severe atopic dermatitis and other itch-causing inflammatory and autoimmune disorders.

More specifically, there is a clear need for novel and improved therapeutic antibodies being able to more efficiently reduce or eliminate IL-4- and/or IL-13-mediated signaling activity in said allergic, inflammatory and autoimmune diseases, but also address the itching symptoms (pruritus) associated with these diseases.

Said therapeutic antibodies should have a high potency as well as a tolerable safety profile to keep dose limiting side effects at a low level. This is particularly important in case of the treatment of chronic diseases, which typically require long term application of said therapeutic antibodies. Furthermore, it is desirable that said therapeutic antibodies have superior biophysical properties, such as a high stability, in order to facilitate developability and producibility in high yields. In particular, they should have a good storage stability at high concentrations to allow the preparation of highly concentrated formulations for subcutaneous injection applications. Subcutaneous injection is highly desirable and a necessary prerequisite to enable patients to apply the medication themselves.

SUMMARY OF THE INVENTION

It is an object of the present invention to provide a medicament to improve treatment of allergic, inflammatory and autoimmune diseases, particularly to provide a new, superior treatment modality for pruritus-causing inflammatory and autoimmune diseases, such as moderate to severe atopic dermatitis. More specifically, it is an object of the present invention to provide novel and improved therapeutic antibodies that are able to efficiently reduce or eliminate IL-4- and IL-13-mediated activity in said diseases and that are also able to address the itching symptoms associated with these diseases. It is a further object of the present invention that said novel and improved therapeutic antibodies exhibit high stability at protein concentrations above 100 mg/ml to allow their application by subcutaneous injection.

The inventors have now surprisingly found that multispecific antibodies comprising one or two IL-4R antagonizing binding domains (IL4R-BDs) and one or two IL-31 neutralizing binding domains (IL31-BDs) can simultaneously block IL-4-/IL-13- as well as IL-31-induced signaling in a highly efficient manner, which allows the simultaneous reduction of IL-4-/IL-13-related symptoms as well as of the itch-related IL-31 activity.

The inventors have further surprisingly found through testing of many different antibody formats, that said anti-IL-4R×IL-31 multispecific antibodies, when comprising a functional Fc region, in particular an IgG region comprising a functional Fc region, can block IL-4- and IL-13-induced signaling even better and have very advantageous biophysical properties, in particular an outstanding stability, which allows the preparation of storage stable formulations for antibody concentrations well above 100 mg/ml. Tested formats that did not exhibit the desired combined properties, i.e. the desired high inhibition potency and at the same time the desired high storage stability, were in particular MATCH3, scMATCH3, $(scFv)_2Fc(scFv)_2$ and Morrison IgG1 (silenced). These multispecific antibody formats were studied intensively. The tested MATCH3- and scMATCH3-based multispecific antibodies exhibited good stability but lacked efficacy in inhibiting IL-4R- and IL-31-mediated signaling. The tested $(scFv)_2Fc(scFv)_2$-based multispecific antibodies showed improved inhibition potency but was only moderately stable when stored at concentrations above 100 mg/ml for longer time periods. The tested silenced IgG1 Morrison-based multispecific antibodies on the other hand exhibited excellent storage stability at high concentrations but did not completely reach the desired inhibition potency. It was concluded that a functional Fc region, in particular a functional IgG region is necessary for the desired inhibition potency.

Accordingly, in a first aspect, the present invention relates to a multispecific antibody comprising:

a) one or two binding domains, which specifically bind to IL-4R (IL4R-BD), and
b) one or two binding domains, which specifically bind to IL-31 (IL31-BD),
   wherein the multispecific antibody comprises an immunoglobulin Fc region, in particular an IgG region.

In a second aspect, the present invention relates to a nucleic acid or two nucleic acids encoding the multispecific antibody of the present invention.

In a third aspect, the present invention relates to a vector or two vectors comprising the nucleic acid or the two nucleic acids of the present invention.

In a fourth aspect, the present invention relates to a host cell or host cells comprising the vector or the two vectors of the present invention.

In a fifth aspect, the present invention relates to a method for producing the multispecific antibody of the present invention, comprising (i) providing the nucleic acid or the two nucleic acids of the present invention, or the vector or the two vectors of the present invention, expressing said nucleic acid or said two nucleic acids, or said vector or vectors, and collecting said multispecific antibody from the expression system, or (ii) providing a host cell or host cells of the present invention, culturing said host cell or said host cells; and collecting said multispecific antibody from the cell culture.

In a sixth aspect, the present invention relates to a pharmaceutical composition comprising the multispecific antibody of the present invention and a pharmaceutically acceptable carrier.

In a seventh aspect, the present invention relates to a multispecific antibody of the present invention for use as a medicament.

In an eighth aspect, the present invention relates to a multispecific antibody of the present invention for use in the treatment of a disease, particularly a human disease, more particularly a human disease selected from allergic, inflammatory and autoimmune diseases, particularly from inflammatory and autoimmune diseases.

In a ninth aspect, the present invention relates to a method for the treatment of a disease, particularly a human disease, more particularly a human disease selected from allergic, inflammatory and autoimmune diseases, particularly from inflammatory and autoimmune diseases, comprising the step of administering the multispecific antibody of the present invention to a patient in need thereof.

The aspects, advantageous features and preferred embodiments of the present invention summarized in the following items, respectively alone or in combination, further contribute to solving the object of the invention:

1. A multispecific antibody comprising:
   a) one or two binding domains, which specifically bind to IL-4R (IL4R-BD), in particular two identical IL4R-BDs, and
   b) one or two binding domains, which specifically bind to IL-31 (IL31-BD), in particular two identical IL31-BDs,
   wherein the multispecific antibody comprises an immunoglobulin Fc region, in particular a functional Fc region.
2. The multispecific antibody of item 1, wherein
   each of said IL4R-BDs comprises
   the HCDR1 sequence of SEQ ID NO: 1,
   the HCDR2 sequences of SEQ ID NO: 2,
   the HCDR3 sequence of SEQ ID NO: 3,
   the LCDR1 sequence of SEQ ID NO: 7,
   the LCDR2 sequence of SEQ ID NO: 8, and
   the LCDR3 sequences of SEQ ID NO: 9; and
   each of said IL31-BDs comprises
   the HCDR1 sequence of SEQ ID NO: 12,
   the HCDR2 sequence of SEQ ID NO: 13,
   the HCDR3 sequences of SEQ ID NO: 14,
   the LCDR1 sequence of SEQ ID NO: 17 or 18,
   the LCDR2 sequence of SEQ ID NO: 19, and
   the LCDR3 sequences of SEQ ID NOs: 20.

3. The multispecific antibody of item 1 or 2, wherein the format of said multispecific antibody is selected from $(scFv)_2$-Fc-$(scFv)_2$ fusion (ADAPTIR); DVD-Ig; a DART™ and a TRIDENT™.
4. The multispecific antibody of item 1 or 2, wherein the multispecific antibody comprises an IgG region.
5. The multispecific antibody of item 4, wherein the format of said multispecific antibody is selected from bivalent bispecific IgG formats, trivalent bispecific IgG formats and tetravalent bispecific IgG formats;
   in particular wherein the format of said multispecific antibody is selected from KiH-based IgGs; DVD-Ig; IgG-scFv fusions, such as CODV-IgG, Morrison (IgG $CH_3$-scFv fusion (Morrison-H) or IgG CL-scFv fusion (Morrison-L)), bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain) and Ts2Ab (dsscFv linked to C-terminus of heavy chain);
   more particularly wherein the format of said multispecific antibody is selected from KiH-based IgGs; DVD-Ig; CODV-IgG and Morrison (IgG $CH_3$-scFv fusion (Morrison-H) or IgG CL-scFv fusion (Morrison-L)), even more particularly from DVD-Ig and Morrison (IgG $CH_3$-scFv fusion (Morrison-H) or IgG CL-scFv fusion (Morrison-L)).
6. The multispecific antibody of item 5, wherein the format of said multispecific antibody is selected from Morrison formats.
7. The multispecific antibody of any one of the preceding items, wherein said multispecific antibody comprises two IL4R-BDs.
8. The multispecific antibody of any one of the preceding items, wherein said multispecific antibody comprises two IL31-B3Ds.
9. The multispecific antibody of item 1, wherein said multispecific antibody comprises:
   a) two binding domains, which specifically bind to IL-4R (IL4R-BD), and
   b) two binding domains, which specifically bind to IL-31 (IL31-BD),
   wherein said multispecific antibody comprises an IgG region, particularly wherein the format of the multispecific antibody is selected from a Morrison format;
   and wherein
   each of said IL4R-BDs comprise
   the HCDR1 sequence of SEQ ID NO: 1,
   the HCDR2 sequences of SEQ ID NO: 2,
   the HCDR3 sequence of SEQ ID NO: 3,
   the LCDR1 sequence of SEQ ID NO: 7,
   the LCDR2 sequence of SEQ ID NO: 8, and
   the LCDR3 sequences of SEQ ID NO: 9; and
   each of said IL31-BDs comprise
   the HCDR1 sequence of SEQ ID NO: 12,
   the HCDR2 sequence of SEQ ID NO: 13,
   the HCDR3 sequences of SEQ ID NO: 14,
   the LCDR1 sequence of SEQ ID NO: 17 or 18,
   the LCDR2 sequence of SEQ ID NO: 19, and
   the LCDR3 sequences of SEQ ID NOs: 20.
10. The multispecific antibody of any one of the preceding items, wherein said multispecific antibody acts as an antagonist of IL4R.
11. The multispecific antibody of item 10, wherein said multispecific antibody blocks the binding of IL4 and IL13 to IL4R.
12. The multispecific antibody of any one of the preceding items, wherein said multispecific antibody blocks the binding of IL-31 to the interleukin 31 receptor alpha (IL-31RA)/oncostatin M receptor (OSMR) complex (IL-31RA/OSMR complex).
13. The multispecific antibody of any one of items 1 to 12, wherein said multispecific antibody has a solubility of at least 100 mg/ml, particularly of at least 120 mg/ml, when formulated in 20 mM acetate buffer at pH 5.5.
14. The multispecific antibody of any one of items 1 to 12, wherein said multispecific antibody, when formulated in 20 mM acetate buffer at pH 5.5, can be concentrated to 100 mg/ml and more, particularly to 100-200 mg/ml, particularly to 100-150 mg/ml, with less than 2%, particularly with less than 1%, loss of monomeric content, as determined by SE-chromatography.
15. The multispecific antibody of any one of items 1 to 12, wherein said multispecific antibody, when formulated in 20 mM acetate buffer at pH 5.5, has a monomeric content of at least 95%, particularly of at least 97%, at concentrations of 100 mg/ml and above, particularly at concentrations in the range of from 100-150 mg/ml.
16. The multispecific antibody of items 1 to 12, wherein said multispecific antibody has a loss in monomer content, after storage at 4° C. for four weeks, of less than 5%, e.g. less than 4%, less than 3%, less than 2%, preferably less than 1%, when said multispecific antibody is at a starting concentration of 100 mg/ml, in particular wherein said multispecific antibody is formulated in 20 mM acetate buffer at pH 5.5.
17. The multispecific antibody of any one of the preceding items, wherein the amount of CCL2 secretion of BEAS-2B cells, that are treated with 1 ng/ml IL-4 and 10 ng/ml IL-31, in the presence of 1 μg/ml of said multispecific antibodies is either decreased or only increased by a factor of 1.00 to 1.50, particularly by a factor of 1.00 to 1.4, particularly by a factor of 1.00 to 1.30, particularly by a factor of 1.00 to 1.20, when compared to the amount of CCL2 secretion of untreated BEAS-2B cells.
18. The multispecific antibody of any one of the preceding items, wherein the immunoglobulin Fc region is selected from an IgG subclass, particularly from IgG subclasses IgG1 and IgG4, particularly from IgG4.
19. The multispecific antibody of item 6, wherein the IL4R-BDs are located in the Fab arms, and the IL31-BDs are located in the scFv part of the Morrison format.
20. The multispecific antibody of any one of items 6 and 19, wherein the format of the multispecific antibody is selected from a Morrison-L and a Morrison-H format, in particular wherein the format is a Morrison-H format.
21. The multispecific antibody of any of the preceding items, wherein said IL4R-BDs:
   a. bind to human IL-4R with a monovalent dissociation constant ($K_D$) of 0.1 to 200 pM, particularly with a $K_D$ of 0.1 to 100 pM, particularly of 0.1 to 50 pM, as measured by surface plasmon resonance (SPR), particularly wherein said IL4R-BDs are in an scFv format;
   b. are cross-reactive with *Macaca fascicularis* (Cynomolgus) IL4R, in particular bind to in particular bind to Cynomolgus IL-4R with a monovalent $K_D$ of 1 pM to 5 nM, particularly of 1 pM to 3 nM, particularly of 1 pM to 2 nM, as measured by SPR, particularly wherein said IL4R-BDs are in an scFv format;

c. are cross-reactive with Callithrix jacchus (Marmoset) IL-4R, in particular bind to Marmoset IL-4R with a monovalent $K_D$ of 1 pM to 5 nM, particularly of 1 pM to 3 nM, particularly of 1 pM to 2 nM, as measured by SPR, particularly wherein said IL4R-BDs are in an scFv format;

d. neutralize the human IL-4-induced signaling with an $IC_{50}$ of 0.01 to 5 ng/ml, particularly with an $IC_{50}$ of 0.01 to 3 ng/ml, particularly with an $IC_{50}$ of 0.01 to 1.5 ng/ml, as measured in a stat6 reporter gene assay in HEK-Blue cells, wherein said IL4R-BDs are in an scFv format;

e. neutralize the human IL-13-induced signaling with an $IC_{50}$ of 0.01 to 10 ng/ml, particularly with an $IC_{50}$ of 0.01 to 5 ng/ml, particularly with an $IC_{50}$ of 0.01 to 2.5 ng/ml, as measured in a stat-6 reporter gene assay in HEK-Blue cells, wherein said IL4R-BDs are in an scFv format;

f. inhibit the binding of human IL-4 to human IL-4R with an $IC_{50}$ of 0.01 to 10 ng/ml, particularly with an $IC_{50}$ of 0.01 to 5 ng/ml, particularly with an $IC_{50}$ of 0.01 to 2 ng/ml, as measured in a competition ELISA, wherein said IL4R-BDs are in an scFv format;

g. when being in scFv format, has a melting temperature (Tm), determined by differential scanning fluorimetry (DSF), of at least 63° C., particularly of at least 65° C., particularly of at least 67° C., particularly of at least 69° C., particularly of at least 70° C., particularly of at least 71° C., particularly of at least 72° C., in particular wherein said scFvs are formulated in 50 mM phosphate citrate buffer with 150 mM NaCl at pH 6.4;

h. when being in scFv format, has a loss in monomer content, after storage for four weeks at 4° C. of less than 5%, when said scFvs are at a starting concentration of 10 mg/ml, and in particular wherein said scFvs are formulated in 50 mM phosphate citrate buffer with 150 mM NaCl at pH 6.4; and/or i. when being in scFv format, has a loss in monomer content, after 5 freeze-thawing cycles, of less than 5%, e.g. less than 4%, less than 3%, preferably less than 2%, when said scFvs are at a starting concentration of 10 mg/ml, and in particular wherein said scFvs are formulated in 50 mM phosphate citrate buffer with 150 mM NaCl at pH 6.4.

22. The multispecific antibody of any one of the preceding items, wherein said IL4R-BDs comprise VH3 or VH4 domain framework sequences FR1 to FR4; particularly VH3 domain framework sequences FR1 to FR4.

23. The multispecific antibody of any one of item 23, wherein said IL4R-BDs, when being in scFv-format, comprise (i) a VL domain comprising a VL framework comprising framework regions FR1, FR2 and FR3, which are selected from VK subtypes, particularly from the VK1 and VK3 subtypes, particularly are of the VK1 subtype, and a framework FR4, which is selected from a VK FR4 and a VA FR4, particularly is a VA FR4 comprising an amino acid sequence having at least 70, 80, 90 percent identity to a VA FR4 sequence selected from SEQ ID NO: 26 to SEQ ID NO: 33, more particularly a VA FR4 selected from SEQ ID NO: 26 to SEQ ID NO: 33, particularly VA FR4 according to SEQ ID NO: 26 or 33.

24. The multispecific antibody of any one of the preceding items, wherein said IL4R-BDs comprise a) a VH sequence at least 90, 91, 92, 93, 94, 95, 96, 97, 98 or 99 percent identical to an amino acid sequence selected from SEQ ID NO: 4, 5 and 6; and b) a VL sequence at least 90, 91, 92, 93, 94, 95, 96, 97, 98 or 99 percent identical to an amino acid sequence selected from SEQ ID NO: 10 and 11.

25. The multispecific antibody of any one of the preceding items, wherein said IL4R-BDs comprise a) a VH sequence selected from SEQ ID NOs: 4, 5 and 6, b) a VL sequence selected from SEQ ID NOs: 10 and 11.

26. The multispecific antibody of any one of the preceding items, wherein said IL4R-BDs comprise a) a VH sequence of SEQ ID NO: 4 and a VL sequence of SEQ ID NO: 11; or b) a VH sequence of SEQ ID NO: 5 and a VL sequence of SEQ ID NO: 10; or c) a VH sequence of SEQ ID NO: 6 and a VL sequence of SEQ ID NO: 10.

27. The multispecific antibody of any of the preceding items, wherein said IL31-BDs:

a. bind to human IL-31 with a monovalent dissociation constant ($K_D$) of 5 nM or less, particularly with a monovalent $K_D$ of 5 pM to 5 nM, particularly of 5 pM to 2 nM, particularly of 5 to 1000 pM, as measured by surface plasmon resonance (SPR), particularly wherein said IL31-BDs are in an scFv;

b. are cross-reactive with *Macaca fascicularis* (Cynomolgus) IL-31, in particular bind to Cynomolgus IL-31 with a monovalent $K_D$ of 5 nM or less, particularly with a monovalent $K_D$ of 5 pM to 5 nM, particularly of 5 pM to 2 nM, particularly of 5 to 1000 pM, as measured by SPR, particularly wherein said IL31-BDs are in an scFv;

c. inhibit the human IL-31-induced signaling with an $IC_{50}$ of 0.1 to 30 ng/ml, particularly with an $IC_{50}$ of 0.1 to 20 ng/ml, particularly with an $IC_{50}$ of 0.1 to 10 ng/ml, as measured in a Path Hunter IL-31RA/OSMRb dimerization assay, wherein said IL31-BDs are in an scFv format;

d. block the binding of human IL-31 to human IL-31R with an $IC_{50}$ of 0.1 to 20 ng/ml, particularly with an $IC_{50}$ of 0.1 to 10 ng/ml, particularly with an $IC_{50}$ of 0.2 to 6 ng/ml, as measured in a competition ELISA, wherein said IL31-BDs are in an scFv format;

e. when being in scFv format, have a melting temperature (Tm), determined by differential scanning fluorimetry, of at least 65° C., preferably of at least 67° C., more preferably at least 69° C., in particular wherein said scFvs are formulated in 50 mM phosphate citrate buffer with 150 mM NaCl at pH 6.4;

f. when being in scFv format, have a loss in monomer content, after storage for at least four weeks at 4° C. of less than 5%, e.g. less than 4%, less than 3%, less than 2%, preferably less than 1%, when said scFvs are at a starting concentration of 10 mg/ml, and in particular wherein said scFvs are formulated in 50 mM phosphate citrate buffer with 150 mM NaCl at pH 6.4;

g. when being in scFv format, have a loss in monomer content, after storage for four weeks at 40° C. of less than 5%, e.g. less than 4%, less than 3%, less than 2%, preferably less than 1%, when said scFvs are at a starting concentration of 10 mg/ml, and in particular wherein said scFvs are formulated in 50 mM phosphate citrate buffer with 150 mM NaCl at pH 6.4;

h. when being in scFv format, have a loss in monomer content, after 3 freeze-thawing cycles, of less than 5%, e.g. less than 4%, less than 3%, less than 2%, preferably less than 1%, when said scFvs are at a starting concentration of 10 mg/ml, and in particular wherein said scFvs are formulated in 50 mM phosphate citrate buffer with 150 mM NaCl at pH 6.4; and/or i. when being in scFv format, have a loss in protein content, after storage for four weeks at 4° C. or 40° C. of less than 5%, e.g. less than 4%, less than 3%, less than 2%, preferably less than 1%, when said scFv is at a starting concentration of 10 mg/ml, and in particular wherein said scFv is formulated in 50 mM phosphate citrate buffer with 150 mM NaCl at pH 6.4.

28. The multispecific antibody of any one of the preceding items, wherein said IL31-BDs comprise VH3 or VH4 domain framework sequences FR1 to FR4; particularly VH3 domain framework sequences FR1 to FR4.

29. The multispecific antibody of item 28, wherein said IL31-BDs, when being in scFv-format, comprise (i) a VL domain comprising a VL framework comprising framework regions FR1, FR2 and FR3, which are selected from VK subtypes, particularly from the VK1 and VK3 subtypes, particularly are of the VK1 subtype, and a framework FR4, which is selected from a VK FR4 and a VA FR4, particularly is a VA FR4 comprising an amino acid sequence having at least 70, 80, 90 percent identity to a VA FR4 sequence selected from SEQ ID NO: 26 to SEQ ID NO: 33, more particularly a VA FR4 selected from SEQ ID NO: 26 to SEQ ID NO: 33, particularly VA FR4 according to SEQ ID NO: 26 or 33.

30. The multispecific antibody of any one of the preceding items, wherein said IL31-BDs comprise a) a VH sequence at least 90, 91, 92, 93, 94, 95, 96, 97, 98 or 99 percent identical to an amino acid sequence selected from SEQ ID NOs: 15 and 16; and b) a VL sequence at least 90, 91, 92, 93, 94, 95, 96, 97, 98 or 99 percent identical to an amino acid sequence selected from SEQ ID NOs: 21 and 22.

31. The multispecific antibody of any one of the preceding items, wherein said IL31-BD comprises a) a VH sequence selected from SEQ ID NOs: 15 and 16, particularly the VH sequence of SEQ ID NO: 16; and b) a VL sequence selected from SEQ ID NOs: 21 and 22, particularly the VL sequence of SEQ ID NO: 21.

32. The multispecific antibody of any one of the preceding items, wherein at least one of said IL4R-BDs and/or at least one of said IL31-BDs comprises CDR regions derived from a parental rabbit antibody.

33. The multispecific antibody of any one of the preceding items, wherein at least one IL4R-BD and at least one IL31-BD are capable of binding simultaneously to their respective antigens.

34. The multispecific antibody of any one of the preceding items, wherein said multispecific antibody:

a. binds to human IL-4R with a monovalent dissociation constant ($K_D$) of 1000 pM or less, particularly with a $K_D$ of 1 to 1000 pM, particularly of 1 to 700 pM, particularly of 1 to 500 pM, as measured by surface plasmon resonance (SPR);

b. is cross-reactive with *Macaca fascicularis* (Cynomolgus) IL4R, in particular bind to Cynomolgus IL-4R with a monovalent $K_D$ of less than 50 nM, particularly less than 20 nM, particularly with a monovalent $K_D$ of 1 pM to 5 nM, particularly of 1 pM to 2 nM, particularly of 1 to 1000 pM, particularly of 1 to 500 pM, as measured by SPR;

c. binds to human IL-31 with a monovalent $K_D$ of less than 5 nM, particularly with a monovalent $K_D$ of 5 pM to 5 nM, particularly of 5 pM to 2 nM, particularly of 5 pM to 1000 pM, as measured by SPR;

d. is cross-reactive with *Macaca fascicularis* (Cynomolgus) IL-31, in particular binds to Cynomolgus IL-31 with a monovalent $K_D$ of 20 nM or less, particularly with a monovalent $K_D$ of 5 pM to 20 nM, particularly of 5 pM to 10 nM, particularly of 5 pM to 5 nM, as measured by SPR;

e. neutralizes the human IL-4-induced signaling with an $IC_{50}$ of 0.2 pM to 200 pM, particularly with an $IC_{50}$ of 0.2 pM to 100 pM, particularly with an $IC_{50}$ of 0.2 pM to 50 pM, as measured in a stat-6 reporter gene assay in HEK-Blue cells;

f. neutralizes the human IL-13-induced signaling with an $IC_{50}$ of 0.2 pM to 200 pM, particularly with an $IC_{50}$ of 0.2 pM to 100 pM, particularly with an $IC_{50}$ of 0.2 pM to 50 pM, as measured in a stat-6 reporter gene assay in HEK-Blue cells;

g. blocks the human IL-4- and the human IL-13-induced thymus activation regulated chemokine (TARC) secretion with an $IC_{50}$ of 10 pM to 2 nM, particularly with an $IC_{50}$ of 10 pM to 1 nM, as measured in a human whole blood assay;

h. binds to HEK293T cells expressing human IL-4R with an $EC_{50}$ of 0.01 to 10 nM, particularly with an $EC_{50}$ of 0.01 to 7 nM, particularly with an $EC_{50}$ of 0.01 to 5 nM;

i. binds to HEK293T cells expressing Cynomolgus IL-4R with an $EC_{50}$ of 0.01 to 10 nM, particularly with an $EC_{50}$ of 0.01 to 7 nM, particularly with an $EC_{50}$ of 0.01 to 5 nM;

j. blocks the human IL-31-induced signaling with an $IC_{50}$ of 5 pM to 2 nM, particularly with an $IC_{50}$ of 5 pM to 1 nM, particularly with an $IC_{50}$ of 5 to 700 pM, as measured in a Path Hunter IL-31RA/OSMRb dimerization assay;

k. blocks the Cynomolgus IL-31-induced signaling with an $IC_{50}$ of 0.05 to 20 nM, particularly with an $IC_{50}$ of 0.05 to 10 nM, particularly with an $IC_{50}$ of 0.05 to 5 nM, as measured in a Path Hunter IL-31RA/OSMRb dimerization assay;

l. has a melting temperature (Tm), determined by differential scanning fluorimetry, of at least 60° C., preferably of at least 63° C., more preferably of at least 66° C., in particular wherein said multispecific antibody is formulated in 20 mM MES buffer at pH 7.0; and/or m. has a loss in monomer content, after storage for four weeks, of less than 5%, e.g. less than 4%, less than 3%, less than 2%, preferably less than 1%, when said multispecific antibody is at a starting concentration of 100 mg/ml, and in particular wherein said multispecific antibody is formulated in 20 mM acetate buffer at pH 5.5.

35. The multispecific antibody of any one of the preceding items, which is selected from Morrison antibodies having the following heavy chain (HC) and light chain (LC) sequences:
   an HC sequence of SEQ ID NO: 38 and an LC sequence of SEQ ID NO: 37;
   an HC sequence of SEQ ID NO: 40 and an LC sequence of SEQ ID NO: 39;
   an HC sequence of SEQ ID NO: 42 and an LC sequence of SEQ ID NO: 41;
   an HC sequence of SEQ ID NO: 44 and an LC sequence of SEQ ID NO: 43;
   an HC sequence of SEQ ID NO: 46 and an LC sequence of SEQ ID NO: 45;
   an HC sequence of SEQ ID NO: 48 and an LC sequence of SEQ ID NO: 47; and
   an HC sequence of SEQ ID NO: 50 and an LC sequence of SEQ ID NO: 49.
36. A nucleic acid or two nucleic acids encoding the multispecific antibody of any one of items 1 to 35.
37. A vector or two vectors comprising the nucleic acid or two nucleic acids of item 36.
38. A host cell or host cells comprising the vector or the two vectors of item 37.
39. A method for producing the multispecific antibody of any one of items 1 to 35, comprising
   (i) providing the nucleic acid or two nucleic acids of item 36, or the vector or the two vectors of item 37, expressing said nucleic acid or nucleic acids, or said vector or vectors, and collecting said multispecific antibody from the expression system, or (ii) providing a host cell or host cells according to item 38, culturing said host cell or said host cells; and collecting said multispecific antibody from the cell culture.
40. A pharmaceutical composition comprising the multispecific antibody of any one of items 1 to 35 and a pharmaceutically acceptable carrier.
41. The multispecific antibody of any one of items 1 to 35 for use as a medicament.
42. The multispecific antibody of any one of items 1 to 35 for use in the treatment of a disease, particularly a human disease, more particularly a human disease selected from allergic, inflammatory and autoimmune diseases, particularly from inflammatory and autoimmune diseases.
43. The multispecific antibody of any one of items 1 to 35 for use in the treatment of a disease according to item 42, wherein said disease is selected from pruritus-causing allergic diseases, pruritus-causing inflammatory diseases and pruritus-causing autoimmune diseases, particularly from pruritus-causing inflammatory diseases and pruritus-causing autoimmune diseases.
44. The multispecific antibody of item 42 or 43, wherein said disease is selected from atopic dermatitis, acute allergic contact dermatitis, chronic spontaneous urticaria, bullous pemphigoid, alopecia areata, dermatomyositis, prurigo nodularis, psoriasis and atopic asthma; particularly wherein said disease is atopic dermatitis.
45. A method for the treatment of a disease, particularly a human disease, more particularly a human disease selected from allergic, inflammatory and autoimmune diseases, particularly from inflammatory and autoimmune diseases, comprising the step of administering the multispecific antibody of any one of items 1 to 35 to a patient in need thereof.
46. The method of item 45, wherein said disease is selected from pruritus-causing allergic diseases, pruritus-causing inflammatory diseases and pruritus-causing autoimmune diseases, particularly from pruritus-causing inflammatory diseases and pruritus-causing autoimmune diseases.
47. The method of item 45 or 46, wherein said disease is selected from atopic dermatitis, acute allergic contact dermatitis, chronic spontaneous urticaria, bullous pemphigoid, alopecia areata, dermatomyositis, prurigo nodularis, psoriasis and atopic asthma; particularly wherein said disease is atopic dermatitis.
48. A method for the treatment of a disease, more particularly a human disease selected from allergic, inflammatory and autoimmune diseases; particularly from pruritus-causing allergic diseases, pruritus-causing inflammatory diseases and pruritus-causing autoimmune diseases;
   said method comprising the steps of administering to a patient in need thereof
   1. a first antibody comprising
      a) an IL4R-BD, as defined in any of the preceding items 1 to 26 and 32 to 35, and
      b) an Fc region, in particular an IgG region, in particular an IgG4 region; and
   2. a second antibody comprising an IL31-BD, as defined in any of the preceding items 1 to 20 and 27 to 35.
49. The method of item 48, wherein the administration is performed such that an effective dose level of said first antibody and said second antibody is simultaneously reached in the blood plasma of the patient in need thereof.
50. The method of item 48 or 49, wherein said disease is selected from atopic dermatitis, acute allergic contact dermatitis, chronic spontaneous urticaria, bullous pemphigoid, alopecia areata, dermatomyositis, prurigo nodularis, psoriasis and atopic asthma; particularly wherein said disease is atopic dermatitis.
51. A kit comprising
   1. a first antibody comprising
      a) an IL4R-BD, as defined in any of the preceding items 1 to 26 and 32 to 35, and
      b) an Fc region, in particular an IgG region, in particular an IgG4 region; and
   2. a second antibody comprising an IL31-BD, as defined in any of the preceding items 1 to 20 and 27 to 35.
52. The pharmaceutical composition of item 40, wherein said pharmaceutical composition is a therapeutic agent for a human disease selected from allergic, inflammatory and autoimmune diseases.
53. The pharmaceutical composition of item 52, wherein said disease is selected from atopic dermatitis, acute allergic contact dermatitis, chronic spontaneous urticaria, bullous pemphigoid, alopecia areata, dermatomyositis, prurigo nodularis, psoriasis and atopic asthma; particularly wherein said disease is atopic dermatitis.

BRIEF DESCRIPTION OF THE DRAWINGS

FIG. 1 shows the potency of the Morrison-H molecules PRO2198 and PRO2199 to inhibit IL-4R- and IL-31-induced signaling in the BEAS-2B assay compared to a combination of dupilumab and BMS-981164. PRO2198 and PRO2199 show similar potencies to inhibit IL-4R- and IL-31-induced signaling when compared to the combination of dupilumab and BMS-981164 (A). Individual blockage of IL-4R or IL-31 alone by the addition of dupilumab or BMS-981164 alone is less efficacious than the combined blockage of IL-4R- and IL-31-induced signaling (B).

FIG. 3 shows the potency of the optimized anti-IL-4R scFvs PRO1898 and PRO1899 to block human IL-4-induced signaling (A) and human IL-13-induced signaling (B) of IL-4R in a Stat-6 reporter gene assay in HEK-Blue cells. The potency of the analyzed molecules is compared to dupilumab.

FIG. 4 shows the potency of the optimized anti-IL-4R scFvs PRO1898 (A) and PRO1899 (B) to inhibit the interaction between human IL-4 and human IL-4R assessed by competitive ELISA.

FIG. 5 shows the concomitant binding of Morrison antibody PRO2198 to human IL-4R/human IL-31 and to cynomolgus monkey IL-4R/cynomolgus monkey IL-31. Top: schematic representation of the experimental design; Bottom: sensorgram showing concomitant binding of PRO2198 to human IL-4R/human IL-31 (dark grey) and cynomolgus monkey IL-4R/cynomolgus monkey IL-31 (light grey).

FIG. 6 shows the binding of Morrison-H (MorrH) and Morrison-L (MorrH) molecules PRO2198, PRO2199, PRO2206 and PRO2207 and negative control molecule PRO2077 to human IL-4R (A) and to cynomolgus IL-4R (B) on transfected HEK293T cells. All molecules bound to human IL-4R (A). No binding to cynomolgus IL-4R was observed for the control molecule PRO2077 (B). An antibody targeting V5 Tag (V5 Tag), which is fused to the N-terminus of human and cynomolgus IL-4R expression constructs, was used as a positive control for plasma membranous binding.

FIG. 7 shows the potencies of Morrison-H (MorrH) and Morrison-L (MorrL) antibodies PRO2198, PRO2199, PRO2206 and PRO2207 to neutralize human IL-4- and human IL-13-induced signaling in the stat-6 reporter gene assay. The potency of IL-4R blockage by the Morrison-H and Morrison-L antibodies is comparable to dupilumab for both IL-4-induced signaling (A and C) and IL-13-induced signaling (B and D). The $IC_{50}$ values depicted in the FIGS. 5A to 5D represent single point measurements.

FIG. 11 shows the potency of Morrison-H molecules PRO2198 and PRO2199 and corresponding anti-IL-4R IgG4 molecules PRO2209 and PRO2210, which lack IL-31 scFv binding domains, to block IL-4- and IL-13-induced CD23 expression in human PBMCs. PRO2198 and PRO2199 inhibit IL-4- and IL-13-induced CD23 upregulation in human monocytes (A), naïve B cells (B) and memory B cells (C) with similar potency when compared to dupilumab. PRO2209 and PRO2210 show equal inhibition when compared to dupilumab.

DETAILED DESCRIPTION OF THE INVENTION

Figure 2:
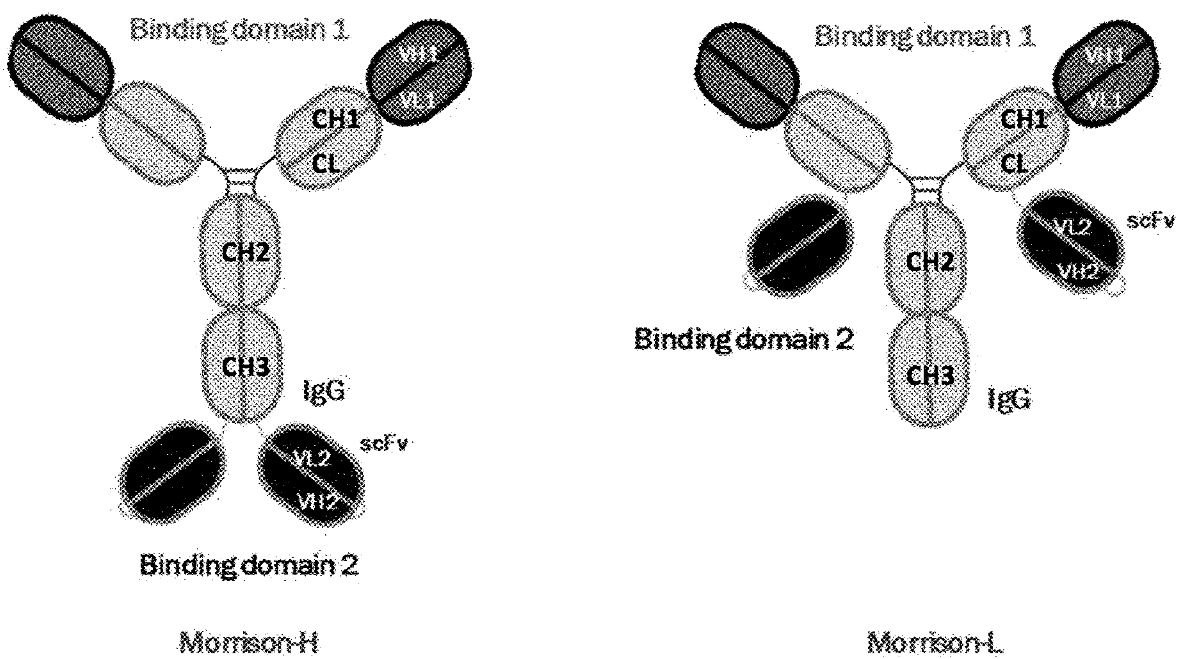
FIG. 2 shows the schematic representation of the IgG4 Morrison-H format (left) and Morrison-L format (right) with labeled subdomain nomenclature. Linker sequences connecting the Fv domains (light grey) consist of ($G_4S$) modules of different repetitions (two modules in between constant regions and scFv domains and 4 modules in between VL2 and VH2).

Known therapeutic anti-IL-4R antibodies often suffer from a lack of efficacy and low to moderate response rates in patients. They also do not directly address itching, which is a common symptom particularly in skin-associated inflammatory and autoimmune disorders. There is thus a need in the medical field for improved anti-IL-4R antibody-based therapeutics, which have higher efficacy for allergic, inflammatory and autoimmune diseases, in particular for pruritus-causing inflammatory and autoimmune diseases, such as moderate to severe atopic dermatitis, and at the same time are able to potently reduce disease-related itching.

The present invention provides multispecific antibodies comprising one or two binding domains, which specifically bind to IL-4R (IL4R-BD), and one or two binding domains, which specifically bind to IL-31 (IL31-BD), wherein the multispecific antibody comprises an immunoglobulin Fc region. The multispecific antibodies of the present invention can simultaneously block IL-4/IL-13 as well as IL-31-induced signaling in a highly efficient manner.

It is believed by the inventors that the immunoglobulin Fc region provides additional FcγR interactions that enhance the binding of the multispecific antibodies of the invention to IL-4R on living cells, and thereby increasing their potency to block IL-4R-mediated signaling. The analysis of different antibody formats in a human PBMC assay further indicates that the interaction of the Fc region with Fc gamma receptor type II (FcγRII) seems to be of particular importance for the observed potency increase. Thus, in the context of the present invention, the term "functional Fc region" refers to an Fc region that is able to interact with FcγR, in particular with FcγRII, within the range of its natural functionality.

According to the best knowledge of the inventors, the simultaneous blockage of both the IL-4R signaling pathway and the IL-31 signaling pathway has not yet been reported in the prior art, let alone the highly efficient simultaneous blockage of said pathways by a single molecule.

Interleukin 31 (IL-31) is an inflammatory cytokine that helps trigger cell-mediated immunity against pathogens. IL-31 is preferentially produced by Th2-cells. IL-31 sends signals through a heterodimeric receptor complex (IL-31R or IL31R) comprising the interleukin 31 receptor alpha (IL-31RA or IL31RA) and the oncostatin M receptor p (OSMR R), expressed in immune and epithelial cells. Binding of IL-31 to this receptor complex results in activation of the JAK/STAT and PI3K/AKT signal transduction pathways, and also activates different MAPK pathways (ERK, p38, and JNK).

IL-31 is implicated in various chronic inflammatory diseases. For example, it has been found that IL-31 overexpression in mice results in dermatitis-like symptoms, see, Dillon, et al, Nature Immunol. 5:752-760, (2004). Furthermore, in many chronic inflammatory diseases, such as for example in AD, IL-31 mediates activation of nerve fibers within the skin of the patients resulting in an aggressive itch-phenotype, which exacerbates the symptoms of these diseases upon patient scratching, see for example Oetjen et al., Cell, 171: 217-228 (2017). Scratching can lead to skin barrier disruption, access of microbial pathogens into the skin and further promotes inflammation at the site.

Also, it has been found that IL-31 is implicated in allergic asthma, allergic rhinitis, inflammatory bowel diseases, malignancies and osteoporosis, see Bagci et al., J Allergy Clin Immunol, 141(3):858-866 (2018).

Blockage of IL-31/IL-31RA signaling by anti-IL31RA antibodies, such as for example by the anti-IL-31RA antibody nemolizumab, is clinically proven to be effective at reducing itch in patients suffering from AD, see Ruzicka et al., N Engl J Med, 376:2092-2093 (2017).

Furthermore, the IL-31-neutralizing antibody BMS-981164 was developed to provide an effective targeted therapy for the treatment of chronic pruritic skin conditions, see Lewis et al, J Eur Acad of Dermatol Venereol, 31(1): 142-150 (2017).

Besides targeting IL-4R (first specificity), it was decided to target IL-31 (second specificity) and not the cell-bound IL-31RA, to avoid any potential cross linkage between cells, which might well happen when targeting two different types of receptors on a cell surface simultaneously (e.g. IL-4R and IL-31RA).

As stated above, the multispecific antibodies of the present invention can simultaneously block IL-4-/IL-13- as well as IL-31-induced signaling in a very efficient manner. For example, at a concentration of 1 μg/ml, PRO2198 and PRO2199, two representative examples of the multispecific antibodies of the present invention, are able to reduce the combined IL-4R- and IL-31-mediated CCL2 secretion of BEAS-2B cells, that have been treated with 1 ng/ml IL-4 and 10 ng/ml IL-31, at least to a similar extent when compared to an equivalent amount of a 1:1 mixture of the anti-IL-4R antibody dupilumab and the anti-IL-31 antibody BMS-981164 (FIG. 1B).

The chemokine (C—C motif) ligand 2 (CCL2), also referred to as monocyte chemoattractant protein 1 (MCP1) and small inducible cytokine A2, is a small cytokine that belongs to the CC chemokine family. CCL2 recruits monocytes, memory T cells, and dendritic cells to the sites of inflammation produced by either tissue injury or infection. CCL2 is implicated in pathogeneses of several diseases characterized by monocytic infiltrates, such as psoriasis, rheumatoid arthritis and atherosclerosis (Xia et al, Expert Opinion on Therapeutic Patents, 2009, 19 (3): 295-303).

Some of the multispecific antibodies of the present invention, e.g. PRO2198, are able to reduce the combined IL-4R- and IL-31-mediated CCL2 secretion of said BEAS-2B cells stronger than an equivalent amount of such a 1:1 mixture of dupilumab and BMS-981164 and almost to the level of untreated BEAS-2B cells (FIG. 1B).

The term "BEAS-2B cells" or BEAS-2B", as used herein, refers to cells of an immortalized non-tumorigenic epithelial cell line from human bronchial epithelium. This cell line has been established via transfection with an adenovirus 12-SV40 hybrid virus and subsequent immortalization via consecutive cell passaging, see Reddel et al., Cancer Res., 48(7):1904-1909 (1988). BEAS-2B cells have been widely used to study cellular and molecular mechanisms in lung related diseases and as an in vitro cell model for lung-related toxicology studies.

In addition, the anti-IL-4R×IL-31 multispecific antibodies of the present invention exhibit very advantageous biophysical properties, in particular an outstanding formulation and storage stability at antibody concentrations well above 100 mg/ml. For example, the loss of the protein content as well as of the monomeric content for PRO2198, a representative multispecific antibody of the present invention, is less than 1% when stored for four months at 4° C. at a concentration above 100 mg/ml in 20 mM acetate buffer (pH 5.5).

The multispecific antibodies of the present invention thus provide distinct therapeutic advantages over conventional therapies.

Unless defined otherwise, all technical and scientific terms used herein have the same meaning as commonly understood by those of ordinary skill in the art to which this invention pertains.

The terms "comprising" and "including" are used herein in their open-ended and non-limiting sense unless otherwise noted. With respect to such latter embodiments, the term "comprising" thus includes the narrower term "consisting of".

The terms "a" and "an" and "the" and similar references in the context of describing the invention (especially in the context of the following claims) are to be construed to cover both the singular and the plural, unless otherwise indicated herein or clearly contradicted by context. For example, the term "a cell" includes a plurality of cells, including mixtures thereof. Where the plural form is used for compounds, salts, and the like, this is taken to mean also a single compound, salt, or the like.

In one aspect, the present invention relates to a multispecific antibody comprising:

a) one or two binding domains, which specifically bind to IL-4R (IL4R-BD), and b) one or two binding domains, which specifically bind to IL-31 (IL31-BD), wherein the multispecific antibody comprises an immunoglobulin Fc region.

The term "antibody" and the like, as used herein, includes whole antibodies or single chains thereof; and any antigen-binding fragment (i.e., "antigen-binding portion") or single chains thereof; and molecules comprising antibody CDRs, VH regions or VL regions (including without limitation multispecific antibodies). A naturally occurring "whole antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDRs), flanked by regions that are more conserved, termed framework regions (FRs). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The term "immunoglobulin Fc region" or "Fc region", as used herein, is used to define a C-terminal region of an immunoglobulin heavy chain, i.e. the CH2 and CH3 domains of the heavy chain constant regions. The term "Fc region" includes native-sequence Fc regions and variant Fc regions, i.e. Fc regions that are engineered to exhibit certain desired properties, such as for example altered Fc receptor binding function and/or reduced or suppressed Fab arm exchange. An example of such an engineered Fc region is the knob-into-hole (KiH) technology (see for example Ridgway et al., Protein Eng. 9:617-21 (1996) and Spiess et al., J Biol Chem. 288(37):26583-93 (2013)). Native-sequence Fc regions include human IgG1, IgG2 (IgG2A, IgG2B), IgG3 and IgG4. "Fc receptor" or "FcR" describes a receptor that binds to the Fc region of an antibody. Particularly, the FcR is a native sequence human FcR, which binds an IgG antibody (a gamma receptor) and includes receptors of the FcγRI, FcγRII, and FcγRIII subclasses, including allelic variants and alternatively spliced forms of these receptors, FcγRII receptors including FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see M. Daeron, Annu. Rev. Immunol. 5:203-234 (1997). FcRs are reviewed in Ravetch and Kinet, Annu. Rev. Immunol. 9: 457-92 (1991); Capet et al, Immunomethods 4: 25-34 (1994); and de Haas et al, J. Lab. Clin. Med. 126: 330-41 (1995). Other FcRs, including those to be identified in the future, are encompassed by the term "FcR" herein. The term "Fc receptor" or "FcR" also includes the neonatal receptor, FcRn, which is responsible for the transfer of maternal IgGs to the fetus. Guyer et al., J. Immunol. 117: 587 (1976) and Kim et al., J. Immunol. 24: 249 (1994). Methods of measuring binding to FcRn are known (see, e.g., Ghetie and Ward, Immunol. Today 18: (12): 592-8 (1997); Ghetie et al., Nature Biotechnology 15 (7): 637-40 (1997); Hinton et al., J. Biol. Chem. TJI (8): 6213-6 (2004); WO 2004/92219 (Hinton et al). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., J. Biol. Chem. 9(2): 6591-6604 (2001).

In particular embodiments, the immunoglobulin Fc region comprised in the multispecific antibodies of the invention is selected from an Fc region of an IgG subclass, particularly from an Fc region of the IgG subclasses IgG1 and IgG4, particularly from an Fc region of IgG4.

In particular embodiments, the multispecific antibodies of the invention comprise an IgG region.

The term "IgG region", as used herein, refers to the heavy and light chain of an immunoglobulin G, i.e. the Fc region, as defined above, and the Fab region, consisting of the VL, VH, CL and CH1 domains. The term "IgG region" includes native-sequence IgG regions, such as human IgG1, IgG2 (IgG2A, IgG2B), IgG3 and IgG4, as well as engineered IgG regions, which exhibit certain desired properties, as for example the properties defined above for the Fc region. The term "functional IgG region", as used herein, refers to an IgG region comprising a functional Fc region.

In particular embodiments, the multispecific antibodies of the invention comprise an IgG region, wherein the IgG region is selected from the IgG subclasses IgG1 and IgG4, in particular from IgG4.

The terms "binding domain", "antigen-binding fragment thereof", "antigen-binding portion" of an antibody, and the like, as used herein, refer to one or more fragments of an intact antibody that retain the ability to specifically bind to a given antigen (e.g., IL4R, IL-31). Antigen-binding functions of an antibody can be performed by fragments of an intact antibody. Specifically, in case of the multispecific antibodies of the present invention, the terms "binding domain", "antigen-binding fragment thereof", "antigen-binding portion", and the like, as used herein, refer to a Fab fragment, i.e. a monovalent fragment consisting of the VL, VH, CL and CH1 domains; a $F(ab)_2$ fragment, i.e. a bivalent fragment comprising two Fab fragments linked by a disulfide bridge at the hinge region; an Fv fragment consisting of the VL and VH domains of a single arm of an antibody; a disulfide stabilized Fv fragment (dsFv); and a single chain Fv fragment (scFV). Preferably, the binding domains of the antibodies of the present invention are independently of each other selected from a Fab fragment, an Fv fragment, a dsFv fragment and a single-chain Fv fragment (scFv). In particular embodiments, the binding domains of the antibodies of the present invention are independently of each other selected from a Fab fragment and a single-chain Fv fragment (scFv). In other particular embodiments, the VL and VH domains of the scFv fragment are stabilized by an interdomain disulfide bond, in particular said VH domain comprises a single cysteine residue in position 51 (AHo numbering) and said VL domain comprises a single cysteine residue in position 141 (AHo numbering).

The term "Complementarity Determining Regions" ("CDRs") refers to amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); AI-Lazikani et al., (1997) JMB 273, 927-948 ("Chothia" numbering scheme); ImMunoGenTics (IMGT) numbering (Lefranc, M.-P., The Immunologist, 7, 132-136 (1999); Lefranc, M.-P. et al., Dev. Comp. Immunol., 27, 55-77 (2003)) ("IMGT" numbering scheme); and the numbering scheme described in Honegger & Plückthun, J. Mol. Biol. 309 (2001) 657-670 ("AHo" numbering). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 24-34 (LCDR1), 50-56 (LCDR2), and 89-97 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (HCDR1), 51-57 (HCDR2) and 93-102 (HCDR3), and the CDR amino acid residues in the VL are numbered approximately 27-32 (LCDR1), 50-52 (LCDR2), and 89-97 (LCDR3) (numbering according to "Kabat"). Under IMGT, the CDRs of an antibody can be determined using the program IMGT/DomainGap Align.

In the context of the present invention, the numbering system suggested by Honegger & Plückthun ("AHo") is used (Honegger & Plückthun, J. Mol. Biol. 309 (2001) 657-670), unless specifically mentioned otherwise. In particular, the following residues are defined as CDRs according to AHo numbering scheme: LCDR1 (also referred to as CDR-L1): L24-L42; LCDR2 (also referred to as CDR-L2): L58-L72; LCDR3 (also referred to as CDR-L3): L107-L138; HCDR1 (also referred to as CDR-H1): H27-H42; HCDR2 (also referred to as CDR-H2): H57-H76; HCDR3 (also referred to as CDR-H3): H108-H138. For the sake of clarity, the numbering system according to Honegger & Plückthun takes the length diversity into account that is found in naturally occurring antibodies, both in the different VH and VL subfamilies and, in particular, in the CDRs, and provides for gaps in the sequences. Thus, in a given antibody variable domain usually not all positions 1 to 149 will be occupied by an amino acid residue.

The term "binding specificity" as used herein refers to the ability of an individual antibody to react with one antigenic determinant and not with a different antigenic determinant. As used herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In its most general form (and when no defined reference is mentioned), "specific binding" is referring to the ability of the antibody to discriminate between the target of interest and an unrelated molecule, as determined, for example, in accordance with specificity assay methods known in the art. Such methods comprise, but are not limited to Western blots, ELISA, RIA, ECL, IRMA, SPR (Surface plasmon resonance) tests and peptide scans. For example, a standard ELISA assay can be carried out. The scoring may be carried out by standard color development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. In a further example, an SPR assay can be carried out, wherein at least 10-fold, particularly at least 100-fold difference between a background and signal indicates on specific binding. Typically, determination of binding specificity is performed by using not a single reference molecule, but a set of about three to five unrelated molecules, such as milk powder, transferrin or the like.

Suitably, the antibodies of the invention are isolated antibodies. The term "isolated antibody", as used herein, refers to an antibody that is substantially free of other antibodies having different antigenic specificities (e.g., an isolated antibody that specifically binds IL-4R and IL-31 is substantially free of antibodies that specifically bind antigens other than IL-4R and IL-31. Moreover, an isolated antibody may be substantially free of other cellular material and/or chemicals.

Suitably, the antibodies of the invention are monoclonal antibodies. The term "monoclonal antibody" as used herein refers to antibodies that have substantially identical amino acid sequences or are derived from the same genetic source. A monoclonal antibody displays a binding specificity and affinity for a particular epitope, or binding specificities and affinities for specific epitopes.

Antibodies of the invention include, but are not limited to, chimeric, human and humanized antibodies.

The term "chimeric antibody" (or antigen-binding fragment thereof), as used herein, refers to an antibody molecule (or antigen-binding fragment thereof) in which (a) the constant region, or a portion thereof, is altered, replaced or exchanged so that the antigen-binding site (variable region) is linked to a constant region of a different or altered class, effector function and/or species; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "humanized" antibody (or antigen-binding fragment thereof), as used herein, refers to an antibody (or antigen-binding fragment thereof) that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). Additional framework region modifications may be made within the human framework sequences as well as within the CDR sequences derived from the germline of another mammalian species. The humanized antibodies of the invention may include amino acid residues not encoded by human sequences (e.g., mutations introduced by random or site-specific mutagenesis in vitro or by somatic mutation in vivo, or a conservative substitution to promote stability or manufacturing). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239: 1534-1536, 1988; Padlan, Molec. Immun., 28:489-498, 1991; and Padlan, Molec. Immun., 31: 169-217, 1994. Other examples of human engineering technology include but are not limited to the Xoma technology disclosed in U.S. Pat. No. 5,766,886.

The term "recombinant humanized antibody" as used herein, includes all human antibodies that are prepared, expressed, created or isolated by recombinant means, such as antibodies isolated from a host cell transformed to express the humanized antibody, e.g., from a transfectoma, and antibodies prepared, expressed, created or isolated by any other means that involve splicing of all or a portion of a human immunoglobulin gene, sequences to other DNA sequences.

Preferably, the multispecific antibodies of the invention are humanized. More preferably, the multispecific antibodies of the invention are humanized and comprises rabbit derived CDRs.

The term "multispecific antibody" as used herein, refers to an antibody that binds to two or more different epitopes on at least two or more different targets (e.g., IL-4R and IL-31). Preferably, the multispecific antibodies of the invention are bispecific. The term "bispecific antibody" as used herein, refers to an antibody that binds to at least two different epitopes on two different targets (e.g., IL-4R and IL-31).

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. "Conformational" and "linear" epitopes are distinguished in that the binding to the former but not the latter is lost in the presence of denaturing solvents.

The term "conformational epitope" as used herein refers to amino acid residues of an antigen that come together on the surface when the polypeptide chain folds to form the native protein.

The term "linear epitope" refers to an epitope, wherein all points of interaction between the protein and the interacting molecule (such as an antibody) occurring linearly along the primary amino acid sequence of the protein (continuous).

The term "recognize" as used herein refers to an antibody antigen-binding fragment thereof that finds and interacts (e.g., binds) with its conformational epitope.

The term "avidity" as used herein refers to an informative measure of the overall stability or strength of the antibody-antigen complex. It is controlled by three major factors: antibody epitope affinity; the valency of both the antigen and antibody; and the structural arrangement of the interacting parts. Ultimately these factors define the specificity of the antibody, that is, the likelihood that the particular antibody is binding to a precise antigen epitope.

Suitably, the multispecific antibodies of the invention comprise one or two IL4R-BDs. Particularly, the multispecific antibodies of the invention comprise two IL4R-BDs.

The term "IL-4R" refers in particular to human IL-4R with UniProt ID number P24394. Suitably, the IL4R-BD of the present invention targets IL-4R, in particular human IL-4R. Particularly, the multispecific antibodies of the invention comprises one or two IL4R-BDs that target human and Cynomolgus (*Macaca fascicularis*) IL-4R. More particularly, the multispecific antibody of the invention comprises one or two IL4R-BDs that targets human, Cynomolgus (*Macaca fascicularis*) and Marmoset (Callithrix jacchus) IL-4R.

Suitably, the IL4R-BDs are characterized by one or more of the following parameters:

a. bind to human IL-4R with a monovalent dissociation constant ($K_D$) of 0.1 to 200 pM, particularly with a $K_D$ of 0.1 to 100 pM, particularly of 0.1 to 50 pM, as measured by surface plasmon resonance (SPR), particularly wherein said IL4R-BDs are in an scFv format;
b. are cross-reactive with *Macaca fascicularis* (Cynomolgus) IL4R, in particular bind to in particular bind to Cynomolgus IL-4R with a monovalent $K_D$ of 1 pM to 5 nM, particularly of 1 pM to 3 nM, particularly of 1 pM to 2 nM, as measured by SPR, particularly wherein said IL4R-BDs are in an scFv format;
c. are cross-reactive with Callithrix jacchus (Marmoset) IL-4R, in particular bind to Marmoset IL-4R with a monovalent $K_D$ of 1 pM to 5 nM, particularly of 1 pM to 3 nM, particularly of 1 pM to 2 nM, as measured by SPR, particularly wherein said IL4R-BDs are in an scFv format;
d. neutralize the human IL-4-induced signaling with an $IC_{50}$ of 0.01 to 5 ng/ml, particularly with an $IC_{50}$ of 0.01 to 3 ng/ml, particularly with an $IC_{50}$ of 0.01 to 1.5 ng/ml, as measured in a stat6 reporter gene assay in HEK-Blue cells, wherein said IL4R-BDs are in an scFv format;
e. neutralize the human IL-13-induced signaling with an $IC_{50}$ of 0.01 to 10 ng/ml, particularly with an $IC_{50}$ of 0.01 to 5 ng/ml, particularly with an $IC_{50}$ of 0.01 to 2.5 ng/ml, as measured in a stat-6 reporter gene assay in HEK-Blue cells, wherein said IL4R-BDs are in an scFv format; and/or
f. inhibit the binding of human IL-4 to human IL-4R with an $IC_{50}$ of 0.01 to 10 ng/ml, particularly with an $IC_{50}$ of 0.01 to 5 ng/ml, particularly with an $IC_{50}$ of 0.01 to 2 ng/ml, as measured in a competition ELISA, wherein said IL4R-BDs are in an scFv format.

The term "HEK-Blue cells" or "HEK-Blue", as used herein, refers to commercially available human embryonic kidney cells that are transfected with and stably express an optimized secreted embryonic alkaline phosphatase (SEAP) reporter gene under the control of a promoter inducible by NF-κB transcription factor. The level of SEAP protein released into the culture media is typically used as a measure of NF-κB activation.

As used herein, the term "affinity" refers to the strength of interaction between the antibody and the antigen at single antigenic sites. Within each antigenic site, the variable region of the antibody "arm" interacts through weak non-covalent forces with antigen at numerous sites; the more interactions, the stronger the affinity.

"Binding affinity" generally refers to the strength of the total sum of non-covalent interactions between a single binding site of a molecule (e.g., of an antibody) and its binding partner (e.g., an antigen or, more specifically, an epitope on an antigen). Unless indicated otherwise, as used herein, "binding affinity", "bind to", "binds to" or "binding to" refers to intrinsic binding affinity that reflects a 1:1 interaction between members of a binding pair (e.g., an antibody fragment and an antigen). The affinity of a molecule X for its partner Y can generally be represented by the dissociation constant ($K_D$). Affinity can be measured by common methods known in the art, including those described herein. Low-affinity antibodies generally bind antigens slowly and tend to dissociate readily, whereas high-affinity antibodies generally bind antigens faster and tend to remain bound longer. A variety of methods of measuring binding affinity are known in the art, any of which can be used for purposes of the present invention. Specific illustrative and exemplary embodiments for measuring binding affinity, i.e. binding strength are described in the following.

The term "$K_{assoc}$", "$K_a$" or "$K_{on}$", as used herein, are intended to refer to the association rate of a particular antibody-antigen interaction, whereas the term "$K_{dis}$", "$K_d$" or "$K_{off}$", as used herein, is intended to refer to the dissociation rate of a particular antibody-antigen interaction. In one embodiment, the term "$K_D$", as used herein, is intended to refer to the dissociation constant, which is obtained from the ratio of $K_d$ to $K_a$ (i.e. $K_d/K_a$) and is expressed as a molar concentration (M). The "$K_D$" or "$K_D$ value" or "$K_D$" or "$K_D$ value" according to this invention is in one embodiment measured by using surface plasmon resonance assays.

Affinity to recombinant human IL-4R, recombinant Cynomolgus IL-4R and recombinant Marmoset IL-4R is determined by surface plasmon resonance (SPR) measurements, as described in the paragraphs [0187] and [0188](scFvs) and [0265](multispecific molecules). Affinity to recombinant human IL-31, recombinant Cynomolgus IL-31 and recombinant Marmoset IL-31 is determined by surface plasmon resonance (SPR) measurements, as described in the paragraphs [0209](scFvs) and [0267] (multispecific molecules).

Suitably, the multispecific antibody of the invention acts as an antagonist of IL4R. In other words, the IL4R-BD of the multispecific antibody of the invention is an inhibitor of IL-4R signaling. The term "blocker" or "inhibitor" or "antagonist", as used herein, refers to an antibody or binding domain thereof that inhibits or reduces a biological activity of the antigen it binds to. The IL4R-BDs of the multispecific antibody of the invention bind to the IL-4R, thereby blocking the binding of IL-4 to IL4R, in particular the binding of both IL-4 and IL-13 to IL-4R, which leads to reduced IL-4R function.

Suitably, the IL4R-BDs of the multispecific antibody of the present invention are further characterized by one or more of the following parameters:

g. when being in scFv format, has a melting temperature (Tm), determined by differential scanning fluorimetry (DSF), of at least 63° C., particularly of at least 65° C., particularly of at least 67° C., particularly of at least 69° C., particularly of at least 70° C., particularly of at least 71° C., particularly of at least 72° C., in particular wherein said scFvs are formulated in 50 mM phosphate citrate buffer with 150 mM NaCl at pH 6.4;

h. when being in scFv format, has a loss in monomer content, after storage for four weeks at 4° C. of less than 5%, when said scFvs are at a starting concentration of 10 mg/ml, and in particular wherein said scFvs are formulated in 50 mM phosphate citrate buffer with 150 mM NaCl at pH 6.4; and/or i. when being in scFv format, has a loss in monomer content, after 5 freeze-thawing cycles, of less than 5%, e.g. less than 4%, less than 3%, preferably less than 2%, when said scFvs are at a starting concentration of 10 mg/ml, and in particular wherein said scFvs are formulated in 50 mM phosphate citrate buffer with 150 mM NaCl at pH 6.4.

DSF is described earlier (Egan, et al., MAbs, 9(1) (2017), 68-84; Niesen, et al., Nature Protocols, 2(9) (2007) 2212-2221). The midpoint of transition for the thermal unfolding of the scFv constructs is determined by Differential Scanning Fluorimetry using the fluorescence dye SYPRO® Orange (see Wong & Raleigh, Protein Science 25 (2016) 1834-1840). Samples in phosphate-citrate buffer at pH 6.4 are prepared at a final protein concentration of 50 μg/ml and containing a final concentration of 5×SYPRO® Orange in a total volume of 100 μl. Twenty-five microliters of prepared samples are added in triplicate to white-walled AB gene PCR plates. The assay is performed in a qPCR machine used as a thermal cycler, and the fluorescence emission is detected using the software's custom dye calibration routine. The PCR plate containing the test samples is subjected to a temperature ramp from 25° C. to 96° C. in increments of 1° C. with 30 s pauses after each temperature increment. The total assay time is about 2 h. The Tm is calculated by the software GraphPad Prism using a mathematical second derivative method to calculate the inflection point of the curve. The reported Tm is an average of three measurements.

The loss in monomer content is as determined by area under the curve calculation of SE-HPLC chromatograms. SE-HPLC is a separation technique based on a solid stationary phase and a liquid mobile phase as outlined by the US Pharmacopeia (USP), chapter 621. This method separates molecules based on their size and shape utilizing a hydrophobic stationary phase and aqueous mobile phase. The separation of molecules is occurring between the void volume ($V_0$) and the total permeation volume ($V_T$) of a specific column. Measurements by SE-HPLC are performed on a Chromaster HPLC system (Hitachi High-Technologies Corporation) equipped with automated sample injection and a UV detector set to the detection wavelength of 280 nm. The equipment is controlled by the software EZChrom Elite (Agilent Technologies, Version 3.3.2 SP2) which also supports analysis of resulting chromatograms. Protein samples are cleared by centrifugation and kept at a temperature of 4-6° C. in the autosampler prior to injection. For the analysis of scFv samples the column Shodex KW403-4F (Showa Denko Inc., #F6989202) is employed with a standardized buffered saline mobile phase (50 mM sodium-phosphate pH 6.5, 300 mM sodium chloride) at the recommended flow rate of 0.35 ml/min. The target sample load per injection is 5 pg. Samples are detected by an UV detector at a wavelength of 280 nm and the data recorded by a suitable software suite. The resulting chromatograms are analyzed in the range of $V_0$ to $V_T$ thereby excluding matrix associated peaks with >10 min elution time.

Suitably, the IL4R-BDs of the multispecific antibodies of the invention are binding domains provided in the present disclosure. The IL4R-BDs of the multispecific antibodies of the invention include, but are not limited to, the humanized IL4R-BDs whose sequences are listed in Table 1.

Suitably, the multispecific antibodies of the invention comprise one or two IL31-BDs. Particularly, the multispecific antibodies of the invention comprise two IL31-BDs.

The term "IL-31" or "IL31" refers in particular to human IL-31 with UniProt ID number Q6EBC2. Suitably, the IL31-BD of the multispecific antibodies of the invention targets IL-31, in particular human IL31 as shown in UniProt ID number Q6EBC2. Particularly, the multispecific antibodies of the invention comprise one or two IL31-BDs that target human and cynomolgus (*Macaca fascicularis*) IL-31.

Suitably, the IL31-BDs used in the present invention are characterized by one or more of the following parameters:

a. bind to human IL-31 with a monovalent dissociation constant ($K_D$) of 5 nM or less, particularly with a monovalent $K_D$ of 5 pM to 5 nM, particularly of 5 pM to 2 nM, particularly of 5 to 1000 pM, as measured by surface plasmon resonance (SPR), particularly wherein said IL31-BDs are in an scFv;

b. are cross-reactive with *Macaca fascicularis* (Cynomolgus) IL-31, in particular bind to Cynomolgus IL-31 with a monovalent $K_D$ of 5 nM or less, particularly with a monovalent $K_D$ of 5 pM to 5 nM, particularly of 5 pM to 2 nM, particularly of 5 to 1000 pM, as measured by SPR, particularly wherein said IL31-BDs are in an scFv;

c. inhibit the human IL-31-induced signaling with an $IC_{50}$ of 0.1 to 30 ng/ml, particularly with an $IC_{50}$ of 0.1 to 20 ng/ml, particularly with an $IC_{50}$ of 0.1 to 10 ng/ml, as measured in a Path Hunter IL-31RA/OSMRb dimerization assay, wherein said IL31-BDs are in an scFv format; and/or d. block the binding of human IL-31 to human IL-31R with an $IC_{50}$ of 0.1 to 20 ng/ml, particularly with an $IC_{50}$ of 0.1 to 10 ng/ml, particularly with an $IC_{50}$ of 0.1 to 6 ng/ml, as measured in a competition ELISA, wherein said IL31-BDs are in an scFv format.

Suitably, the IL31-BDs of the multispecific antibodies of the present invention are further characterized by one or more of the following parameters:

e. when being in scFv format, have a melting temperature (Tm), determined by differential scanning fluorimetry, of at least 65° C., preferably of at least 67° C., more preferably at least 69° C., in particular wherein said scFvs are formulated in 50 mM phosphate citrate buffer with 150 mM NaCl at pH 6.4;

f. when being in scFv format, have a loss in monomer content, after storage for four weeks at 4° C. of less than 5%, e.g. less than 4%, less than 3%, less than 2%, preferably less than 1%, when said scFvs are at a starting concentration of 10 mg/ml, and in particular wherein said scFvs are formulated in 50 mM phosphate citrate buffer with 150 mM NaCl at pH 6.4;

g. when being in scFv format, have a loss in monomer content, after storage for four weeks at 40° C. of less than 5%, e.g. less than 4%, less than 3%, less than 2%, preferably less than 1%, when said scFvs are at a starting concentration of 10 mg/ml, and in particular wherein said scFvs are formulated in 50 mM phosphate citrate buffer with 150 mM NaCl at pH 6.4;

h. when being in scFv format, have a loss in monomer content, after 3 freeze-thawing cycles, of less than 5%, e.g. less than 4%, less than 3%, less than 2%, preferably less than 1%, when said scFvs are at a starting concentration of 10 mg/ml, and in particular wherein said scFvs are formulated in 50 mM phosphate citrate buffer with 150 mM NaCl at pH 6.4; and/or i. when being in scFv format, have a loss in protein content, after storage for four weeks at 4° C. or 40° C. of less than 5%, e.g. less than 4%, less than 3%, less than 2%, preferably less than 1%, when said scFv is at a starting concentration of 10 mg/ml, and in particular wherein said scFv is formulated in 50 mM phosphate citrate buffer with 150 mM NaCl at pH 6.4.

Suitably, the IL31-BDs of the multispecific antibodies of the invention are binding domains provided in the present disclosure. The IL31-BDs of the multispecific antibodies of the invention include, but are not limited to, the humanized IL31-BDs whose sequences are listed in Table 2.

The term "multivalent antibody" refers to a single binding molecule with more than one valency, where "valency" is described as the number of antigen-binding moieties that binds to epitopes on target molecules. As such, the single binding molecule can bind to more than one binding site on a target molecule and/or to more than one target molecule due to the presence of more than one copy of the corresponding antigen-binding moieties. Examples of multivalent antibodies include, but are not limited to bivalent antibodies, trivalent antibodies, tetravalent antibodies, pentavalent antibodies, hexavalent antibodies, and the like.

The term "monovalent antibody", as used herein, refers to an antibody that binds to a single target molecule, and more specifically to a single epitope on a target molecule. Also, the term "binding domain" or "monovalent binding domain", as used herein, refers to a binding domain that binds to a single epitope on a target molecule.

In particular embodiments, the multispecific antibodies of the invention comprise one IL4R-BD and one IL-31-BD, i.e. the multispecific antibodies of the invention are monovalent for both IL-4R and IL-31 specificity.

In further particular embodiments, the multispecific antibodies of the invention comprise one IL4R-BD and two IL-31-BDs, i.e. the multispecific antibodies of the invention are monovalent for IL-4R specificity and bivalent for IL-31 specificity.

In further particular embodiments, the multispecific antibodies of the invention comprise two IL4R-BDs and one IL-31-BD, i.e. the multispecific antibodies of the invention are bivalent for IL-4R specificity and monovalent for IL-31 specificity.

In preferred embodiments, the multispecific antibodies of the invention comprise two IL4R-BDs and two IL-31-BDs, i.e. the multispecific antibodies of the invention are bivalent for IL-4R specificity and bivalent for IL-31 specificity.

In case the multispecific antibodies of the invention comprise two IL4R-BDs, said two IL4R-BDs either bind the same epitope or different epitopes on the IL-4R target molecule. Preferably, the two IL4R-BDs bind the same epitope on the IL-4R target molecule. Suitably, the multispecific antibody of the present invention comprises two identical IL4R-BDs In case the multispecific antibodies of the invention comprise two IL31-BDs, said two IL31-BDs either bind the same epitope or different epitopes on the IL-31 target molecule. Preferably, the two IL31-BDs bind the same epitope on the IL-31 target molecule. Suitably, the multispecific antibody of the present invention comprises two identical IL31-BDs.

The term "same epitope", as used herein, refers to an individual protein determinant on the protein capable of specific binding to more than one antibody, where that individual protein determinant is identical, i.e. consist of identical chemically active surface groupings of molecules such as amino acids or sugar side chains having identical three-dimensional structural characteristics, as well as identical charge characteristics for each of said antibodies. The term "different epitope", as used herein in connection with a specific protein target, refers to individual protein determinants on the protein, each capable of specific binding to a different antibody, where these individual protein determinants are not identical for the different antibodies, i.e. consist of non-identical chemically active surface groupings of molecules such as amino acids or sugar side chains having different three-dimensional structural characteristics, as well as different charge characteristics. These different epitopes can be overlapping or non-overlapping.

In particular embodiments, the multispecific antibodies of the invention are bispecific and bivalent.

In further particular embodiments, the multispecific antibodies of the invention are bispecific and trivalent.

Preferably, the multispecific antibodies of the invention are bispecific and tetravalent, i.e. bivalent for IL-4R specificity and bivalent for IL-31 specificity.

In a particular aspect, the present invention relates to a multispecific antibody comprising:

a) two binding domains, which specifically bind to IL-4R (IL4R-BD), and b) two binding domains, which specifically bind to IL-31 (IL31-BD), wherein said multispecific antibody comprises an IgG region;

each of said IL4R-BDs comprise the HCDR1 sequence of SEQ ID NO: 1, the HCDR2 sequences of SEQ ID NO: 2, the HCDR3 sequence of SEQ ID NO: 3, the LCDR1 sequence of SEQ ID NO: 7, the LCDR2 sequence of SEQ ID NO: 8, and the LCDR3 sequences of SEQ ID NO: 9; and each of said IL31-BDs comprise
the HCDR1 sequence of SEQ ID NO: 12,
the HCDR2 of sequence of SEQ ID NO: 13,
the HCDR3 sequences of SEQ ID NO: 14,
the LCDR1 sequence of SEQ ID NO: 17 or 18,
the LCDR2 sequence of SEQ ID NO: 19, and
the LCDR3 sequences of SEQ ID NOs: 20.

Other variable domains used in the invention include amino acid sequences that have been mutated, yet have at least 80, 85, 90, 91, 92, 93, 94, 95, 96, 97, 98 or 99 percent identity in the CDR regions with the CDR regions depicted in the sequences described in Tables 1 and 2. Other variable domains used the invention include mutant amino acid sequences wherein no more than 1, 2, 3, 4 or 5 amino acids have been mutated in the CDR regions when compared with the CDR regions depicted in the sequence described in Tables 1 and 2.

Suitably, the VH domains of the binding domains of the multispecific antibodies of the invention belong to the VH3 or the VH4 family. In one embodiment, a binding domain used in the invention comprises a VH domain belonging to the VH3 family. In the context of the present invention, the term "belonging to the VHx family (or the VLx family)" means that the framework sequences FR1 to FR3 show the highest degree of homology to said VHx family (or VLx family, respectively). Examples of VH and VL families are given in Knappik et al., J. Mol. Biol. 296 (2000) 57-86, or in WO 2019/057787. A specific example of a VH domain belonging to the VH3 family is represented by SEQ ID NO: 23, and a specific example of a VH domain belonging to VH4 family is represented by SEQ ID NO: 24. In particular, framework regions FR1 to FR3 taken from SEQ ID NO: 23 belong to the VH3 family (Table 3, regions marked in non-bold). Suitably, a VH belonging to the VH3 family, as used herein, is a VH comprising FR1 to FR3 having at least 85%, particularly at least 90%, more particularly at least 95% sequence identity to FR1 to FR3 of SEQ ID NO: 23. Alternative examples of VH3 and VH4 sequences, and examples of other VHx sequences, may be found in Knappik et al., J. Mol. Biol. 296 (2000) 57-86 or in WO 2019/057787.

Suitably, the VL domains of the binding domains used in the invention comprise: VK frameworks FR1, FR2 and FR3, particularly VK1 or VK3 frameworks, particularly VK1 frameworks FR1 to FR3, and a framework FR4, which is selected from a VK FR4. In the case where said binding domains are in an scFv-format, said binding domains comprise: VK frameworks FR1, FR2 and FR3, particularly VK1 or VK3 frameworks, particularly VK1 frameworks FR1 to FR3, and a framework FR4, which is selected from a VK FR4 and a VA FR4, particularly a VA FR4.

Suitable VK1 frameworks FR1 to FR3 as well as an exemplary VA FR4 are set forth in SEQ ID NO: 25 (Table 3, FR regions are marked in non-bold). Alternative examples of VK1 sequences, and examples of VK2, VK3 or VK4 sequences, may be found in Knappik et al., J. Mol. Biol. 296 (2000) 57-86. Suitable VK1 frameworks FR1 to FR3 comprise the amino acid sequences having at least 70, 80, 90 percent identity to amino acid sequences corresponding to FR1 to FR3 and taken from SEQ ID NO: 25 (Table 3, FR regions are marked in non-bold). Suitable VA FR4 are as set forth in SEQ ID NO: 26 to SEQ ID NO: 32 and in SEQ ID NO: 33 comprising a single cysteine residue, particular in a case where a second single cysteine is present in the corresponding VH chain, particularly in position 51 (AHo numbering) of VH, for the formation of an inter-domain disulfide bond. In one embodiment, the VL domains of the binding domains of the multispecific antibodies of the invention, when being in scFv-format, comprises VA FR4 comprising the amino acid sequence having at least 70, 80, 90 percent identity to an amino acid sequence selected from any of SEQ ID NO: 26 to SEQ ID NO: 33, particularly to SEQ ID NO: 26 or 33.

The binding domains of the multispecific antibodies of the invention comprise a VH domain listed in Tables 1 and 2. Suitably, the binding domains used the invention comprise a VH amino acid sequence listed in one of Tables 1 and 2, wherein no more than 20 amino acids in the framework sequences (i.e., the sequences which are not CDR sequences) have been mutated (wherein a mutation is, as various non-limiting examples, an addition, substitution or deletion). Suitably, the binding domains of the multispecific antibodies of the invention comprise a VH amino acid sequence listed in one of Tables 1 and 2, wherein no more than 15 amino acids, particularly no more than 10 amino acids, particularly no more than 5 amino acids in the framework sequences (i.e., the sequences which are not CDR sequences) have been mutated (wherein a mutation is, as various non-limiting examples, an addition, substitution or deletion). Other binding domains used in the invention include amino acids that have been mutated, yet have at least 80, 85, 90, 91, 92, 93, 94, 95, 96, 97, 98 or 99 percent identity in the VH regions with the VH regions depicted in the corresponding sequences described in one of Tables 1 and 2, including VH domains comprising at least positions 5 to 140 (AHo numbering), particularly at least positions 3 to 145 of one of the sequences shown in Tables 1 and 2.

In particular, the binding domains of the multispecific antibodies of the invention comprise a VL domain listed in one of Tables 1 and 2. Suitably, the binding domains of the multispecific antibodies of the invention comprise a VL amino acid sequence listed in one of Tables 1 and 2, wherein no more than about 20 amino acids in the framework sequences (i.e., the sequences which are not CDR sequences) have been mutated (wherein a mutation is, as various non-limiting examples, an addition, substitution or deletion). Suitably, the binding domains of the multispecific antibodies of the invention comprise a VL amino acid sequence listed in one of Tables 1 and 2, wherein no more than about 15 amino acids, particularly no more than 10 amino acids, particularly no more than 5 amino acids in the framework sequences (i.e., the sequences which are not CDR sequences) have been mutated (wherein a mutation is, as various non-limiting examples, an addition, substitution or deletion). Other binding domains used in the invention include amino acids that have been mutated, yet have at least 80, 85, 90, 91, 92, 93, 94, 95, 96, 97, 98 or 99 percent identity in the VL regions with a VL region depicted in the sequences described in Tables 1 and 2, including VL domains comprising at least positions 5 to 140 (AHo numbering), particularly at least positions 3 to 145 of one of the sequences shown in Tables 1 and 2.

In the context of the present invention, the term "binding domain used in the present invention" relates to a binding domain as such, i.e. independent of a multispecific context, and, in particular, to a binding domain comprised in a multispecific construct, e.g. one of the binding domains comprised in a bispecific, trispecific or tetraspecific construct.

Suitably, the binding domains of the multispecific antibodies of the invention are selected from the group consisting of: a Fab, an Fv, a dsFv and an scFv.

Suitably, the binding domains of the multispecific antibodies of the invention are operably linked. The binding domains of the multispecific antibodies of the invention are capable of binding to their respective antigens or receptors simultaneously. The term "simultaneously", as used in this connection refers to the simultaneous binding of at least one of the IL4R-BDs and at least one of the IL31-BDs.

The multispecific antibodies of the present invention comprising one or two IL4R-BDs and one or two IL31-BDs, wherein said one or two IL4R-BDs, and said one or two IL31-BDs are operably linked to each other.

The term "operably linked", as used herein, indicates that two molecules (e.g., polypeptides, domains, binding domains) are attached in a way that each molecule retains functional activity. Two molecules can be "operably linked" whether they are attached directly or indirectly (e.g., via a linker, via a moiety, via a linker to a moiety). The term "linker" refers to a peptide or other moiety that is optionally located between binding domains or antibody fragments used in the invention. A number of strategies may be used to covalently link molecules together. These include, but are not limited to, polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility.

In the context of the present invention, the term "polypeptide linker" refers to a linker consisting of a chain of amino acid residues linked by peptide bonds that is connecting two domains, each being attached to one end of the linker. The polypeptide linker should have a length that is adequate to link two molecules in such a way that they assume the correct conformation relative to one another so that they retain the desired activity. In particular embodiments, the polypeptide linker has a continuous chain of between 2 and 30 amino acid residues (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues). In addition, the amino acid residues selected for inclusion in the polypeptide linker should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. In particular embodiments, the polypeptide linker is non-structured polypeptide. Useful linkers include glycine-serine, or GS linkers. By "Gly-Ser" or "GS" linkers is meant a polymer of glycines and serines in series (including, for example, $(Gly-Ser)_n$, $(GSGGS)_n$ $(GGGGS)_n$ and $(GGGS)_n$, where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since oligopeptides comprising these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single-chain antibodies.

In one group of embodiments, the multispecific antibody of the invention is in a format selected from $(scFv)_2$-Fc-$(scFv)_2$ fusion (ADAPTIR); DVD-Ig; a DART™ and a TRIDENT™. The term "DART™" refers to an antibody format developed by MacroGenics that comprises an immunoglobulin Fc region polypeptide and one or two bispecific Fv binding domains fused to the N-terminus of one heavy chain of the Fc region or to both N-termini of the heavy chains of the Fc region. The term "TRIDENT™" refers to an antibody format developed by MacroGenics that comprises an immunoglobulin Fc region polypeptide, one bispecific Fv binding domain and one Fab fragment. Both the bispecific Fv binding domain and the Fab fragment are fused to the respective N-termini of the two heavy chains of the Fc region polypeptide.

In another group of embodiments, the format of the multispecific antibodies of the present invention is selected from bivalent bispecific IgG formats, trivalent bispecific IgG formats and tetravalent bispecific IgG formats. In particular, the format of said multispecific antibodies is selected from KiH-based IgGs, such as DuoBodies (bispecific IgGs prepared by the Duobody technology) (MAbs. 2017 February/March; 9(2):182-212. doi: 10.1080/19420862.2016.1268307); DVD-Ig; IgG-scFv fusions, such as CODV-IgG, Morrison (IgG $CH_3$-scFv fusion (Morrison-H) or IgG CL-scFv fusion (Morrison-L)), bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain) and Ts2Ab (dsscFv linked to C-terminus of heavy chain). More particularly, the format of said multispecific antibody is selected from KiH-based IgGs, such as DuoBodies; DVD-Ig; CODV-IgG and Morrison (IgG $CH_3$-scFv fusion (Morrison-H) or IgG CL-scFv fusion (Morrison-L)), even more particularly from DVD-Ig and Morrison (IgG $CH_3$-scFv fusion (Morrison-H) or IgG CL-scFv fusion (Morrison-L)).

In particular embodiments of the invention, the format of said multispecific antibodies is selected from Morrison formats, i.e. a Morrison-L and a Morrison-H format. The Morrison-L and Morrison-H formats used in the present invention are tetravalent and bispecific molecular formats bearing an IgG Fc region, in particular an IgG4 Fc region. Two highly stable scFv binding domains, wherein the light chain comprises $V_\kappa$ FR1 to FR3 in combination with a Vλ FR4 (λ-cap), herein also called λ-cap scFv, are fused via a linker L1 to the heavy chain (Morrison-H) or light chain (Morrison-L) C-termini (see FIG. 2).

The linker L1 is a peptide of 2-30 amino acids, more particularly 5-25 amino acids, and most particularly 10-20 amino acids. In particular embodiments, said linker L1 comprises one or more units of four (4) glycine amino acid residues and one (1) serine amino acid residue $(GGGGS)_n$, wherein n=1, 2, 3, 4 or 5, particularly n=2.

In a special embodiment of the invention, the multispecific antibodies have a Morrison-L format, as defined above. In another special embodiment of the invention, the multispecific antibodies have a Morrison-H format, as defined above.

The scFv domains of the multispecific antibodies of the invention comprise a variable heavy chain domain (VH) and a variable light chain domain (VL) connected by a linker L2.

The linker L2 is a peptide of 10-40 amino acids, more particularly 15-30 amino acids, and most particularly 20-25 amino acids. In particular embodiments, said linker L2 comprises one or more units of four (4) glycine amino acid residues and one (1) serine amino acid residue $(GGGGS)_n$, wherein n=1, 2, 3, 4, 5, 6, 7 or 8, particularly n=4.

Specific but non-limiting examples the multispecific antibodies of the invention are the Morrison-L antibodies PRO2206, PRO2207, PRO2208 and the Morrison-H antibodies PRO2198, PRO2199, PRO2200, PRO2201, whose sequences are listed in table 4.

The multispecific antibodies of the invention can be produced using any convenient antibody-manufacturing method known in the art (see, e.g., Fischer, N. & Leger, O., Pathobiology 74 (2007) 3-14 with regard to the production of bispecific constructs; Hornig, N. & Farber-Schwarz, A., Methods Mol. Biol. 907 (2012)713-727, and WO 99/57150 with regard to bispecific diabodies and tandem scFvs). Specific examples of suitable methods for the preparation of the bispecific construct further include, inter alia, the Genmab (see Labrijn et al., Proc. Natl. Acad. Sci. USA 110 (2013) 5145-5150) and Merus (see de Kruif et al., Biotechnol. Bioeng. 106 (2010) 741-750) technologies. Methods for production of bispecific antibodies comprising a functional antibody Fc part are also known in the art (see, e.g., Zhu et al., Cancer Lett. 86 (1994) 127-134); and Suresh et al., Methods Enzymol. 121 (1986) 210-228).

These methods typically involve the generation of monoclonal antibodies, for example by means of fusing myeloma cells with the spleen cells from a mouse that has been immunized with the desired antigen using the hybridoma technology (see, e.g., Yokoyama et al., Curr. Protoc. Immunol. Chapter 2, Unit 2.5, 2006) or by means of recombinant antibody engineering (repertoire cloning or phage display/yeast display) (see, e.g., Chames & Baty, FEMS Microbiol. Letters 189 (2000) 1-8), and the combination of the antigen-binding domains or fragments or parts thereof of two or more different monoclonal antibodies to give a bispecific or multispecific construct using known molecular cloning techniques.

The multispecific antibodies of the invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)-cyclohexane-1-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83, and Glennie et al., 1987 J. Immunol. 139: 2367-2375. Conjugating agents are SATA and sulfo-SMCC, both available from Pierce Chemical Co. (Rockford, Ill, USA).

When the binding specificities are antibodies, they can be conjugated by sulfhydryl bonding of the C-terminus hinge regions of the two heavy chains. In a particular embodiment, the hinge region is modified to contain an odd number of sulfhydryl residues, for example one, prior to conjugation.

Alternatively, two or more binding specificities can be encoded in the same vector and expressed and assembled in the same host cell. This method is particularly useful where the bispecific molecule is a mAb×Fab, a mAb×scFv, a mAb×dsFv or a mAb×Fv fusion protein. Methods for preparing multispecific antibodies and molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the multispecific antibodies to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In a further aspect, the invention provides a nucleic acid or two nucleic acids encoding the multispecific antibody of the invention. Such nucleic acids can be optimized for expression in mammalian cells.

The term "nucleic acid" is used herein interchangeably with the term "polynucleotide(s)" and refers to one or more deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties when compared to the reference nucleic acid, and which are metabolized in a manner similar to the reference nucleotides. Examples of such analogs include, without limitation, phosphorothioates, phosphoramidates, methyl phosphonates, chiral-methyl phosphorates, 2-O-methyl ribonucleotides, peptide-nucleic acids (PNAs). Unless otherwise indicated, a particular nucleic acid also implicitly encompasses conservatively modified variants thereof (e.g., degenerate codon substitutions) and nucleic acids with complementary sequences, as well as the nucleic acid with the sequence explicitly indicated. Specifically, as detailed below, degenerate codon substitutions may be achieved by generating nucleic acids in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The invention provides substantially purified nucleic acid molecules which encode polypeptides comprising segments or domains of the multispecific antibody described above. When expressed from appropriate expression vectors, polypeptides encoded by these nucleic acid molecules are capable of exhibiting antigen-binding capacities of the multispecific antibody of the present invention.

The polynucleotide sequences can be produced by de novo solid-phase DNA synthesis or by PCR mutagenesis of an existing sequence (e.g., sequences as described in the Examples below) encoding the multispecific antibody of the invention or fragments thereof or binding domains thereof. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68: 109, 1979; the diethylphosphoramidite method of Beaucage et al., Tetra. Lett., 22: 1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif, 1990; Mattila et al., Nucleic Acids Res. 19:967, 1991; and Eckert et al., PCR Methods and Applications 1:17, 1991.

Also provided in the invention are expression vectors and host cells for producing the multispecific antibody of the invention or fragments thereof or binding domains thereof.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In this particular context, the term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

Various expression vectors can be employed to express the polynucleotides encoding the multispecific antibody chains. Both viral-based and non-viral expression vectors can be used to produce the antibodies in a mammalian host cell. Non-viral vectors and systems include plasmids, episomal vectors, typically with an expression cassette for expressing a protein or RNA, and human artificial chromosomes (see, e.g., Harrington et al., Nat Genet. 15:345, 1997). For example, non-viral vectors useful for expression of the polynucleotides encoding the multispecific antibody chains in mammalian (e.g., human) cells include pThioHis A, B and C, pcDNA3.1/His, pEBVHis A, B and C, (Invitrogen, San Diego, CA, USA), MPS V vectors, and numerous other vectors known in the art for expressing other proteins. Useful viral vectors include vectors based on retroviruses, adenoviruses, adeno-associated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68: 143, 1992.

The choice of expression vector depends on the intended host cells in which the vector is to be expressed. Typically, the expression vectors contain a promoter and other regulatory sequences (e.g., enhancers) that are operably linked to the polynucleotides encoding a multispecific antibody chain or a fragment. In one embodiment, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under non-inducing conditions without biasing the population for coding sequences whose expression products are better tolerated by the host cells. In addition to promoters, other regulatory elements may also be required or desired for efficient expression of a multispecific antibody chain or a fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20: 125, 1994; and Bittner et al., Meth. Enzymol., 153:516, 1987). For example, the SV40 enhancer or CMV enhancer may be used to increase expression in mammalian host cells.

Vectors to be used typically encode the multispecific antibody light and heavy chain including constant regions or parts thereof. Such vectors allow expression of the variable regions as fusion proteins with the constant regions thereby leading to production of intact antibodies and antigen-binding fragments thereof. Typically, such constant regions are human.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The host cells for harboring and expressing the multispecific antibody of the invention can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express the multispecific antibodies of the invention. Insect cells in combination with baculovirus vectors can also be used.

In one embodiment, mammalian host cells are used to express and produce the multispecific antibody of the invention. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed including the CHO cell lines, various COS cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPS V promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Green, M. R., and Sambrook, J., Molecular Cloning: A Laboratory Manual (Fourth Edition), Cold Spring Harbor Laboratory Press (2012)). Other methods include, e.g., electroporation, calcium phosphate treatment, liposome-mediated transformation, injection and microinjection, ballistic methods, virosomes, immunoliposomes, polycation-nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express the multispecific antibody of the invention can be prepared using expression vectors of the invention which contain viral origins of replication or endogenous expression elements and a selectable marker gene. Following the introduction of the vector, cells may be allowed to grow for 1 to 2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. The present invention thus provides a method of producing the antibody of the invention or antigen-binding fragment thereof, wherein said method comprises the step of culturing a host cell comprising a nucleic acid or a vector encoding the antibody of the invention or antigen-binding fragment thereof, whereby said antibody of the disclosure or a fragment thereof is expressed.

In one aspect, the present invention relates to a method of producing the multispecific antibody of the invention, the method comprising the step of culturing a host cell expressing a nucleic acid encoding the multispecific antibody of the invention. In particular, the present invention relates to a method of producing the multispecific antibody of the invention, the method comprising (i) providing a nucleic acid or two nucleic acids encoding the multispecific antibody of the invention or a vector or two vectors encoding the multispecific antibody of the invention, expressing said nucleic acid or nucleic acids, or said vector or vectors, and collecting said multispecific antibody or said binding domain from the expression system, or (ii) providing a host cell or host cells expressing a nucleic acid or two nucleic acids encoding the multispecific antibody of the invention, culturing said host cell or said host cells; and collecting said multispecific antibody or said binding domain from the cell culture.

In a further aspect, the present invention relates to a pharmaceutical composition comprising the multispecific antibody of the invention, and a pharmaceutically acceptable carrier. "Pharmaceutically acceptable carrier" means a medium or diluent that does not interfere with the structure of the antibodies. Pharmaceutically acceptable carriers enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible.

Certain, of such carriers enable pharmaceutical compositions to be formulated as, for example, tablets, pills, dragees, capsules, liquids, gels, syrups, slurries, suspension and lozenges for the oral ingestion by a subject. Certain of such carriers enable pharmaceutical compositions to be formulated for injection, infusion or topical administration. For example, a pharmaceutically acceptable carrier can be a sterile aqueous solution.

The pharmaceutical composition of the invention can be administered by a variety of methods known in the art. The route and/or mode of administration vary depending upon the desired results. Administration can be intravenous, intramuscular, intraperitoneal, or subcutaneous, or administered proximal to the site of the target. In particular embodiments, the administration is intramuscular, or subcutaneous, particularly subcutaneous. The pharmaceutically acceptable carrier should be suitable for intravenous, intramuscular, subcutaneous, parenteral, spinal or epidermal administration (e.g., by injection or infusion), particularly for intramuscular or subcutaneous administration. Depending on the route of administration, the active compound, i.e., the multispecific antibody of the invention, may be coated in a material to protect the compound from the action of acids and other natural conditions that may inactivate the compound.

The pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the multispecific antibody of the invention is employed in the pharmaceutical compositions of the invention. The multispecific antibodies of the invention are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

The multispecific antibody of the invention is usually administered on multiple occasions. Intervals between single dosages can be weekly, monthly or yearly. Intervals can also be irregular as indicated by measuring blood levels of the multispecific antibody of the invention in the patient. Alternatively, the multispecific antibody of the invention can be administered as a sustained release formulation, in which case less frequent administration is required. Dosage and frequency vary depending on the half-life of the antibody in the patient. In general, humanized antibodies show longer half-life than that of chimeric antibodies and non-human antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

In one aspect, the present invention relates to the multispecific antibody of the invention or the pharmaceutical composition of the invention for use as a medicament. In a suitable embodiment, the present invention provides the multispecific antibody or the pharmaceutical composition for use in the treatment of a disease selected from allergic, inflammatory and autoimmune diseases, particularly from inflammatory and autoimmune diseases.

In another aspect, the present invention provides the pharmaceutical composition for use in the manufacture of a medicament for the treatment of an allergic, inflammatory or autoimmune disease, particularly of an inflammatory or autoimmune disease.

In another aspect, the present invention relates to the use of the multispecific antibody or the pharmaceutical composition for treating an allergic, inflammatory or autoimmune disease, particularly for treating an inflammatory or autoimmune disease, in a subject in need thereof.

In another aspect, the present invention relates to a method of treating a subject comprising administering to the subject a therapeutically effective amount of the multispecific antibody of the present invention. In a suitable embodiment, the present invention relates to a method for the treatment of an allergic, inflammatory or autoimmune disease, particularly for treating an inflammatory or autoimmune disease, in a subject comprising administering to the subject a therapeutically effective amount of the multispecific antibody of the present invention.

The term "subject" includes human and non-human animals.

The term "animals" include all vertebrates, e.g., non-human mammals and non-mammals, such as non-human primates, sheep, dog, cow, chickens, amphibians, and reptiles. Except when noted, the terms "patient" or "subject" are used herein interchangeably.

The terms "treatment", "treating", "treat", "treated", and the like, as used herein, refer to obtaining a desired pharmacologic and/or physiologic effect. The effect may be therapeutic in terms of a partial or complete cure for a disease and/or adverse effect attributable to the disease or delaying the disease progression. "Treatment", as used herein, covers any treatment of a disease in a mammal, e.g., in a human, and includes: (a) inhibiting the disease, i.e., arresting its development; and (b) relieving the disease, i.e., causing regression of the disease.

The term "therapeutically effective amount" or "efficacious amount" refers to the amount of an agent that, when administered to a mammal or other subject for treating a disease, is sufficient to affect such treatment for the disease. The "therapeutically effective amount" will vary depending on the agent, the disease and its severity and the age, weight, etc., of the subject to be treated.

In one embodiment, the allergic, inflammatory and autoimmune diseases are selected from pruritus-causing allergic diseases, pruritus-causing inflammatory diseases and pruritus-causing autoimmune diseases, particularly from pruritus-causing inflammatory diseases and pruritus-causing autoimmune diseases. The terms "pruritus" and "itch", which are herein used synonymously, refers to a sensation that causes the desire or reflex to scratch. Scratching can be problematic particularly in the case of chronic skin diseases that induce itching, such as atopic dermatitis, dermatomycoses, psoriasis or urticaria, as the permanent itching stimulates patients to scratch the affected skin areas constantly and/or excessively, which often leads to skin injuries and further deterioration of the skin surface.

The term "allergic diseases" or "allergies" as used herein refers to a large number of conditions caused by hypersensitivity of the immune system to typically harmless substances in the environment.

The term "inflammatory diseases" as used herein refers to a vast number of inflammatory disorders, i.e. inflammatory abnormalities, which are often characterized by prolonged inflammation, known as chronic inflammation. The term "inflammation" refers to the complex biological response of body tissues to harmful stimuli, such as pathogens, damaged cells, or irritants. It is a protective response involving immune cells, blood vessels, and molecular mediators. While regular inflammation reactions are essential for the body to eliminate the initial cause of cell injury, clear out necrotic cells and tissues damaged from the original insult and the inflammatory process, and to initiate tissue repair, inflammatory disorders are generally characterized by persistent inflammation in the absence of harmful stimuli.

The term "autoimmune diseases" as used herein refers to a condition arising from an abnormal immune response to a functioning body part. It is the result of autoimmunity, i.e. the presence of self-reactive immune response (e.g., autoantibodies, self-reactive T cells), with or without damage or pathology resulting from it, which is typically restricted to certain organs or involve a particular tissue in different places.

In particular embodiments, the pruritus-causing inflammatory or autoimmune disease is selected from atopic dermatitis, acute allergic contact dermatitis, chronic spontaneous urticaria, bullous pemphigoid, alopecia areata, dermatomyositis, prurigo nodularis, psoriasis and atopic asthma, in particular from atopic dermatitis.

In another aspect, the allergic, inflammatory and autoimmune diseases are selected from atopic dermatitis, acute allergic contact dermatitis, chronic spontaneous urticaria, bullous pemphigoid, alopecia areata, dermatomyositis, prurigo nodularis, psoriasis and atopic asthma, in particular from atopic dermatitis.

In another embodiment, the allergic, inflammatory and autoimmune diseases are selected from allergic asthma, allergic rhinitis, inflammatory airway disease, recurrent airway obstruction, airway hyperresponsiveness, chronic obstruction pulmonary disease, Crohn disease, chronic non-histamine related urticaria, antihistamine-unresponsive mastocytosis, lichen simplex chronicus, seborrhoeic dermatitis, xeroderma, Dermatitis herpetiformis, lichen planus and ulcerative colitis.

In another embodiment, the present invention provides the multispecific antibody or the pharmaceutical composition, as defined herein, for use in the treatment of a disease, which is a neuropathic pruritus disease selected from post-herpetic neuralgia, post-herpetic itch, notalgia paresthetica, multiple sclerosis and brachioradial pruritus.

In another embodiment, the present invention provides the multispecific antibody or the pharmaceutical composition for use in an antipruritic agent for the treatment of a systemic disease with itching, which disease is selected from Cholestasis, chronic kidney disease, Hodgkin's disease, cutaneous T-cell lymphoma and other lymphomas or leukemias associated with chronic itch, polycythemia vera, hyperthyroidism, chronic post-arthropod itch (Id reaction), pregnancy-induced chronic itch (e.g. PUPPP), eosinophilic pustular folliculitis, drug hypersensitivity reactions, chronic pruritus of the elderly or dry skin itch (local, generalized), and pruritus at the scar portion after burn (post-burn itch), genetic or nevoid chronic itches (e.g. Netherton syndrome, Darier's disease (Morbus Darier), Hailey-Hailey disease, inflammatory linear verrucous epidermal nevus (ILVEN), familial primary cutaneous amyloidosis, Olmsted syndrome), aquagenic pruritus, fiberglass dermatitis, mucous chronic itch, chemotherapy-induced itch and HIV.

Sequence Listing (Mutations Designated According to AHo Numbering Scheme; the CDRs Defined According to Numab CDR Definition, Unless Specified Otherwise)

TABLE 1

Examples of IL-4R binding domains as used in the present invention (CDR residues shown in bold and italic letters).

| SEQ ID NUMBER | Ab region | Sequence |
|---|---|---|
| 44-34-C10 | | |
| SEQ ID NO: 1 | HCDR1<br>(H27-H42; AHo numbering) | ***GFSSSSAHYMC*** |
| SEQ ID NO: 2 | HCDR2<br>(H57-H76; AHo numbering) | ***CIYAGSRGSTYYASWAKG*** |
| SEQ ID NO: 3 | HCDR3<br>(H108-H138; AHo numbering) | ***RAAFVNRGVSWIWPYYFSL*** |
| SEQ ID NO: 4 | VH<br>(44-34-C10-sc07/<br>44-34-C10-sc08) | EVQLVESGGGLVQPGGSLRLSCAAS***GFSSSSAHYMC***WVRQAPGKGLEWI<br>G***CIYAGSRGSTYYASWAKG***RFTISRDNSKNTVYLQMNSLRAEDTAVYYC<br>A***RAAFVNRGVSWIWPYYFSL***WGQGTLVTVSS |
| SEQ ID NO: 5 | VH<br>(44-34-C10-sc09) | EVQLVESGGGRVQPGGSLRLSCAAS***GFSSSSAHYMC***WVRQAPGKGLEWI<br>G***CIYAGSRGSTYYASWAKG***RFTISKASSTTVYLQMNSLRAEDTATYYCA<br>***RAAFVNRGVSWIWPYYFSL***WGQGTQVTVSS |
| SEQ ID NO: 6 | VH (44-34-C10-sc09)<br>mutations R12L,<br>T103V, Q144L | EVQLVESGGGLVQPGGSLRLSCAAS***GFSSSSAHYMC***WVRQAPGKGLEWI<br>G***CIYAGSRGSTYYASWAKG***RFTISKASSTTVYLQMNSLRAEDTAVYYCA<br>***RAAFVNRGVSWIWPYYFSL***WGQGTLVTVSS |
| SEQ ID NO: 7 | LCDR1<br>(L24-L42; AHo numbering) | ***QASEDIESYLA*** |
| SEQ ID NO: 8 | LCDR2<br>(L58-L72; AHo numbering)<br>(present in 44-34-C10-sc06,<br>44-34-C10-sc08<br>and 44-34-C10-sc09) | ***RASTLAY*** |
| SEQ ID NO: 9 | LCDR3<br>(L107-L138; AHo numbering) | ***LGSSYSTGSNI*** |
| SEQ ID NO: 10 | VL<br>(44-34-C10-sc06/<br>44-34-C10-sc09) | DIQMTQSPSSLSASVGDRVTITC***QASEDIESYLA***WYQQKPGKAPKLLIY***R***<br>***ASTLAY***GVPSRFSGSGSGTDFTLTISSLQPEDFATYYC***LGSSYSTGSNI*** |

TABLE 1-continued

| Examples of IL-4R binding domains as used in the present invention (CDR residues shown in bold and italic letters). | | |
|---|---|---|
| SEQ ID NUMBER | Ab region | Sequence |
| SEQ ID NO: 11 | VL (44-34-C10-sc08) | DIQMTQSPSSLSARVGDRVTITC***QASEDIESYLA***WYQQKPGKAPKLLIY***RASTLAY***GVPSRFSGSGSGRDFTLTISSLQPEDFATYYC***LGSSYSTGSNI*** |

TABLE 2

| Examples of IL-31 binding domains as used in the present invention (CDR residues shown in bold and italic letters). | | |
|---|---|---|
| SEQ ID NUMBER | Ab region | Sequence |
| 50-09-D07 | | |
| SEQ ID NO: 12 | HCDR1 (H27-H42; AHo numbering) | ***GFSFSANYWIC*** |
| SEQ ID NO: 13 | HCDR2 (H57-H76; AHo numbering) (present in 50-09-D07-sc04, 50-09-D07-sc05 and 50-09-D07-sc07) | ***CIYIGSRADTYYAPWAKG*** |
| SEQ ID NO: 14 | HCDR3 (H108-H138; AHo numbering) | ***RFSSGIYDLDRFFL*** |
| SEQ ID NO: 15 | VH (50-09-D07-sc03/ 50-09-D07-sc07) | QSQLVESGGGLVQPGGSLRLSCAAS***GFSFSANYWIC***WVRQAPGKGLEWIVC***CIYIGSRADTYYAPWAKG***RFTISKDNSKNTVYLQMNSLRAEDTAVYFCA***RFSSGIYDLDRFFL***WGQGTLVTVSS |
| SEQ ID NO: 16 | VH (50-09-D07-sc04) | QSQLVESGGGRVQPGGSLRLSCAAS***GFSFSANYWIC***WVRQAPGKGLEWIVC***CIYIGSRADTYYAPWAKG***RFTISKDNSKNTVYLQMNSLRAEDTATYFCA***RFSSGIYDLDRFFL***WGQGTQVTVSS |
| SEQ ID NO: 17 | LCDR1 (L24-L42; AHo numbering) | ***QASQSIDSWLA*** |
| SEQ ID NO: 18 | LCDR1 (L24-L42; AHo numbering) | ***QASQSIESWLA*** |
| SEQ ID NO: 19 | LCDR2 (L58-L72; AHo numbering) | ***QASKLAS*** |
| SEQ ID NO: 20 | LCDR3 (L107-L138; AHo numbering) | ***QTYYGGGHIGWG*** |
| SEQ ID NO: 21 | VL (50-09-D07-sc03 to sc06) | AFQLTQSPSSLSASVGDRVTITC***QASQSIDSWLA***WYQQKPGKPPKLLIY***QASKLAS***GVPSRFSGSGSGTDYTLTISSLQPEDFATYYC***QTYYGGGHIGWG*** |
| SEQ ID NO: 22 | VL (50-09-D07-sc07) | AFQLTQSPSSLSASVGDRVTITC***QASQSIESWLA***WYQQKPGKPPKLLIY***QASKLAS***GVPSRFSGSGSGTDYTLTISSLQPEDFATYYC***QTYYGGGHIGWG*** |

TABLE 3

| Other sequences related to the present invention. | | |
|---|---|---|
| SEQ ID NUMBER | Ab region | Sequence |
| SEQ ID NO: 23 | VH3 | EVQLVESGGGLVQPGGSLRLSCAAS***GFSFSANYYPC***WVRQAPGKGLEWIG***CIYGGSSDITYDANWTK***GRFTISRDNSKNTVYLQMNSLRAEDTAVYYCA***RSAWYSGWGGDL***WGQGTLVTVSS |
| SEQ ID NO: 24 | VH4 | QVQLQESGPGLVKPSETLSLTCKVS***GFSFSNSYWIC***WIRQPPGKGLEWIG***CTFVGSSDSTYYANWAKG***RVTISVDSSKNQFSLKLSSVTAADTAVYYCA***RHPSDAVYGYANNL***WGQGTLVTVSS |

TABLE 3-continued

| Other sequences related to the present invention. | | |
|---|---|---|
| SEQ ID NUMBER | Ab region | Sequence |
| SEQ ID NO: 25 | Vkappa1 | DIQMTQSPSSLSASVGDRVTITC***QASQSINNVLA***WYQQKPGKAPKLLIY***RASTLAS***GVPSRFSGSGSGTDFTLTISSLOPEDFATYYC***QSSYGNYGD***FGTGTKVTVLG |
| SEQ ID NO: 26 | Vλ germline-based FR4 (Sk17) | FGTGTKVTVLG |
| SEQ ID NO: 27 | Vλ germline-based FR4 (Sk12) | FGGGTKLTVLG |
| SEQ ID NO: 28 | Vλ germline-based FR4 | FGGGTQLIILG |
| SEQ ID NO: 29 | Vλ germline-based FR4 | FGEGTELTVLG |
| SEQ ID NO: 30 | Vλ germline-based FR4 | FGSGTKVTVLG |
| SEQ ID NO: 31 | Vλ germline-based FR4 | FGGGTQLTVLG |
| SEQ ID NO: 32 | Vλ germline-based FR4 | FGGGTQLTALG |
| SEQ ID NO: 33 | Vλ germline-based FR4_G141C | FGCGTKVTVLG |
| SEQ ID NO: 34 | Linker | GGGGSGGGGSGGGGSGGGGS |
| SEQ ID NO: 35 | Linker | GGGGS |
| SEQ ID NO: 36 | Linker | GGGGSGGGGS |

TABLE 4

| Examples of multispecific antibodies as used in the present invention (Linkers are shown in bold). | | |
|---|---|---|
| SEQ ID NUMBER | Ab Format | Sequence |
| PRO2198 | | |
| SEQ ID NO: 37 | Morrison-H, LC | DIQMTQSPSSLSARVGDRVTITCQASEDIESYLAWYQQKPGKAPKLLIYRASTLAYGVPSRFSGSGSGRDFTLTISSLQPEDFATYYCLGSSYSTGSNIFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| SEQ ID NO: 38 | Morrison-H, HC | EVQLVESGGGLVQPGGSLRLSCAASGFSSSSAHYMCWVRQAPGKGLEWIGCIYAGSRGSTYYASWAKGRFTISRDNSKNTVYLQMNSLRAEDTAVYYCARAAFVNRGVSWIWPYYFSLWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLG**GGGGSGGGGS**AFQLTQSPSSLSASVGDRVTITCQASQSIDSWLAWYQQKPGKPPKLLIYQASKLASGVPSRFSGSGSGTDYTLTISSLQPEDFATYYCQTYYGGGHIGWGFGTGTKVTVLG**GGGGSGGGGSGGGGSGGGGS**QSQLVESGGGRVQPGGSLRLSCAASGFSFSANYWICWVRQAPGKGLEWIVCIYIGSRADTYYAPWAKGRFTISKDNSKNTVYLQMNSLRAEDTATYFCARFSSGIYDLDRFFLWGQGTQVTVSS |
| PRO2199 | | |
| SEQ ID NO: 39 | Morrison-H, LC | DIQMTQSPSSLSASVGDRVTITCQASEDIESYLAWYQQKPGKAPKLLIYRASTLAYGVPSRFSGSGSGTDFTLTISSLQPEDFATYYCLGSSYSTGSNIFGQGTK |

TABLE 4-continued

Examples of multispecific antibodies as used in the present invention (Linkers are shown in bold).

| SEQ ID NUMBER | Ab Format | Sequence |
|---|---|---|
| | | VEIKRTVAAPSVFIFPPSDEQLKSGTASVVCLLNN<br>FYPREAKVQWKVDNALQSGNSQESVTEQDSKDSTY<br>SLSSTLTLSKADYEKHKVYACEVTHQGLSSPVTKS<br>FNRGEC |
| SEQ ID NO: 40 | Morrison-H, HC | EVQLVESGGGRVQPGGSLRLSCAASGFSSSSAHYM<br>CWVRQAPGKGLEWIGCIYAGSRGSTYYASWAKGRF<br>TISKASSTTVYLQMNSLRAEDTATYYCARAAFVNR<br>GVSWIWPYYFSLWGQGTQVTVSSASTKGPSVFPLA<br>PCSRSTSESTAALGCLVKDYFPEPVTVSWNSGALT<br>SGVHTFPAVLQSSGLYSLSSVVTVPSSSLGTKTYT<br>CNVDHKPSNTKVDKRVESKYGPPCPPCPAPEFLGG<br>PSVFLFPPKPKDTLMISRTPEVTCVVVDVSQEDPE<br>VQFNWYVDGVEVHNAKTKPREEQFNSTYRVVSVLT<br>VLHQDWLNGKEYKCKVSNKGLPSSIEKTISKAKGQ<br>PREPQVYTLPPSQEEMTKNQVSLTCLVKGFYPSDI<br>AVEWESNGQPENNYKTTPPVLDSDGSFFLYSRLTV<br>DKSRWQEGNVFSCSVMHEALHNHYTQKSLSLSLG**G**<br>**GGGSGGGGS**AFQLTQSPSSLSASVGDRVTITCQAS<br>QSIDSWLAWYQQKPGKPPKLLIYQASKLASGVPSR<br>FSGSGSGTDYTLTISSLQPEDFATYYCQTYYGGGH<br>IGWGFGTGTKVTVLG**GGGGSGGGGSGGGGSGGGGS**<br>QSQLVESGGGRVQPGGSLRLSCAASGFSFSANYWI<br>CWVRQAPGKGLEWIVCIYIGSRADTYYAPWAKGRF<br>TISKDNSKNTVYLQMNSLRAEDTATYFCARFSSGI<br>YDLDRFFLWGQGTQVTVSS |
| PRO2200 | | |
| SEQ ID NO: 41 | Morrison-H, LC | AFQLTQSPSSLSASVGDRVTITCQASQSIDSWLAW<br>YQQKPGKPPKLLIYQASKLASGVPSRFSGSGSGTD<br>YTLTISSLQPEDFATYYCQTYYGGGHIGWGFGQGT<br>KVEIKRTVAAPSVFIFPPSDEQLKSGTASVVCLLN<br>NFYPREAKVQWKVDNALQSGNSQESVTEQDSKDST<br>YSLSSTLTLSKADYEKHKVYACEVTHQGLSSPVTK<br>SFNRGEC |
| SEQ ID NO: 42 | Morrison-H, HC | QSQLVESGGGRVQPGGSLRLSCAASGFSFSANYWI<br>CWVRQAPGKGLEWIVCIYIGSRADTYYAPWAKGRF<br>TISKDNSKNTVYLQMNSLRAEDTATYFCARFSSGI<br>YDLDRFFLWGQGTQVTVSSASTKGPSVFPLAPCSR<br>STSESTAALGCLVKDYFPEPVTVSWNSGALTSGVH<br>TFPAVLQSSGLYSLSSVVTVPSSSLGTKTYTCNVD<br>HKPSNTKVDKRVESKYGPPCPPCPAPEFLGGPSVF<br>LFPPKPKDTLMISRTPEVTCVVVDVSQEDPEVQFN<br>WYVDGVEVHNAKTKPREEQFNSTYRVVSVLTVLHQ<br>DWLNGKEYKCKVSNKGLPSSIEKTISKAKGQPREP<br>QVYTLPPSQEEMTKNQVSLTCLVKGFYPSDIAVEW<br>ESNGQPENNYKTTPPVLDSDGSFFLYSRLTVDKSR<br>WQEGNVFSCSVMHEALHNHYTQKSLSLSLGGGGG**G**<br>**GGGS**DIQMTQSPSSLSARVGDRVTITCQASEDIES<br>YLAWYQQKPGKAPKLLIYRASTLAYGVPSRFSGSG<br>SGRDFTLTISSLQPEDFATYYCLGSSYSTGSNIFG<br>TGTKVTVLG**GGGGSGGGGSGGGGSGGGGS**EVQLVE<br>SGGGLVQPGGSLRLSCAASGFSSSSAHYMCWVRQA<br>PGKGLEWIGCIYAGSRGSTYYASWAKGRFTISRDN<br>SKNTVYLQMNSLRAEDTAVYYCARAAFVNRGVSWI<br>WPYYFSLWGQGTLVTVSS |
| PRO2201 | | |
| SEQ ID NO: 43 | Morrison-H, LC | AFQLTQSPSSLSASVGDRVTITCQASQSIDSWLAW<br>YQQKPGKPPKLLIYQASKLASGVPSRFSGSGSGTD<br>YTLTISSLQPEDFATYYCQTYYGGGHIGWGFGQGT<br>KVEIKRTVAAPSVFIFPPSDEQLKSGTASVVCLLN<br>NFYPREAKVQWKVDNALQSGNSQESVTEQDSKDST<br>YSLSSTLTLSKADYEKHKVYACEVTHQGLSSPVTK<br>SFNRGEC |
| SEQ ID NO: 44 | Morrison-H, HC | QSQLVESGGGRVQPGGSLRLSCAASGFSFSANYWI<br>CWVRQAPGKGLEWIVCIYIGSRADTYYAPWAKGRF<br>TISKDNSKNTVYLQMNSLRAEDTATYFCARFSSGI<br>YDLDRFFLWGQGTQVTVSSASTKGPSVFPLAPCSR<br>STSESTAALGCLVKDYFPEPVTVSWNSGALTSGVH<br>TFPAVLQSSGLYSLSSVVTVPSSSLGTKTYTCNVD |

TABLE 4-continued

Examples of multispecific antibodies as used in the present invention (Linkers are shown in bold).

| SEQ ID NUMBER | Ab Format | Sequence |
|---|---|---|
| | | HKPSNTKVDKRVESKYGPPCPPCPAPEFLGGPSVF<br>LFPPKPKDTLMISRTPEVTCVVVDVSQEDPEVQFN<br>WYVDGVEVHNAKTKPREEQFNSTYRVVSVLTVLHQ<br>DWLNGKEYKCKVSNKGLPSSIEKTISKAKGQPREP<br>QVYTLPPSQEEMTKNQVSLTCLVKGFYPSDIAVEW<br>ESNGQPENNYKTTPPVLDSDGSFFLYSRLTVDKSR<br>WQEGNVFSCSVMHEALHNHYTQKSLSLSLG**GGGGS**<br>**GGGGS**DIQMTQSPSSLSASVGDRVTITCQASEDIE<br>SYLAWYQQKPGKAPKLLIYRASTLAYGVPSRFSGS<br>GSGTDFTLTISSLQPEDFATYYCLGSSYSTGSNIF<br>GTGTKVTVLG**GGGGSGGGGSGGGGSGGGGS**EVQLV<br>ESGGGRVQPGGSLRLSCAASGFSSSSAHYMCWVRQ<br>APGKGLEWIGCIYAGSRGSTYYASWAKGRFTISKA<br>SSTTVYLQMNSLRAEDTATYYCARAAFVNRGVSWI<br>WPYYFSLWGQGTQVTVSS |
| PRO2206 | | |
| SEQ ID NO: 45 | Morrison-L, LC | DIQMTQSPSSLSARVGDRVTITCQASEDIESYLAW<br>YQQKPGKAPKLLIYRASTLAYGVPSRFSGSGSGRD<br>FTLTISSLQPEDFATYYCLGSSYSTGSNIFGQGTK<br>VEIKRTVAAPSVFIFPPSDEQLKSGTASVVCLLNN<br>FYPREAKVQWKVDNALQSGNSQESVTEQDSKDSTY<br>SLSSTLTLSKADYEKHKVYACEVTHQGLSSPVTKS<br>FNRGEC**GGGGSGGGGS**AFQLTQSPSSLSASVGDRV<br>TITCQASQSIDSWLAWYQQKPGKPPKLLIYQASKL<br>ASGVPSRFSGSGSGTDYTLTISSLQPEDFATYYCQ<br>TYYGGGHIGWGFGTGTKVTVLG**GGGGSGGGGSGGG**<br>**GSGGGGS**QSQLVESGGGRVQPGGSLRLSCAASGFS<br>FSANYWICWVRQAPGKGLEWIVCIYIGSRADTYYA<br>PWAKGRFTISKDNSKNTVYLQMNSLRAEDTATYFC<br>ARFSSGIYDLDRFFLWGQGTQVTVSS |
| SEQ ID NO: 46 | Morrison-L, HC | EVQLVESGGGLVQPGGSLRLSCAASGFSSSSAHYM<br>CWVRQAPGKGLEWIGCIYAGSRGSTYYASWAKGRF<br>TISRDNSKNTVYLQMNSLRAEDTAVYYCARAAFVN<br>RGVSWIWPYYFSLWGQGTLVTVSSASTKGPSVFPL<br>APCSRSTSESTAALGCLVKDYFPEPVTVSWNSGAL<br>TSGVHTFPAVLQSSGLYSLSSVVTVPSSSLGTKTY<br>TCNVDHKPSNTKVDKRVESKYGPPCPPCPAPEFLG<br>GPSVFLFPPKPKDTLMISRTPEVTCVVVDVSQEDP<br>EVQFNWYVDGVEVHNAKTKPREEQFNSTYRVVSVL<br>TVLHQDWLNGKEYKCKVSNKGLPSSIEKTISKAKG<br>QPREPQVYTLPPSQEEMTKNQVSLTCLVKGFYPSD<br>IAVEWESNGQPENNYKTTPPVLDSDGSFFLYSRLT<br>VDKSRWQEGNVFSCSVMHEALHNHYTQKSLSLSLG |
| PRO2207 | | |
| SEQ ID NO: 47 | Morrison-L, LC | DIQMTQSPSSLSASVGDRVTITCQASEDIESYLAW<br>YQQKPGKAPKLLIYRASTLAYGVPSRFSGSGSGTD<br>FTLTISSLQPEDFATYYCLGSSYSTGSNIFGQGTK<br>VEIKRTVAAPSVFIFPPSDEQLKSGTASVVCLLNN<br>FYPREAKVQWKVDNALQSGNSQESVTEQDSKDSTY<br>SLSSTLTLSKADYEKHKVYACEVTHQGLSSPVTKS<br>FNRGEC**GGGGSGGGGS**AFQLTQSPSSLSASVGDRV<br>TITCQASQSIDSWLAWYQQKPGKPPKLLIYQASKL<br>ASGVPSRFSGSGSGTDYTLTISSLQPEDFATYYCQ<br>TYYGGGHIGWGFGTGTKVTVLG**GGGGSGGGGSGGG**<br>**GSGGGGS**QSQLVESGGGRVQPGGSLRLSCAASGFS<br>FSANYWICWVRQAPGKGLEWIVCIYIGSRADTYYA<br>PWAKGRFTISKDNSKNTVYLQMNSLRAEDTATYFC<br>ARFSSGIYDLDRFFLWGQGTQVTVSS |
| SEQ ID NO: 48 | Morrison-L, HC | EVQLVESGGGRVQPGGSLRLSCAASGFSSSSAHYM<br>CWVRQAPGKGLEWIGCIYAGSRGSTYYASWAKGRF<br>TISKASSTTVYLQMNSLRAEDTATYYCARAAFVNR<br>GVSWIWPYYFSLWGQGTQVTVSSASTKGPSVFPLA<br>PCSRSTSESTAALGCLVKDYFPEPVTVSWNSGALT<br>SGVHTFPAVLQSSGLYSLSSVVTVPSSSLGTKTYT<br>CNVDHKPSNTKVDKRVESKYGPPCPPCPAPEFLGG<br>PSVFLFPPKPKDTLMISRTPEVTCVVVDVSQEDPE<br>VQFNWYVDGVEVHNAKTKPREEQFNSTYRVVSVLT<br>VLHQDWLNGKEYKCKVSNKGLPSSIEKTISKAKGQ<br>PREPQVYTLPPSQEEMTKNQVSLTCLVKGFYPSDI |

TABLE 4-continued

Examples of multispecific antibodies as used in the present invention (Linkers are shown in bold).

| SEQ ID NUMBER | Ab Format | Sequence |
|---|---|---|
| | | AVEWESNGQPENNYKTTPPVLDSDGSFFLYSRLTV DKSRWQEGNVFSCSVMHEALHNHYTQKSLSLSLG |
| PRO2208 | | |
| SEQ ID NO: 49 | Morrison-L, LC | DIQMTQSPSSLSASVGDRVTITCQASEDIESYLAW YQQKPGKAPKLLIYRASTLAYGVPSRFSGSGSGTD FTLTISSLQPEDFATYYCLGSSYSTGSNIFGQGTK VEIKRTVAAPSVFIFPPSDEQLKSGTASVVCLLNN FYPREAKVQWKVDNALQSGNSQESVTEQDSKDSTY SLSSTLTLSKADYEKHKVYACEVTHQGLSSPVTKS FNRGEC**GGGGSGGGGS**AFQLTQSPSSLSASVGDRV TITCQASQSIDSWLAWYQQKPGKPPKLLIYQASKL ASGVPSRFSGSGSGTDYTLTISSLQPEDFATYYCQ TYYGGGHIGWGFGTGTKVTVL**GGGGGSGGGGSGGG GSGGGGS**QSQLVESGGGRVQPGGSLRLSCAASGFS FSANYWICWVRQAPGKGLEWIVCIYIGSRADTYYA PWAKGRFTISKDNSKNTVYLQMNSLRAEDTATYFC ARFSSGIYDLDRFFLWGQGTQVTVSS |
| SEQ ID NO: 50 | Morrison-L, HC | EVQLVESGGGLVQPGGSLRLSCAASGFSSSSAHYM CWVRQAPGKGLEWIGCIYAGSRGSTYYASWAKGRF TISKASSTTVYLQMNSLRAEDTAVYYCARAAFVNR GVSWIWPYYFSLWGQGTLVTVSSASTKGPSVFPLA PCSRSTSESTAALGCLVKDYFPEPVTVSWNSGALT SGVHTFPAVLQSSGLYSLSSVVTVPSSSLGTKTYT CNVDHKPSNTKVDKRVESKYGPPCPPCPAPEFLGG PSVFLFPPKPKDTLMISRTPEVTCVVVDVSQEDPE VQFNWYVDGVEVHNAKTKPREEQFNSTYRVVSVLT VLHQDWLNGKEYKCKVSNKGLPSSIEKTISKAKGQ PREPQVYTLPPSQEEMTKNQVSLTCLVKGFYPSDI AVEWESNGQPENNYKTTPPVLDSDGSFFLYSRLTV DKSRWQEGNVFSCSVMHEALHNHYTQKSLSLSLG |

Throughout the text of this application, should there be a discrepancy between the text of the specification (e.g., Tables 1 to 4) and the sequence listing, the text of the specification shall prevail.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

The following Examples illustrates the invention described above, but is not, however, intended to limit the scope of the invention in any way. Other test models known as such to the person skilled in the pertinent art can also determine the beneficial effects of the claimed invention.

EXAMPLES

Example 1: Generation and Testing of Anti-IL-4R Molecules

Aim of the Project

The goal of the project was to generate humanized monoclonal antibody fragments that specifically bind to and neutralize the biological effect of human IL-4R. A further goal was to identify anti-IL-4R antibody fragments that are potent and stable enough for incorporation into multispecific antibody formats.

1.1. Generation, Selection, Humanization and Production of the Anti-IL-4R Binding Domains Included in the Multispecific Antibodies of the Present Invention The generation of anti-IL-4R rabbit antibodies, the screening and selection of suitable clones, as well as the humanization and production of the humanized anti-IL-4R binding domains were performed as described in the parallel patent application EP20216928.0, which is herewith incorporated by reference. Anti-IL-4R binding domains that are potent and stable enough for incorporation into multispecific antibody formats were identified and selected based on their biophysical and functional properties.

1.2. Characterization of Suitable Anti-IL-4R Binding Domains

For further characterization of suitable anti-IL-4R binding domains, the following analyses were performed.

1.2.1. Manufacture of Suitable Anti-IL-4R Binding Domains for Characterization (scFv Format)

Expression of mammalian constructs was performed in CHO—S cells using CHOgro transient transfection kit (Mirus). Cultures were harvested after 5-7 days (when cell viability <70% was reached) expression at 37° C. by centrifugation followed by filtration. Proteins were purified from clarified culture supernatants by Protein L affinity chromatography. None of the molecules needed polishing by size exclusion chromatography as all molecules exhibited at least one affinity chromatography fraction with a monomeric content >95% post capture as assessed by SE-HPLC analysis. Samples were re-buffered to final buffer (50 mM phosphate-citrate buffer with 150 mM NaCl at pH 6.4) by dialysis. For quality control of the manufactured material standard analytical methods such as SE-HPLC, $UV_{280}$ and SDS-PAGE were applied. The manufacture characteristics of eight scFv molecules originating from four clones that were deemed to be suitable for incorporation into multispecific antibody formats are summarized in Table 6. Manufacture characteristics of the CDR graft (sc01) and the Full graft (sc04) of clone 44-18-C11 (PRO1510) and its variants (PRO1549-PRO1554) are summarized in Table 7.

TABLE 6 scFv manufacture of 8 selected clones. Sc01: CDR-graft, sc04: Full graft

| Protein ID | Description | Expression volume [ml] | Yield post affinity chromatography purification [mg] | Final yield [mg] | Titer [mg/l] | Purity SE-HPLC [% monomer] | Purity SDS-PAGE | $T_m$ [° C.] | $T_{onset}$ [° C.] |
|---|---|---|---|---|---|---|---|---|---|
| PRO1506 | 44-03-A03-sc01 | 200 | 14.6 | 11.7 | 58 | 99.0 | identity confirmed | 62.8 | 56.7 |
| PRO1524 | 44-03-A03-sc04 | 100 | 6.5 | 5.0 | 50 | 99.0 | identity confirmed | 59.6 | 54.0 |
| PRO1510 | 44-18-C11-sc01 | 200 | 12.5 | 10.0 | 50 | 98.0 | identity confirmed | 71.5 | 64.0 |
| PRO1528 | 44-18-C11-sc04 | 100 | 5.7 | 4.7 | 47 | 99.0 | identity confirmed | 59.1 | 52.3 |
| PRO1517 | 44-34-C10-sc01 | 50 | 1.5 | 0.3 | 7 | 97.6 | identity confirmed | 63.7 | 57.0 |
| PRO1535 | 44-34-C10-sc04 | 100 | 7.3 | 4.6 | 46 | 99.1 | identity confirmed | 67.9 | 62.7 |
| PRO1520 | 44-39-B07-sc01 | 100 | 9.5 | 3.1 | 31 | 98.2 | identity confirmed | 70.2 | 64.0 |
| PRO1538 | 44-39-B07-sc04 | 100 | 8.4 | 2.2 | 22 | 95.0 | identity confirmed | 68.3 | 63.7 |

TABLE 7 scFv manufacture of all grafting variants of clone 44-18-C11. Sc01: CDR-graft, sc04: Full graft

| Protein ID | Description | Expression volume [ml] | Yield post capture [mg] | Final yield [mg] | Titer [mg/l] | Purity SE-HPLC [% monomer] | Purity SDS-PAGE | $T_m$ [° C.] | $T_{onset}$ [° C.] |
|---|---|---|---|---|---|---|---|---|---|
| PRO1510 | 44-18-C11-sc01 | 200 | 12.5 | 10.0 | 50 | 98.0 | identity confirmed | 71.5 | 64.0 |
| PRO1528 | 44-18-C11-sc04 | 100 | 5.7 | 4.7 | 47 | 99.0 | identity confirmed | 59.1 | 52.3 |
| PRO1549 | 44-18-C11-sc05 | 100 | 8.1 | 6.8 | 68 | 99.0 | identity confirmed | 66.9 | 61.0 |
| PRO1550 | 44-18-C11-sc06 | 100 | 8.0 | 9.0 | 90 | 99.0 | identity confirmed | 69.8 | 62.0 |
| PRO1551 | 44-18-C11-sc07 | 100 | 8.1 | 6.8 | 68 | 98.0 | identity confirmed | 68.1 | 62.7 |
| PRO1552 | 44-18-C11-sc08 | 100 | 6.8 | 5.5 | 55 | 98.0 | identity confirmed | 55.6 | 47.0 |
| PRO1553 | 44-18-C11-sc09 | 100 | 7.5 | 6.7 | 67 | 99.0 | identity confirmed | 62.8 | 56.0 |
| PRO1554 | 44-18-C11-sc10 | 100 | 8.8 | 6.9 | 69 | 99.0 | identity confirmed | 69.5 | 61.3 |

1.2.2. Pharmacodynamic Characterization of Suitable Anti-IL-4R Binding Domains (scFvs Format)

The scFvs antibodies that were evaluated as suitable were characterized for primary pharmacodynamics properties.

Affinity to Human IL-4R

Affinity of the 14 humanized scFvs (derived from 4 rabbit monoclonal antibodies) to human IL-4R was determined by SPR analysis on a T200 device (Biacore, GE Healthcare). Human IL-4R-Fc was captured via an anti-human IgG-Fc coupled to a carboxylmethylated dextran surface and the scFvs were injected as analyte. After each analyte injection cycle the sensor chip was regenerated and new antigen was captured. The scFvs were measured using a dose response multi-cycle kinetic assay with seven analyte concentrations ranging from 0.12 to 90 nM diluted in running buffer. Obtained sensorgrams were fitted using a 1:1 binding model. The results are shown in Table 8. As can be seen from Table 8, the scFv antibody variable domains based on clone 44-34-C10 exhibit the best overall binding affinities to human IL-4R.

TABLE 8

Affinity of scFvs to human IL-4R.

| Protein ID | scFv Clone ID | Affinity to human IL-4R $k_a$ ($M^{-1} s^{-1}$) | $k_d$ ($s^{-1}$) | $K_D$ (M) |
|---|---|---|---|---|
| PRO1506 | 44-03-A03 -sc01 | 2.17E+06 | 1.49E−04 | 6.89E−11 |
| PRO1524 | 44-03-A03-sc04 | 1.13E+06 | 3.40E−05 | 3.00E−11 |
| PRO1510 | 44-18-C11 -sc01 | 1.67E+06 | 9.58E−04 | 5.75E−10 |
| PRO1528 | 44-18-C11-sc04 | 3.83E+06 | 2.07E−04 | 5.39E−11 |
| PRO1549 | 44-18-C11-sc05 | 1.63E+06 | 1.11E−03 | 6.77E−10 |
| PRO1550 | 44-18-C11-sc06 | 1.55E+06 | 1.32E−03 | 8.52E−10 |
| PRO1551 | 44-18-C11-sc07 | 1.84E+06 | 1.05E−03 | 5.70E−10 |

TABLE 8-continued

Affinity of scFvs to human IL-4R.

| Protein ID | scFv Clone ID | Affinity to human IL-4R $k_a$ ($M^{-1} s^{-1}$) | $k_d$ ($s^{-1}$) | $K_D$ (M) |
|---|---|---|---|---|
| PRO1552 | 44-18-C11-sc08 | 8.41E+06 | 3.54E−04 | 4.21E−11 |
| PRO1553 | 44-18-C11-sc09 | 4.24E+06 | 2.24E−04 | 5.27E−11 |
| PRO1554 | 44-18-C11-sc10 | 2.03E+06 | 1.09E−03 | 5.37E−10 |
| PRO1517 | 44-34-C10 -sc01 | 3.55E+06 | 1.95E−05 | 5.50E−12 |

TABLE 8-continued

Affinity of scFvs to human IL-4R.

| | scFv | Affinity to human IL-4R | | |
|---|---|---|---|---|
| Protein ID | Clone ID | $k_a$ ($M^{-1}$ $s^{-1}$) | $k_d$ ($s^{-1}$) | $K_D$ (M) |
| PRO1535 | 44-34-C10-sc04 | 2.72E+06 | 5.42E−05 | 1.99E−11 |
| PRO1520 | 44-39-B07 -sc01 | 6.18E+05 | 1.18E−02 | 1.91E−08 |
| PRO1538 | 44-39-B07-sc04 | 1.67E+06 | 2.29E−04 | 1.37E−10 |

sc01: CDR graft; sc04: Full graft.

Affinity to Cynomolgus Monkey, Marmoset Monkey and Mouse IL-4R

Cross-reactivity to cynomolgus IL-4R was measured using the same setup as for the analysis of human IL-4R affinities, with the difference that cynomolgus IL-4R-Fc was captured instead of human IL-4R-Fc. To determine affinities for marmoset IL-4R, a direct setup was used since only extracellular domain (ECD) of marmoset IL-4R was available. Marmoset ECD was immobilized directly onto the sensor chip and a titration series of scFvs was injected as analyte. To allow for comparison between KD values obtained for cynomolgus and marmoset IL-4R, affinities to cynomolgus IL-4R ECD were also determined using a direct setup.

Only few scFvs bound to cynomolgus IL-4R ECD. Three scFvs showed cross-reactivity in the capture setup compared to one scFv in the direct setup, meaning that the binding of two scFvs was no longer measurable in the direct setup. This is most likely a consequence of lower KD values determined in the direct setup. The difference was due to the on-rates, which were slower, possibly due to lower accessibility. Off-rates were comparable for all scFvs.

Furthermore, cross-reactivity to marmoset IL-4-R ECD was determined. The results are summarized in Table 9.

Binding to mouse IL-4R was also assessed for scFvs PRO1517, PRO1535 and PRO1538 but none of them showed cross-reactivity.

Stat-6 Reporter Gene Assay in HEK-Blue Cells (Blockage of Human IL-4- and IL-13-Induced Signaling)

The HEK-Blue assay tested the ability of the humanized scFvs to inhibit IL-4- and IL-13-induced signaling via the IL-4R. 50,000 cells per well were seeded in a 96-well plate. Serial dilution of the scFvs and of the control antibody dupilumab were added to the plates in presence of either 0.02 ng/ml IL-4 or 0.3 ng/ml IL-13. After 24 h incubation at 37° C. and 5% $CO_2$, supernatants were transferred to a new plate and secreted embryonic alkaline phosphatase was quantified using the Quanti-Blue substrate.

The scFvs were analyzed in this HEK-Blue assay for their ability to block IL-4R-mediated signaling. The potency of the analyzed molecules was compared to dupilumab. All potency data are summarized in Table 10. Relative $IC_{50}$ values were calculated in mass units (ng/ml) of dupilumab and the scFvs. Eight scFvs blocked IL-4- and IL-13-induced signaling with high potencies. The scFvs based on the clone 44-34-C10 as well as PRO1552 showed best overall blockage potencies. PRO1517, PRO1524, PRO1535, PRO1538 and PRO1552 could block IL-4- and IL-13-induced signaling with a potency similar to dupilumab.

Competitive ELISA (Inhibition of hIL-4 Binding to hIL-4R)

Potency of humanized scFvs was further determined using a competitive ELISA. The potency of each scFv to inhibit the interaction between human IL-4 and human IL-4R was assessed by ELISA using the same procedure as described in EP20216928.0. Similarly, to the stat-6 reporter gene assay, individual $IC_{50}$ values on each plate were calibrated against the $IC_{50}$ of the reference molecule dupilumab.

Seven scFvs inhibited the interaction between human IL-4 and human IL-4R with good to high potency. The scFvs based on clone 44-34-C10 as well as PRO1552 showed the best overall blockage potencies. The blocking potencies of PRO1517 and PRO1552 were similar to dupilumab. On the other hand, PRO1538 showed only moderate inhibition. Five scFv molecules showed no inhibition.

Summary of Pharmacological Characterization of scFvs and Molecule Selection for Developability Assessment The pharmacological characterization of 14 scFvs derived from four different B cell clones provided the basis for selection of molecules for extended biophysical characterization. Five molecules, namely PRO1517, PRO1535, PRO1524, PRO1506 and PRO1538 were selected for further extended characterization based on their overall better performance in terms of neutralization of IL-4- and IL-13-induced signaling in the stat-6 reporter gene assay and in the IL-4/IL-4R-blocking ELISA. All seven molecules showed affinities better than 500 pM. The affinity to cynomolgus monkey IL-4R was lower by a factor of between 4- and 20-fold when compared to human IL-4R, except for three molecules, which showed very low affinity to cynomolgus IL-4R or no binding. In particular, the scFvs based on clone 44-18-C11, i.e. PRO1510, PRO1528 and PRO1549 to PRO1554, showed no binding to cynomolgus IL-4R. Generally, also the affinities of these scFvs to marmoset monkey IL-4R were lower when compared to human IL-4R. As a result of these affinity studies, the scFvs based on clone 44-18-C11, i.e. PRO1510, PRO1528 and PRO1549 to PRO1554 were excluded from further evaluation due to their lack of cross-reactivity to cynomolgus IL-4R, even though PRO1552 showed very good inhibition potencies. For the same reasons, PRO1520 was excluded as well. PRO1538 however, which is based on the same clone 44-39-B07 was not excluded, despite its weak binding affinity towards cynomolgus IL-4R.

1.2.3. Biophysical Characterization of Suitable Anti-IL-4R Binding Domains (scFvs Format)

Manufacture of Material for Stability Measurements

PRO1517 and PRO1538 were produced again using the same manufacturing process as described above at slightly larger scale (0.25 l expression volume) to generate sufficient material for stability assessment. For other proteins which were selected for stability assessment, the amount of previously produced material was sufficient to perform stability assessment. Samples were formulated in 50 mM phosphate-citrate buffer with 150 mM NaCl at pH 6.4 (50 mM NaCiP, pH 6.4) after purification. After purification and dialysis, protein samples were concentrated to ≥10 mg/ml using centrifugal concentration tubes with 5 MWCO as this is the desired concentration to perform storage stability assessment.

Monomer loss upon concentration to 10 mg/ml was between 0 and 12% depending on the molecule as shown in Table 11. Monomeric content of PRO1506 and PRO1524 dropped below 95% which is a critical value for molecules entering storage stability assessment and, therefore, a reason to exclude them from the study. Nevertheless, as the material was already prepared and everything was set up for the study, stability of those molecules was assessed alongside the remaining molecules which exhibited a monomeric content >95% post concentration. The scFvs based on clone 44-34-C10, i.e. PRO1517 and PRO1535, as well as PRO1538 showed virtually no loss of the monomeric content upon concentration.

Storage Stability Study

Humanized scFvs were subjected to stability studies such as a four-week stability study, in which the scFvs were formulated in an aqueous buffer (50 mM NaCiP, 150 mM NaCl, pH 6.4) at 10 mg/ml and stored at <−80° C., 4° C. and 40° C. for four weeks. At the minimum, the fractions of monomers and oligomers in the formulation were evaluated by integration of SE-HPLC peak areas after one week, two weeks and at the end of each study. Additional time points were recorded for most of the molecules. Table 12 compares day 14 (d14) and endpoint measurements obtained at day 28 (d28) of the study.

TABLE 9

Affinity of the scFvs to cynomolgus and marmoset monkey IL-4R.

| Protein | scFv | Affinity to cynomolgus IL-4R capture setup | | | Affinity to cynomolgus IL-4R direct setup | | | Affinity to marmoset IL-4R direct setup | | |
|---|---|---|---|---|---|---|---|---|---|---|
| ID | Clone ID | $k_a$ ($M^{-1}$ $s^{-1}$) | $k_d$ ($s^{-1}$) | $K_D$ (M) | $k_a$ ($M^{-1}$ $s^{-1}$) | $k_d$ ($s^{-1}$) | $K_D$ (M) | $k_a$ ($M^{-1}$ $s^{-1}$) | $k_d$ ($s^{-1}$) | $K_D$ (M) |
| PRO1506 | 44-03-A03 -sc01 | NB | NB | NB | NB | NB | NB | 3.78E+06 | 7.45E-04 | 1.97E-10 |
| PRO1524 | 44-03-A03-sc04 | 1.37E+09 | 8.07E+01 | 5.89E−08 | NB | NB | NB | 2.27E+06 | 2.06E−04 | 9.09E−11 |
| PRO1510 | 44-18-C11 -sc01 | NB | NB | NB | NA | NA | NA | NA | NA | NA |
| PRO1528 | 44-18-C11-sc04 | NB | NB | NB | NB | NB | NB | 6.43E+06 | 4.39E−03 | 6.83E−10 |
| PRO1549 | 44-18-C11-sc05 | NB | NB | NB | NA | NA | NA | NA | NA | NA |
| PRO1550 | 44-18-C11-sc06 | NB | NB | NB | NA | NA | NA | NA | NA | NA |
| PRO1551 | 44-18-C11-sc07 | NB | NB | NB | NA | NA | NA | NA | NA | NA |
| PRO1552 | 44-18-C11-sc08 | NB | NB | NB | NB | NB | NB | 1.57E+07 | 1.28E−03 | 8.16E−11 |
| PRO1553 | 44-18-C11-sc09 | NB | NB | NB | NB | NB | NB | 6.64E+06 | 5.38E−03 | 8.09E−10 |
| PRO1554 | 44-18-C11-sc10 | NB | NB | NB | NA | NA | NA | NA | NA | NA |
| PRO1517 | 44-34-C10 -sc01 | 1.92E+06 | 1.82E−04 | 9.46E−11 | 5.94E+05 | 4.04E−04 | 6.81E−10 | 2.67E+06 | 1.05E−03 | 3.92E−10 |
| PRO1535 | 44-34-C10-sc04 | 1.60E+06 | 2.64E−04 | 1.65E−10 | 6.34E+05 | 2.38E−04 | 3.76E−10 | 3.23E+06 | 2.54E−03 | 7.87E−10 |
| PRO1520 | 44-39-B07 -sc01 | NB | NB | NB | NA | NA | NA | NA | NA | NA |
| PRO1538 | 44-39-B07-sc04 | 5.29E+04 | 8.06E−04 | 1.52E−08 | NB | NB | NB | 1.02E+06 | 1.83E−04 | 1.80E−10 |

NA: not analyzed;

NB: no binding sc01: CDR graft;

sc04: Full graft;

sc05-sc10: Other grafting variant

TABLE 10

Potencies of the scFvs to neutralize IL-4- and IL-13-induced signaling in the stat-6 reporter gene assay.

| Protein | scFv | Neutralization of hIL-4-induced signaling in reporter gene assay | | Neutralization of hIL-13-induced signaling in reporter gene assay | |
|---|---|---|---|---|---|
| ID | Clone ID | $IC_{50}$ [ng/ml] | rel. $IC_{50}$* | $IC_{50}$ [ng/ml] | rel. $IC_{50}$* |
| PRO1506 | 44-03-A03-sc01 | 0.93 | 0.78 | 2.06 | 0.98 |
| PRO1524 | 44-03-A03-sc04 | 0.95 | 0.80 | 1.81 | 1.05 |
| PRO1510 | 44-18-C11-sc01 | no inhibition | n/a | no inhibition | n/a |
| PRO1528 | 44-18-C11-sc04 | 1.49 | 0.28 | 2.29 | 0.59 |
| PRO1549 | 44-18-C11-sc05 | no inhibition | n/a | no inhibition | n/a |
| PRO1550 | 44-18-C11-sc06 | no inhibition | n/a | no inhibition | n/a |
| PRO1551 | 44-18-C11-sc07 | no inhibition | n/a | no inhibition | n/a |
| PRO1552 | 44-18-C11-sc08 | 0.43 | 1.30 | 1.02 | 1.41 |
| PRO1553 | 44-18-C11-sc09 | 1.19 | 0.47 | 6.05 | 0.24 |
| PRO1554 | 44-18-C11-sc10 | no inhibition | n/a | no inhibition | n/a |
| PRO1517 | 44-34-C10-sc01 | 1.44 | 0.39 | 1.83 | 0.57 |
| PRO1535 | 44-34-C10-sc04 | 1.15 | 1.02 | 2.30 | 0.99 |
| PRO1520 | 44-39-B07-sc01 | NA | NA | NA | NA |
| PRO1538 | 44-39-B07-sc04 | 0.64 | 1.83 | 1.69 | 1.35 |

sc01: CDR graft; sc04: Full graft; sc05-sc10: Other grafting variant.

NA: not analyzed

*$IC_{50}$, dupilumab/$IC_{50}$, test sample n/a: relative $IC_{50}$ not calculated (no inhibition or $IC_{50}$ not determined)

TABLE 11

| % monomer loss (SE-HPLC) upon concentration to 10 mg/ml. | | | | |
|---|---|---|---|---|
| Protein ID | Clone ID (scFv) | Initial monomer content [%] | Monomer content post concentration to 10 mg/ml [%] | % loss upon concentration to 10 mg/ml |
| PRO1506 | 44-03-A03 -sc01 | 99.0 | 92.5 | 6.6 |
| PRO1517 | 44-34-C10 -sc01 | 97.6 | 97.4 | 0.2 |
| PRO1524 | 44-03-A03-sc04 | 99.0 | 87.3 | 11.8 |
| PRO1535 | 44-34-C10-sc04 | 99.1 | 99.0 | 0.1 |
| PRO1538 | 44-39-B07-sc04 | 95.0 | 98.2 | −3.4 |

Sc01: CDR graft, sc04: Full graft

As can be depicted from Table 12, the scFvs based on clone 44-34-C10, i.e. PRO1517 and PRO1535, showed a good storage stability at 4° C. The loss of monomeric content after storage at 4° C. for d28 was less than 5%. Also PRO1538 showed a good storage stability at least for 14d. However, none of the stable molecules showed considerable loss of protein content at any temperature.

Freeze-Thaw Stability

In addition to the storage stability study described above, the compatibility of the top performing scFv molecules with respect to freeze-thawing (F/T) cycles (colloidal stability) was assessed. As in the early development stages the drug substance is usually stored frozen, formulation and fill/finish processing will require some freezing and thawing operations.

For the F/T stability assessment the same analytical methods (SE-HPLC, SDS-PAGE) and parameters (% monomer content and % monomer loss) as for the storage stability study were applied to monitor the quality of the molecules over five F/T cycles. Table 13 illustrates the course of % monomer content loss over five F/T cycles. As no dedicated freeze-thaw study was performed, freeze-thaw data obtained with the −80° C. samples of storage stability study, which was acquired over 28 days, is shown. As only four time points could be recorded for some of the proteins, also only four F/T-cycles were done with those proteins.

TABLE 12

28 d storage stability study at 10 mg/ml and temperatures of −80° C., 4° C. and 40° C.

| Protein | Clone ID | Temp. | monomer content [%] | | | % monomer change | | protein concentration [mg/ml] | | | % protein content change | |
|---|---|---|---|---|---|---|---|---|---|---|---|---|
| ID | (scFv) | [° C.] | d 0 | d 14 | d 28 | d 14 | d 28 | d 0 | d 14 | d 28 | d 14 | d 28 |
| PRO1506 | 44-03-A03-sc01 | −80 | 92.5 | 91.9 | 94.1 | −0.6 | 1.7 | 10.1 | 9.8 | NA | −3.0 | NA |
| | | 4 | 92.5 | 92.3 | 92.2 | −0.3 | −0.3 | 10.1 | 9.4 | NA | −6.7 | NA |
| | | 40 | 92.5 | 91.7 | 92.1 | −0.9 | −0.5 | 10.1 | 9.7 | 10.3 | −3.7 | 2.0 |
| PRO1517 | 44-34-C10-sc01 | −80 | 97.4 | 97.1 | 96.8 | −0.4 | −0.7 | 10.0 | 9.9 | 10.9 | −1.5 | 8.4 |
| | | 4 | 97.4 | 96.4 | 95.2 | −1.1 | −2.3 | 10.0 | 7.9 | 11.9 | −21.7 | 18.8 |
| | | 40 | 97.4 | 87.2 | 86.6 | −10.5 | −11.2 | 10.0 | 10.2 | 10.7 | 2.0 | 6.9 |
| PRO1524 | 44-03-A03-sc04 | −80 | 87.3 | 88.7 | 88.9 | 1.6 | 1.8 | 10.5 | 10.3 | 9.6 | −1.9 | −8.1 |
| | | 4 | 87.3 | 89.2 | 88.2 | 2.2 | 1.0 | 10.5 | 10.2 | 9.6 | −2.4 | −8.8 |
| | | 40 | 87.3 | 88.4 | 88.4 | 1.2 | 1.3 | 10.5 | 11.4 | 13.5 | 8.4 | 28.5 |
| PRO1535 | 44-34-C10-sc04 | −80 | 99.0 | 98.5 | 98.1 | −0.5 | −0.9 | 10.5 | 10.9 | 9.6 | 3.3 | −9.1 |
| | | 4 | 99.0 | 96.9 | 95.0 | −2.1 | −4.1 | 10.5 | 10.4 | 7.8 | −1.4 | −25.6 |
| | | 40 | 99.0 | 90.3 | 88.6 | −8.8 | −10.5 | 10.5 | 10.8 | 10.8 | 2.6 | 3.1 |
| PRO1538 | 44-39-B07-sc04 | −80 | 98.2 | 97.8 | NA | −0.3 | NA | 10.4 | 10.5 | NA | 0.6 | NA |
| | | 4 | 98.2 | 96.0 | NA | −2.2 | NA | 10.4 | 10.2 | NA | −2.0 | NA |
| | | 40 | 98.2 | 88.3 | NA | −10.0 | NA | 10.4 | 12.0 | NA | 15.2 | NA |

NA: not analyzed
Sc01: CDR graft,
sc04: Full graft

TABLE 13

F/T stability - monomer content in % and % monomeric change upon repetitive freeze thawing.

| Protein | | monomer content [%] | | | | | | % monomer change | | | | |
|---|---|---|---|---|---|---|---|---|---|---|---|---|
| ID | Clone ID (scFv) | F/T 0 | F/T 1 | F/T 2 | F/T 3 | F/T 4 | F/T 5 | F/T 1 | F/T 2 | F/T 3 | F/T 4 | F/T 5 |
| PRO1506 | 44-03-A03-sc01 | 92.51 | 92.4 | 92.6 | 91.9 | 94.1 | NA* | −0.1 | 0.1 | −0.6 | 1.7 | NA* |
| PRO1517 | 44-34-C10-sc01 | 97.44 | 97.7 | 97.7 | 97.1 | 96.9 | 96.8 | 0.2 | 0.3 | −0.4 | −0.6 | −0.7 |
| PRO1524 | 44-03-A03-sc04 | 87.31 | 85.5 | 85.6 | 88.7 | 88.9 | NA* | −2.1 | −2.0 | 1.6 | 1.8 | NA* |
| PRO1535 | 44-34-C10-sc04 | 98.98 | 99.0 | 98.8 | 98.5 | 98.1 | NA* | 0.0 | −0.2 | −0.5 | −0.9 | NA* |
| PRO1538 | 44-39-B07-sc04 | 98.17 | 98.2 | 98.2 | 97.8 | 97.8 | NA* | 0.0 | 0.0 | −0.3 | −0.4 | NA* |

*not applicable as only 4 time points could be measured
Sc01: CDR graft,
sc04: Full graft

TABLE 14

DSF of selected domains.

| Protein ID | Clone ID (scFv) | Purity SE-HPLC [% monomer] | $T_m$ [° C.] | $T_{onset}$ [° C.] |
|---|---|---|---|---|
| PRO1506 | 44-03-A03-sc01 | 99.0 | 62.8 | 56.7 |
| PRO1517 | 44-34-C10-sc01 | 97.6 | 63.7 | 57.0 |
| PRO1524 | 44-03-A03-sc04 | 99.0 | 59.6 | 54.0 |
| PRO1535 | 44-34-C10-sc04 | 99.1 | 67.9 | 62.7 |
| PRO1538 | 44-39-B07-sc04 | 95.0 | 68.3 | 63.7 |

Sc01: CDR graft, sc04: Full graft

Thermal Unfolding

Thermal unfolding measurements of the five selected scFv constructs were performed using Differential Scanning Fluorimetry (DSF). Resulting midpoint of thermal unfolding ($T_m$) and onset temperature of unfolding calculated at 10% of maximal signal ($T_{onset}$ 10%) values were determined by fitting of data to a Boltzmann equation. Table 14 summarizes calculated melting temperatures measured by DSF. As can be deduced from Table 14, the scFvs based on the clone 44-34-C10 exhibit high melting temperatures of above 63° C. Also, PRO1538 showed a high melting temperature.

Example 2: Generation and Testing of Anti-IL31 Molecules

Aim of the Project

The goal of the project was to generate humanized monoclonal antibody fragments that specifically bind to and neutralize the biological effect of human IL-31. A further goal was to identify anti-IL-31 antibody fragments that are potent and stable enough for incorporation into multispecific antibody formats.

2.1. Generation, Selection, Humanization and Production of the Anti-IL-31 Binding Domains Included in the Multispecific Antibodies of the Present Invention The generation of anti-IL-31 rabbit antibodies, the screening and selection of suitable clones, as well as the humanization and production of the humanized anti-IL-31 binding domains were performed as described in the parallel patent application EP20216938.9, which is herewith incorporated by reference. Anti-IL-31 binding domains that are potent and stable enough for incorporation into multispecific antibody formats were identified and selected based on their biophysical and functional properties. Clone 50-09-D07 was identified to have the overall best biophysical and functional properties.

2.2. Characterization of Suitable Anti-IL-31 Binding Domains

For further characterization of suitable anti-IL-31 binding domains, the following analyses, were performed.

2.2.1. Manufacture of Suitable Anti-IL-31 Binding Domains for Characterization (scFv Format)

Expression of mammalian constructs was performed in CHO—S cells, as described above in section 1.2.1. Manufacture of two scFv sc01 and sc03 constructs (PRO1632 and PRO1643, respectively) originating from one clone, i.e. clone 50-09-D07, is summarized in Table 15.

2.2.2. Pharmacodynamics Characterization of Suitable Anti-IL-31 Binding Domains (scFv Format)

The scFv antibodies that were evaluated as suitable, i.e. PRO1632 and PRO1643, were characterized for primary pharmacodynamics properties.

Affinity to Human and Cynomolgus IL-31

Affinity of the two humanized scFvs to human and cynomolgus IL-31 was determined by SPR analysis on a T200 device (Biacore, GE Healthcare). Cynomolgus IL-31 was manufactured on demand by Sino Biological since it was not available commercially. Human and cynomolgus IL-31-His was captured via an anti-His tag antibody coupled to a carboxylmethylated dextran surface and the scFvs were injected as analyte. After each analyte injection cycle the sensor chip was regenerated and new antigen was captured. The scFvs were measured using a dose response multi-cycle kinetic assay in a high-throughput mode with two concentrations (30 and 10 nM) diluted in running buffer. Obtained sensorgrams were fitted using a 1:1 binding model.

As shown in Table 16, binding to human IL-31 was confirmed for both humanized scFvs.

IL-31RA/OSMR Dimerization Assay (Blockage of Human IL-31-Induced Signaling)

The IL-31RA/OSMR dimerization assay was used to test the ability of the humanized scFvs to inhibit IL-31-induced signaling via the IL-31RA/OSMR heterodimer. 10,000 cells per well were seeded in a 96-well plate. Serial dilutions of the scFvs and of the control antibody BMS-981164 were added to the plates on the next day in presence of 10 ng/ml IL-31. After 6 h incubation at 37° C. and 5% $CO_2$, detection solution was added, the plates were incubated for another hour and luminescence was measured.

The two scFvs were tested in the cellular assay. As described above the potency of the analyzed molecules was compared to BMS-981164.

Relative $IC_{50}$ values were calculated in mass units (ng/ml) of BMS-981164 and the scFvs. The potency data are summarized in Table 17.

TABLE 17

Potencies of scFvs to neutralize IL-31R- and IL-31-induced signaling in IL-31RA/OSMR dimerization assay.

| scFv | | Neutralization of hIL-31-induced signaling in IL-31RA/OSMR dimerization assay | |
|---|---|---|---|
| Protein ID | Clone ID | $IC_{50}$ [ng/ml] | rel. $IC_{50}$* |
| PRO1632 | 50-09-D07-sc01 | 53.29 | 0.20 |
| PRO1643 | 50-09-D07-sc03 | 11.14 | 1.16 |

sc01: CDR graft; sc03: Full graft.

*$IC_{50}$, BMS-981164/$IC_{50}$, test sample

TABLE 15

| scFv manufacture of 2 selected clones. | | | | | | | | |
|---|---|---|---|---|---|---|---|---|
| Protein ID | Clone ID (scFv) | Expression volume [ml] | Yield post affinity chromatography purification [mg] | Yield/l post affinity chromatography purification [mg/l] | Final yield [mg] | Titer [mg/l] | Purity SE-HPLC [% monomer] | Purity SDS-PAGE |
| PRO1632 | 50-09-D07-sc01 | 30 | 5.8 | 193 | 0.7 | 23 | 96.4 | identity confirmed°* |
| PRO1643 | 50-09-D07-sc03 | 30 | 0.7 | 23 | 0.2 | 7 | 90.4 | identity confirmed°* |

°*protein of interest detected only
Sc01: CDR graft,
sc03: Full graft

TABLE 16

| Affinity of scFvs to human IL-31. | | | | | | | |
|---|---|---|---|---|---|---|---|
| Protein | scFv | Affinity to human IL-31 | | | Affinity to cyno IL-31 | | |
| ID | Clone ID | $k_a$ ($M^{-1}$ $s^{-1}$) | $k_d$ ($s^{-1}$) | $K_D$ (M) | $k_a$ ($M^{-1}$ $s^{-1}$) | $k_d$ ($s^{-1}$) | $K_D$ (M) |
| PRO1632 | 50-09-D07-sc01 | 1.02E+06 | 1.26E−03 | 1.24E−09 | 1.52E+06 | 3.06E−03 | 2.01E−09 |
| PRO1643* | 50-09-D07-sc03 | 8.84E+05 | 4.47E−04 | 5.05E−10 | 7.61E+05 | 4.44E−04 | 5.83E−10 |
| PRO1643** | 50-09-D07-sc03 | 8.20E+05 | 5.16E−04 | 6.30E−10 | 7.64E+05 | 4.26E−04 | 5.57E−10 |

*The $K_D$ of PRO1643 has been determined twice. The first $K_D$ (KD 1) has been determined in this first SPR analysis via screening mode.
**The second $K_D$ (KD 2) has been determined in this second SPR analysisusing full titration mode.
sc01: CDR graft;
sc03: Full graft.

Competitive ELISA (Inhibition of hIL-31 Binding to hIL-31RA)

Potency of the two humanized scFvs was further determined using a competitive ELISA. The potency of each scFv to inhibit the interaction between human IL-31 and human IL-31RA was assessed by an ELISA using the same procedure as described in EP20216938.9. Comparably to the IL-31RA/OSMR dimerization assay, individual $IC_{50}$ values on each plate were calibrated against the $IC_{50}$ of the reference molecule BMS-981164. The Full graft scFv inhibited the interaction between human IL-31 and human IL-31RA with similar potency when compared to BMS-981164. The potency data are summarized in Table 18.

TABLE 18

| Potencies of scFvs to inhibit the interaction between IL-31 and IL-31R. | | | |
|---|---|---|---|
| | scFv | Potency in IL-31/IL-31RA ELISA | |
| Protein ID | Clone ID | $IC_{50}$ [ng/ml] | rel. $IC_{50}$* |
| PRO1632 | 50-09-D07-sc01 | 22.91 | 0.41 |
| PRO1643 | 50-09-D07-sc03 | 4.58 | 2.04 |

sc01: CDR graft; sc03: Full graft.
*$IC_{50}$, BMS-981164/$IC_{50}$, test sample Summary of Pharmacological Characterization of scFvs and Molecule Selection for Detailed Biophysical Evaluation The pharmacological characterization of the two scFvs provided the basis for selection of molecules for detailed biophysical evaluation. Based on these results, PRO1643 was selected for detailed biophysical evaluation based on its overall better performance.

2.2.3 Biophysical Characterization of Suitable Anti-IL-31 Binding Domains (scFv Format)

Manufacture of Stability Material

PRO1643 was produced again using the same manufacturing process as described above at slightly larger scale (0.25 l expression volume) to generate sufficient material for stability assessment. Samples were formulated in 50 mM phosphate-citrate buffer with 150 mM NaCl at pH 6.4 (50 mM NaCiP, pH 6.4). The protein was concentrated to >10 mg/ml using centrifugal concentration tubes with 5MWCO after purification and dialysis.

Monomer loss upon concentration to 10 mg/ml was 0.1% as shown in Table 19.

TABLE 19

| % monomer loss (SE-HPLC) upon concentration to 10 mg/ml. | | | | |
|---|---|---|---|---|
| Protein ID | Clone ID (scFv) | Initial monomer content [%] | Monomer content post concentration to 10 mg/ml [%] | % loss upon concentration to 10 mg/ml |
| PRO1643 | 50-09-D07-sc03 | 98.3 | 98.2 | 0.1 |

Sc03: Full graft

Storage Stability Study

PRO1643 was subjected to stability studies such as a four-week stability study, in which the scFv was formulated in an aqueous buffer (final buffer, 50 mM NaCiP, 150 mM NaCl, pH 6.4) at 10 mg/ml and stored at <−80° C., 4° C. and 40° C. for four weeks. The fractions of monomers and oligomers in the formulation were evaluated by integration of SE-HPLC peak areas at different time points of the study. Further, protein concentration was determined by $UV_{280}$ measurement at different time points. Table 20 compares d14 and endpoint measurements obtained at d28 of the study.

PRO1643 showed no considerable loss of monomeric content at 4° C. and d28 of the study. PRO1643 showed no considerable loss of protein content at any temperature.

Freeze-Thaw Stability

In addition to the storage stability study described above, the compatibility of PRO1643 with respect to freeze-thawing (F/T) cycles (colloidal stability) was assessed.

For the F/T stability assessment the same analytical methods (SE-HPLC, UV-Vis) and parameters (% monomer content and % monomer loss) as for the storage stability study were applied to monitor the stability of the molecules over three F/T cycles. Table 21 illustrates the course of monomer content in % and % monomer content loss over three F/T cycles. As no dedicated freeze-thaw study was performed, freeze-thaw data obtained with the −80° C. samples of storage stability study which was acquired over 28 days is shown in the table below. As only three time points could be recorded per sample, freeze-thaw stability data is available for three F/T-cycles only.

Thermal Unfolding

Thermal unfolding measurement of PRO1643 has been performed using Differential Scanning Fluorimetry (DSF). Resulting midpoint of thermal unfolding ($T_m$) and onset temperature of unfolding calculated at 10% of maximal signal ($T_{onset}$ 10%) values has been determined by fitting of data to a Boltzmann equation. Table 22 summarizes calculated melting temperatures measured by DSF.

Example 3: Selection and Optimization of Anti-IL-4R Molecules for Multispecific Format

3.1. General Remarks on the Selection of Anti-IL-4R Domains

The anti-IL-4R domains PRO1517 (44-34-C10-sc01) and PRO1535 (44-34-C10-sc04) were selected in the first place, since they exhibit very good pharmacodynamic properties and an acceptable to good stability. PRO1538 (44-39-B07-sc04) was selected as well, albeit having improvable pharmacological properties, since it showed the best stability. PRO1517 (44-34-C10-sc01) was subjected to a stability optimization and PRO1538 (44-39-B07-sc04) was subjected to pI balance optimization, as shown below in 3.2.

The anti-IL-4R binding domains applied in the final multispecific antibodies showed exclusive cross-reactivity to cynomolgus and marmoset monkey.

3.2. Optimization of Anti-IL-4R Domains

The anti-IL-4R domains PRO1538 (44-39-B07-sc03) and PRO1517 (44-34-C10-sc01) were further optimized for assembly into multispecific formats.

TABLE 20

28 d storage stability study at 10 mg/ml and temperatures of −80° C., 4° C. and 40° C.

| Protein ID | Clone ID (scFv) | Temp. [° C.] | monomer content [%] d 0 | d 14 | d 28 | % monomer change d 14 | d 28 | protein concentration [mg/ml] d 0 | d 14 | d 28 | % protein content change d 14 | d 28 |
|---|---|---|---|---|---|---|---|---|---|---|---|---|
| PRO1643 | 50-09-D07-sc03 | −80 | 98.2 | 98.3 | 99.2 | 0.1 | 1.0 | 10.6 | 12.4 | 12.1 | 23.2 | 20.4 |
| | | 4 | 98.2 | 98.2 | 99.0 | −0.1 | 0.7 | 10.6 | 11.9 | 10.3 | 18.4 | 2.6 |
| | | 40 | 98.2 | 97.2 | 97.8 | −1.0 | −0.4 | 10.6 | 12.1 | 13.0 | 20.6 | 29.1 |

Sc03: Full graft

TABLE 21

F/T stability - monomer content in % and % monomeric change upon repetitive freeze thawing.

| Protein ID | Clone ID (scFv) | monomer content [%] F/T 0 | F/T 1 | F/T 2 | F/T 3 | % monomer change F/T 1 | F/T 2 | F/T 3 |
|---|---|---|---|---|---|---|---|---|
| PRO1643 | 50-09-D07-sc03 | 98.2 | 98.2 | 98.3 | 99.2 | −0.1 | 0.1 | 1.0 |

Sc03: Full graft

TABLE 22

DSF measurement of selected scFv domains.

| Protein ID | Clone ID (scFv) | Purity SE-HPLC [% monomer] | $T_m$ [° C.] | $T_{onset}$ 10% [° C.] |
|---|---|---|---|---|
| PRO1643 | 50-09-D07-sc03 | 90.4* | 69.5 | 64.3 |

Sc03: Full graft
*initial material with 90.4% monomer content used for measurement Optimization of Anti-IL-4R Domain 44-39-B07-Sc04 (PRO1538)

PRO1538 (44-39-B07-sc03) has a pI imbalance between VL and VH ($pI_{VL}$=8.2 and $pI_{VH}$=5.0). Imbalance in pI correlates with high viscosity and could negatively influence stability. Therefore, two new variants of this molecule were designed. These variants are described below. Briefly, all residues in VH have been analyzed in detail with the aim to design molecules with removed pI imbalance and without compromising binding affinity and without introducing critical sequence liabilities (chemical and post-translational modifications), T cell epitopes etc.

Two variants were designed, which are summarized in Table 23.

These variants of PRO1538 (44-39-B07-sc03) did, however, not show the desired improvement of stability. Since PRO1538 is significantly less potent in inhibiting IL-4- and IL-13-induced signaling, and has a more than 10-fold lower potency in blocking the interaction of IL-4 to IL-4R than PRO1517, PRO1538 and its variants were excluded from further consideration and efforts were focused on the improvement of RPO1517 (44-34-C10-sc01).

TABLE 23

| Optimization variants for 44-39-B07-sc03 | | | | |
|---|---|---|---|---|
| Protein ID | Construct | Optimization Aim | Mutations VL | Mutations VH |
| PRO2097 | 44-39-B07-sc05 | pI balance | I2V, A51P, P75S, G82R, F89Y | V2E, A25R, R82S, Y105F, T143R |
| PRO2098 | 44-39-B07-sc06 | pI balance | I2V, A51P, P75S, G82R, F89Y | V2E, A24R, R82S, Y105F, T143R |

Optimization of Anti-IL-4R Domain 44-34-C10-Sc01 (PRO1517)

PRO1517 (44-34-C10-sc01) is an anti-IL-4R scFv with favorable binding characteristics. During biophysical characterization the scFv PRO1517 exhibited good but yet still improvable solubility. Efforts were made to further improve PRO1517 with respect to solubility, long-term stability and concentration behavior. Therefore, four new variants of this molecule were designed. These variants are described below. Briefly, hydrophobic patches in CDRs or in the former VH-CH interface have been analyzed in detail and pI imbalance has been reduced with the aim to design molecules with removed hydrophobic patches without compromising binding affinity and without introducing critical sequence liabilities (chemical and post-translational modifications), T cell epitopes etc.

Four variants were designed, which are summarized in Table 24.

TABLE 24

| Optimization variants for 44-34-C10-sc01 | | | | |
|---|---|---|---|---|
| Protein ID | Construct | Optimization Aim | Mutations VL | Mutations VH |
| PRO1896 | 44-34-C10-sc06 | Solubility, stability | | L12R, V103T, L144Q |
| PRO1897 | 44-34-C10-sc07 | Solubility, stability | Y72S | |
| PRO1898 | 44-34-C10-sc08 | Solubility, stability | S14R, T87R | |
| PRO1899 | 44-34-C10-sc09 | Solubility, stability, affinity | | L12R, V103T, L144Q + RDNSKN changed to KASST (AHo 82-87) |

3.3 Biophysical Characterization of Optimized Anti-IL-4R Binding Domains (scFv Format)

Storage Stability Study

PRO1897, PRO1898 and PRO1899 were subjected to storage stability studies as decribed above in section 1.2.3. The results are summarized in Table 25.

As can be depicted from Table 25, the scFvs PRO1897, PRO1898 and PRO1899 exhibit excellent storage stability. The loss of monomeric content after storage at 4° C. for 28 days was less than 5%. Also, none of these molecules showed considerable loss of protein content at any temperature.

Thermal Unfolding

Thermal stability of PRO1897, PRO1898 and PRO1899 was analyzed by nano dynamic scanning fluorimetry (nDSF) using a NanoTemper, allowing the determination of the onset of unfolding ($T_{onset}$), midpoint of unfolding ($T_{m1}$) and scattering onset temperature. $T_{m1}$ and $T_{onset}$ results of duplicate/triplicate measurements are summarized in Table 26. As can be deduced from Table 26, PRO1897, PRO1898 and PRO1899 exhibit high melting temperatures.

TABLE 25

| 28 d storage and F/T stability study at 10 mg/ml and temperatures of −80° C., 4° C. and 40° C. | | | | | | | | | | | | |
|---|---|---|---|---|---|---|---|---|---|---|---|---|
| Protein | | Temp. | monomer content [%] | | | % monomer change | | protein concentration [mg/ml] | | | % protein content change | |
| ID | Clone ID (scFv) | [° C.] | d 0 | d 1 | d 28 | d 1 | d 28 | d 0 | d 1 | d 28 | d 1 | d 28 |
| PRO1897 | 44-34-C10-sc07 | −80 | 97.7 | 97.7* | NA | −0.1* | NA | 10.2 | 10.5* | NA | 2.2* | NA |
| | | 4 | 97.7 | 98 | 97 | −0.1 | −0.3 | 10.2 | 10 | 11 | 0.3 | 3.6 |
| | | 40 | 97.7 | 95 | 87 | −2.6 | −10.8 | 10.2 | 11 | 13 | 2.6 | 30.0 |
| PRO1898 | 44-34-C10-sc08 | −80 | 97.4 | 97.3* | NA | −0.1* | NA | 10.2 | 10.4* | NA | 1.8* | NA |
| | | 4 | 97.4 | 97 | 96 | −0.1 | −1.1 | 10.2 | 10 | 10 | −0.3 | −1.7 |
| | | 40 | 97.4 | 93 | 86 | −4.4 | −11.8 | 10.2 | 10 | 11 | −1.7 | 9.7 |

TABLE 25-continued 28 d storage and F/T stability study at 10 mg/ml and temperatures of −80° C., 4° C. and 40° C.

| Protein ID | Clone ID (scFv) | Temp. [° C.] | monomer content [%] d 0 | d 1 | d 28 | % monomer change d 1 | d 28 | protein concentration [mg/ml] d 0 | d 1 | d 28 | % protein content change d 1 | d 28 |
|---|---|---|---|---|---|---|---|---|---|---|---|---|
| PRO1899 | 44-34-C10-sc09 | −80 | 98.1 | 98.0* | NA | 0.0* | NA | 10.5 | 10.7* | NA | 1.9* | NA |
| | | 4 | 98.1 | 98 | 98 | −0.1 | 0.0 | 10.5 | 10 | 11 | −0.2 | 1.8 |
| | | 40 | 98.1 | 97 | 84 | −0.6 | −14.3 | 10.5 | 11 | 13 | 2.9 | 28.8 |

NA: not analyzed;
*Five repeated F/T cycles were performed prior to measurement

TABLE 26 nDSF of optimized domains.

| Protein ID | Clone ID (scFv) | Purity SE-HPLC [% monomer] | $T_{m1}$ [° C.] | $T_{onset}$ [° C.] |
|---|---|---|---|---|
| PRO1897 | 44-34-C10-sc07 | 98.0 | 70.4 | 65.7 |
| PRO1898 | 44-34-C10-sc08 | 98.0 | 76.0 | 67.0 |
| PRO1899 | 44-34-C10-sc09 | 98.7 | 71.3 | 64.9 |

3.4. Pharmacodynamic Characterization of Optimized Anti-IL-4R Binding Domains (scFv Format)

Affinity to Human IL-4R

Affinity of the optimized anti-IL-4R scFvs PRO1898 and PRO1899 to human IL-4R was determined by SPR analysis on a T200 device (Biacore, GE Healthcare), as described above in section 1.2.2. The scFvs were measured using a dose response multi-cycle kinetic assay with seven analyte concentrations ranging from 0.12 to 90 nM diluted in running buffer. Obtained sensorgrams were fitted using a 1:1 binding model.

As shown in Table 27, binding to human IL-4R and cynomolgus IL-4R was confirmed for all optimized scFvs.

TABLE 27

Affinity of optimized anti-IL-4R scFvs to human IL-4R.

| scFv Protein ID | Clone ID | Affinity to human IL-4R $k_a$ ($M^{-1}$ $s^{-1}$) | $k_d$ ($s^{-1}$) | $K_D$ (M) |
|---|---|---|---|---|
| PRO1898 | 44-34-C10-sc08 | 2.15E+06 | 1.70E−05 | 7.91E−12 |
| PRO1899 | 44-34-C10-sc09 | 2.95E+06 | 2.04E−05 | 6.92E−12 |

Affinity to Cynomolgus IL-4R

Affinity of the optimized anti-IL-4R scFvs PRO1898 and PRO1899 to cynomolgus IL-4R was measured using the same setup as for the analysis of human IL-4R affinities, with the difference that cynomolgus IL-4R-Fc was captured instead of human IL-4R-Fc, as described above in section 1.2.2. The results of this analysis are summarized in Table 28.

TABLE 28

Affinity of the optimized anti-IL-4R scFvs to cynomolgus IL-4R.

| scFv Protein ID | Clone ID | Affinity to cynomolgus IL-4R capture setup $k_a$ ($M^{-1}$ $s^{-1}$) | $k_d$ ($s^{-1}$) | $K_D$ (M) |
|---|---|---|---|---|
| PRO1898 | 44-34-C10-sc08 | 1.20E+06 | 1.09E−04 | 9.08E−11 |
| PRO1899 | 44-34-C10-sc09 | 1.1E+07 | 1.4E−04 | 1.2E−11 |

Stat-6 Reporter Gene Assay in HEK-Blue Cells (Blockage of Human IL-4- and IL-13-Induced Signaling)

The optimized anti-IL-4R scFvs PRO1898 and PRO1899 were analyzed in this HEK-Blue assay for their ability to block IL-4R mediated signaling, as described above in section 1.2.2. The potency of the analyzed molecules was compared to dupilumab. All potency data are summarized in Table 29. Relative $IC_{50}$ values were calculated in mass units (ng/ml) of dupilumab and the scFvs. The optimized scFvs blocked IL-4- and IL-13-induced signaling with high potencies similar to dupilumab (see FIG. 3).

TABLE 29

Potencies of the scFvs PRO1898 and PRO1899 to neutralize IL-4 and IL-13 induced signaling in the stat-6 reporter gene assay.

| scFv Protein ID | Clone ID | Neutralization of hIL-4 induced signaling in reporter gene assay $IC_{50}$ [ng/ml] | rel. $IC_{50}$* | Neutralization of hIL-13 induced signaling in reporter gene assay $IC_{50}$ [ng/ml] | rel. $IC_{50}$* |
|---|---|---|---|---|---|
| Dupilumab | NA | 1.15 | 1.00 | 1.00 | 1.00 |
| PRO1898 | 44-34-C10-sc08 | 1.00 | 1.15 | 1.15 | 0.87 |
| PRO1899 | 44-34-C10-sc09 | 0.71 | 1.61 | 0.56 | 1.80 |

*$IC_{50}$, dupilumab/$IC_{50}$, test sample
NA: not applicable

Competitive ELISA (Inhibition of hIL-4 Binding to hIL-4R)

Potency of the optimized anti-IL-4R scFvs PRO1898 and PRO1899 scFvs was determined using a competitive ELISA. The potency of each scFv to inhibit the interaction between human IL-4 and human IL-4R was assessed by ELISA as described in section 1.2.2. Similarly, to the stat-6 reporter gene assay, individual $IC_{50}$ values on each plate were calibrated against the $IC_{50}$ of the reference molecule dupilumab.

The results of the competitive ELISA analysis are summarized in Table 30. The blocking potencies of PRO1898 and PRO1899 were similar to dupilumab (see FIG. 4).

TABLE 30

Potency of the scFvs PRO1898 and PRO1899 to inhibit the hIL-4 - IL-4R interaction in a competition ELISA assay.

| | scFv | Inhibition in hIL-4 - IL-4R competition ELISA | |
|---|---|---|---|
| Protein ID | Clone ID | $IC_{50}$ [ng/ml] | rel. $IC_{50}$* |
| Dupilumab | NA | 6.78 | 1.00 |
| PRO1898 | 44-34-C10-sc08 | 3.41 | 1.95 |
| Dupilumab | NA | 6.18 | 1.00 |
| PRO1899 | 44-34-C10-sc09 | 2.98 | 2.07 |

*$IC_{50}$, dupilumab/$IC_{50}$, test sample;
NA: not applicable

Example 4: Selection and Optimization of Anti-IL31 Molecules for Multispecific Format 4.1. General Remarks on the Selection of Anti-IL-31 Domains The anti-IL-31 domain PRO1643 (50-09-D07-sc03) was selected in the first place for further development, since it exhibits the desired pharmacodynamic properties as well as an excellent stability. Nevertheless, the anti-IL-31 binding domain PRO1643 (50-09-D07-sc03) underwent further solubility improving as shown below in 4.2.

The anti-IL-31 binding domains applied in the final multispecific antibodies do cross-react with cynomolgus monkey IL-31.

4.2. Optimization of Anti-IL-31 Domains

The anti-IL-31 domain PRO1643 (50-09-D07-sc03) was further optimized for assembly into multispecific format.

Optimization of Anti-IL-31 Domain 50-09-D07-Sc03

PRO1643 (50-09-D07-sc03) is a very stable anti-IL-31 scFv, however, efforts were nevertheless made to improve it with respect to solubility, long-term stability and concentration behavior. Therefore, new variants of this molecule were designed. These variants are described below. Briefly, hydrophobic patches in CDRs or in the former VH-CH interface have been analyzed in detail with the aim to design molecules with removed hydrophobic patches without compromising binding affinity and without introducing critical sequence liabilities (chemical and post-translational modifications), T cell epitopes etc.

Four variants were designed, which are summarized in Table 31.

TABLE 31

Optimization variants for 50-09-D07-sc03

| Protein ID | Construct | Optimization Aim | Mutations VL | Mutations VH |
|---|---|---|---|---|
| PRO1900 | 50-09-D07-sc04 | Solubility, stability | — | L12R, V103T, L144Q |
| PRO1901 | 50-09-D07-sc05 | Solubility, stability | — | L12S, V103T, L144Q |
| PRO1902 | 50-09-D07-sc06 | Solubility, stability | — | Y59S |
| PRO1903 | 50-09-D07-sc07 | Solubility, stability, sequence liability (DS) | D32E | — |

4.3. Biophysical Characterization of Optimized Anti-IL-31 Binding Domains (scFv Format) Storage Stability Study PRO1900, PRO1901, PRO1902 and PRO1903 were subjected to storage stability studies as decribed above in section 1.2.3. except that the last readout was taken at day 14 and F/T as well as that stability at −80° C. was not assessed. The results are summarized in Table 32.

As summarized in Table 32, scFvs PRO1900, PRO1901, PRO1902 and PRO1903 exhibited excellent storage stability. The loss of monomeric content after storage at 4° C. for 14 days was less than 0.2%, and <3% after storage at 40° C. for 14 days. Also, none of these molecules showed considerable loss of protein content at any temperature and data point.

Thermal Unfolding

Thermal stability of PRO1900, PRO1901, PRO1902 and PRO1903 was analyzed by nano dynamic scanning fluorimetry (nDSF) using a NanoTemper, allowing the determination of the onset of unfolding ($T_{onset}$), midpoint of unfolding ($T_{m1}$) and scattering onset temperature. $T_{m1}$ and $T_{onset}$ results of duplicate/triplicate measurements are summarized in Table 33. As can be deduced from Table 33, PRO1900, PRO1901, PRO1902 and PRO1903 exhibited high melting temperatures.

4.4. Pharmacodynamics Characterization of Optimized Anti-IL-31 Binding Domains (scFv Format)

Affinity to Human IL-31

Affinity of PRO1643 and of the optimized anti-IL-31 scFvs to human IL-31 was determined by SPR analysis on a T200 device (Biacore, GE Healthcare), as described above in section 2.2.2. The scFvs were measured using a dose response multi-cycle kinetic assay in a high-throughput mode with two concentrations (30 and 10 nM) diluted in running buffer. Obtained sensorgrams were fitted using a 1:1 binding model.

As shown in Table 34, binding to human IL-31 and cynomolgus IL-31 was confirmed for all optimized scFvs.

Path Hunter IL-31RA/OSMR Dimerization Assay (Blockage of Human IL-31-Induced Signaling)

PRO1643 and the optimized scFvs were tested for their ability to inhibit IL-31-induced signaling via the IL-31RA/OSMR heterodimer by using an IL-31RA/OSMR dimerization assay. The assay was performed as described above. The potency of the analyzed molecules was compared to BMS-981164.

Relative $IC_{50}$ values were calculated in mass units (ng/ml) of BMS-981164 and the scFvs. The potency data are summarized in Table 35. As can be depicted from Table 35, PRO1643 as well as the optimized variants PRO1900, PRO1901 and PRO1903 could potently neutralize IL-31-induced signaling. The mutations introduced in the variant PRO1902 to optimize solubility and stability obviously resulted in the disruption of the ability to inhibit IL-31-induced signaling.

TABLE 32

14 d storage stability study at 10 mg/ml at temperatures of 4° C. and 40° C.

| Protein | | Temp. | monomer content [%] | | | % monomer change | | protein concentration [mg/ml] | | | % protein content change | |
|---|---|---|---|---|---|---|---|---|---|---|---|---|
| ID | Clone ID (scFv) | [° C.] | d 0 | d 1 | d 14 | d 1 | d 14 | d 0 | d 1 | d 14 | d 1 | d 14 |
| PRO1900 | 50-09-D07-sc04 | 4 | 99.8 | NA | 99.8 | NA | 0.0 | 9.8 | NA | 10.0 | NA | 2.6 |
| | | 40 | 99.8 | 99.3 | 98.9 | −0.5 | −0.9 | 9.8 | 10.1 | 10.1 | 3.4 | 3.5 |
| PRO1901 | 50-09-D07-sc05 | 4 | 97.0 | NA | 97.0 | NA | −0.0 | 10.5 | NA | 10.9 | NA | 3.6 |
| | | 40 | 97.0 | 96.9 | 96.3* | −0.1 | −0.7* | 10.5 | 10.1 | 10.9* | −3.7 | 4.0* |
| PRO1902 | 50-09-D07-sc06 | 4 | 98.5 | NA | 98.4 | NA | 0.0 | 9.3 | NA | 9.4 | NA | 0.9 |
| | | 40 | 98.5 | 97.2 | 95.8 | −1.3 | −2.7 | 9.3 | 9.3 | 9.4 | 0.7 | 1.4 |
| PRO1903 | 50-09-D07-sc07 | 4 | 98.7 | NA | 98.7 | NA | −0.1 | 9.6 | NA | 10.1 | NA | 4.5 |
| | | 40 | 98.7 | 98.2 | 97.7 | −0.5 | −1.1 | 9.6 | 9.8 | 9.9 | 1.2 | 2.3 |

*sample incubated for first 7 days at 25° C. instead of 40° C.

NA: not analyzed

TABLE 33 nDSF of optimized anti-IL-31 binding domains (scFv format).

| Protein ID | Clone ID (scFv) | Purity SE-HPLC [% monomer] | $T_{m1}$ [° C.] | $T_{onset}$ [° C.] |
|---|---|---|---|---|
| PRO1900 | 50-09-D07-sc04 | 99.8 | 70.7 | 60.5 |
| PRO1901 | 50-09-D07-sc05 | 97.7 | 69.0 | 52.3 |
| PRO1902 | 50-09-D07-sc06 | 98.3 | 73.8 | 62.5 |
| PRO1903 | 50-09-D07-sc07 | 98.9 | 71.1 | 55.6 |

TABLE 34

Affinity of scFvs to human and cynomolgus IL-31.

| Protein | scFv | Affinity to human IL-31 | | | Affinity to cynomolgus IL-31 | | |
|---|---|---|---|---|---|---|---|
| ID | Clone ID | $k_a$ ($M^{-1}$ $s^{-1}$) | $k_d$ ($s^{-1}$) | $K_D$ (M) | $k_a$ ($M^{-1}$ $s^{-1}$) | $k_d$ ($s^{-1}$) | $K_D$ (M) |
| PRO1643 | 50-09-D07-sc03 | 5.79E+05 | 6.53E−04 | 1.13E−09 | 5.01E+05 | 5.87E−04 | 1.17E−09 |
| PRO1900 | 50-09-D07-sc04 | 6.61E+05 | 5.99E−04 | 9.07E−10 | 5.54E+05 | 5.94E−04 | 1.07E−09 |
| PRO1901 | 50-09-D07-sc05 | 5.91E+05 | 5.65E−04 | 9.56E−10 | 5.01E+05 | 5.69E−04 | 1.14E−09 |
| PRO1902 | 50-09-D07-sc06 | 8.52E+05 | 2.46E−03 | 2.89E−09 | 7.31E+05 | 2.47E−03 | 3.38E−09 |
| PRO1903 | 50-09-D07-sc07 | 5.24E+05 | 6.38E−04 | 1.22E−09 | 4.34E+05 | 6.05E−04 | 1.39E−09 |

Sc03: Full graft,
sc04 to sc07: other grafting variants

TABLE 35

Potencies of scFvs to neutralize IL-31R- and IL-31-induced signaling in IL-31RA/OSMR dimerization assay.

| scFv | | Neutralization of hIL-31-induced signaling in IL-31RA/OSMR dimerization assay | |
|---|---|---|---|
| Protein ID | Clone ID | $IC_{50}$ [ng/ml] | rel. $IC_{50}$* |
| PRO1643 | 50-09-D07-sc03 | 8.078 | 0.85 |
| PRO1900 | 50-09-D07-sc04 | 8.209 | 0.73 |
| PRO1901 | 50-09-D07-sc05 | 8.071 | 0.78 |
| PRO1902 | 50-09-D07-sc06 | 371.3 | 0.03 |
| PRO1903 | 50-09-D07-sc07 | 7.982 | 1.49 |

Sc03: Full-graft,
sc04 to sc07: other grafting variants
*$IC_{50}$, BMS-981164/$IC_{50}$, test sample Example 5: Anti-IL-4R×IL-31 bispecific antibodies based on Morrison-H IgG1-Fc-silenced 5.1. Morrison-H Design The Morrison format (also IgG-$(scFv)_2$ format) is a bivalent and bispecific IgG-based molecular format comprising an Fc region and two scFv domains that are either fused via linkers to the C-termini of the heavy chains, commonly referred to as Morrison-H format (see FIG. 2A), or that are fused via linkers to the C-termini of the light chains, commonly referred to as Morrison-L format (see FIG. 2B).

In a first series of anti-IL-4R×IL-31 bispecific antibodies, a Morrison-H format was chosen, wherein the Fc region is derived from the IgG subclass IgG1 that has been silenced by the double mutation Leu234Ala and Leu235Ala, also generally referred to as the "LALA mutation". Two highly stable λ-capped scFvs domains were fused to the heavy chain C-terminus.

In total, 19 bispecific antibodies having the above-mentioned Morrison-H format were designed, bearing the anti-IL-4R domains on the Fab-arms except for one molecule. 13 different anti-IL-4R domains derived from 5 clones and three anti-IL-31 domains derived from two clones were combined. Nine of these bispecific Morrison-H antibodies exhibited good pharmacological properties. These Morrison-H antibodies are summarized in Table 36.

TABLE 36

Overview of Morrison-H molecule architecture

| PRO ID | Fab-arm domains | Constant | scFv-domains | Linkers |
|---|---|---|---|---|
| PRO1929 | 44-34-C10-sc01 | kappa/IgG1 (silent) | 50-09-D07-sc03 | $(G_4S)_4$ |
| PRO1930 | 44-18-C11-sc08 | kappa/IgG1 (silent) | 50-09-D07-sc03 | $(G_4S)_4$ |
| PRO1982 | 44-18-C11-sc08 | kappa/IgG1 (silent) | 50-09-D07-sc03 | $(G_4S)_2$ |
| PRO2077 | 44-18-C11-sc14 | kappa/IgG1 (silent) | 50-09-D07-sc04 | $(G_4S)_2$ |
| PRO2078 | 44-18-C11-sc18 | kappa/IgG1 (silent) | 50-09-D07-sc04 | $(G_4S)_2$ |
| PRO1973 | 44-39-B07-sc04 | kappa/IgG1 (silent) | 50-09-D07-sc04 | $(G_4S)_2$ |
| PRO2079 | 44-39-B07-sc05 | kappa/IgG1 (silent) | 50-09-D07-sc04 | $(G_4S)_2$ |
| PRO2080 | 44-39-B07-sc06 | kappa/IgG1 (silent) | 50-09-D07-sc04 | $(G_4S)_2$ |
| PRO1977 | 44-03-A03-sc04 | kappa/IgG1 (silent) | 50-09-D07-sc04 | $(G_4S)_2$ |

5.2. Morrison-H Molecule Production

Expression of multispecific constructs was performed in FreeStyle CHO-S cells using the transient CHOgro expression system (Mirus). The genes of interest were optimized for mammalian expression, synthesized and cloned into a standard pcDNA3.1 vector. Expression cultures were cultivated in batch using shaking flasks for 6 to 7 days (cell viability <70%) at 37° C. Expression temperature was lowered to 32° C. after 1 day of expression of all molecules listed in Table 37 except for PRO1982, PRO2078 and PRO2080 which were kept at 37° C. over the whole expression period. The culture supernatants were separated from cells by centrifugation followed by a 0.22 μm sterile filtration. The target proteins were captured from the clarified culture supernatants by Protein L or A affinity chromatography followed by a size-exclusion chromatography polishing step (in case no fractions with a suitable monomeric content as assessed by SE-HPLC were available post capture already). For the quality control of the manufactured material standard analytical methods, such as SE-HPLC, SDS-PAGE, and $UV_{280}$ were used.

Table 37 shows a production overview of these molecules. All molecules were finalized with a monomeric content >98% after a SEC polishing step.

TABLE 37

Production overview of Morrison-H molecules

| Protein ID | Format | Fab-arm domain | scFv-domain | Expression titer post capture [mg/l] | Final titer [mg/l] | Purity SE-HPLC [% monomer] |
|---|---|---|---|---|---|---|
| PRO1929 | Morrison-H | 44-34-C10-sc01 | 50-09-D07-sc03 | 33.2 | 19.4 | 99.2 |
| PRO1930 | Morrison-H | 44-18-C11-sc08 | 50-09-D07-sc03 | 16.9 | 7.4 | 98.4 |
| PRO1982 | Morrison-H | 44-18-C11-sc08 | 50-09-D07-sc03 | 22.9 | 14.2 | 98.2 |
| PRO2077 | Morrison-H | 44-18-C11-sc14 | 50-09-D07-sc04 | 19.1 | 11.6 | 99.4 |
| PRO2078 | Morrison-H | 44-18-C11-sc18 | 50-09-D07-sc04 | 18.6 | 9.7 | 98.9 |
| PRO1973 | Morrison-H | 44-39-B07-sc04 | 50-09-D07-sc04 | 37.2 | 18* | 98.1 |
| PRO2079 | Morrison-H | 44-39-B07-sc05 | 50-09-D07-sc04 | 43.1 | 19.6 | 99.4 |

TABLE 37-continued

Production overview of Morrison-H molecules

| Protein ID | Format | Fab-arm domain | scFv-domain | Expression titer post capture [mg/l] | Final titer [mg/l] | Purity SE-HPLC [% monomer] |
|---|---|---|---|---|---|---|
| PRO2080 | Morrison-H | 44-39-B07-sc06 | 50-09-D07-sc04 | 34.4 | 16.3 | 99.2 |
| PRO1977 | Morrison-H | 44-03-A03-sc04 | 50-09-D07-sc04 | 21.8 | 11.8* | 98.5 |

*calculated/extrapolated value as not all material was used for polishing step 5.3. Biophysical and Pharmacological Characterization Nine multispecific molecules, i.e. PRO1929, PRO1930, PRO1982 and its improved variants PRO2077 and PRO2078; PRO1973 and its improved variants PRO2079 and PRO2080; and PRO1977, were selected for further characterization.

The nine molecules were subjected to an extended biophysical characterization to determine suitability for process and formulation development. These molecules were characterized by a range of methods to assess melting and aggregation temperatures, solubility at concentrations over 150 g/l, loss of monomer content after 2 weeks at 4° and 25° C., increase in hydrodynamic radius and charge variants and clipping of the proteins. Solubility was also assessed by PEG screen. For PRO1929, loss of monomer content and the increase of hydrodynamic radius were determined.

Based on these results PRO2077, PRO2080, PRO1977, PRO1929 are the best constructs. They harbor the anti-IL-4R domains 44-18-C11-sc14, 44-39-09-sc06, 44-03-A04-sc03 and 44-34-C10-sc01, respectively and the anti-IL-31 domain 50-09-D07-sc04. The intended target concentration of 150 g/I was reached for all molecules. In terms of monomeric stability during storage at 4° C. and 25° C., PRO1929 and PRO2080 had the best profile. With respect to chemical stability and process development PRO2077 and PRO2080 showed a good pH stability and low charge variant complexity.

From a pharmacological perspective, PRO2077 shows a 2-fold superior potency to block IL-4- and IL-13-induced signaling when compared to dupilumab. The anti-IL-4R domain in this molecule does not cross-react with cynomolgus IL-4R. PRO2080, PRO1977 and PRO1929 block IL-4R-signaling approximately 2- to 3-fold less potently than dupilumab. PRO2080 and PRO1977 appear to show cross-reactivity to cynomolgus IL-4R based on avidity binding. A variant of PRO1929 could function as surrogate. PRO1929 exhibits a strong cross-reactivity to cynomolgus IL-4R and similar potency to inhibit IL-4R-signaling when compared to PRO2080 and PRO1977. All molecules potently block IL-31-induced signaling and are cross-reactive to cynomolgus IL-31. Furthermore, all molecules exhibit picomolar affinities for both human targets.

Example 6: Anti-IL-4R×IL-31 Bispecific Antibodies Based on Morrison-H and Morrison-L IgG4

6.1. Morrison Format Design

In a second series of anti-IL-4R×IL-31 bispecific antibodies, Morrison-H and Morrison-L format were chosen, wherein the Fc region is derived from the IgG subclass IgG4. Two highly stable λ-capped scFvs domains were fused to the C-termini of the heavy chain (Morrison-H) or the light chain (Morrison-L).

Based upon cynomolgus monkey cross-reactivity, excellent potency and excellent biophysical properties, constructs including the IL-4R and IL-31 domains of the PRO1929 family were prioritized.

Two variants of the PRO1929 family IL-4R binder were included in the reformatting of the molecules mentioned above, these were 44-34-C10-sc08 and 44-34-C10-sc09. The same IL-31 binding domain was included in all constructs and this was 50-09-D07-sc04.

In total, seven IgG4-$(scFv)_2$ molecules were designed, four Morrison-H and three Morrison-L molecules. Two different anti-IL-4R domains derived from one clone and one anti-IL-31 domain were combined, as shown in Table 38 (Morrison-H) and Table 39 (Morrison-L).

TABLE 38

IgG4 Morrison-H constructs

| PRO ID | Fab-arm domain | Constant | scFv-domain |
|---|---|---|---|
| PRO2198 | 44-34-C10-sc08 | IgG4 (S228P) | 50-09-D07-sc04 |
| PRO2199 | 44-34-C10-sc09 | IgG4 (S228P) | 50-09-D07-sc04 |
| PRO2200 | 50-09-D07-sc04 | IgG4 (S228P) | 44-34-C10-sc08 |
| PRO2201 | 50-09-D07-sc04 | IgG4 (S228P) | 44-34-C10-sc09 |

TABLE 39

IgG4 Morrison-L constructs

| PRO ID | Fab-arm domain | Constant | scFv-domain |
|---|---|---|---|
| PRO2206 | 44-34-C10-sc08 | IgG4 (S228P) | 50-09-D07_sc04 |
| PRO2207 | 44-34-C10-sc09 | IgG4 (S228P) | 50-09-D07_sc04 |
| PRO2208 | 44-34-C10-sc09 | IgG4 (S228P) | 50-09-D07_sc04 |

6.2. Assessment of Binding Affinities and Specificities by SPR

Affinity to Human and Cyno IL-4R

Binding kinetics (including affinity) of the bispecific Morrison-H (PRO2198, PRO2199) and Morrison-L (PRO2206, PRO2207) molecules to recombinant human IL-4R protein (ECD with His Tag, Sino Biological) were determined by SPR analysis on a T200 device (Biacore, Cytiva). In this SPR experiment, Morrison molecules were captured via an anti-human IgG-Fc antibody (Human Antibody Capture Kit; Biacore, Cytiva) covalently immobilized to a carboxylmethylated dextran surface (CM5 sensorchip; Biacore, Cytiva) and a titration series of human IL-4R ECD was injected as analyte. After each analyte injection cycle, the sensor chip was regenerated ($MgCl_2$), and new Morrison antibody was subsequently re-captured. The binding kinetics to human IL-4R was measured using a multi-cycle kinetic assay, with nine analyte concentrations ranging from 0.175 to 45 nM diluted in running buffer (HEPES buffered saline, 0.05% Tween-20, pH 7.5). The apparent dissociation ($k_d$) and association ($k_a$) rate constants and the apparent dissociation equilibrium constant ($K_D$) were calculated with the Biacore analysis software (Biacore Evaluation software Version 3.2, Cytiva) using one-to-one Langmuir binding model and quality of the fits was monitored based on Chi2 and U-value, which are measures for the quality of the curve fitting. The binding level was calculated as the maximum stability binding achieved normalized to the theoretical Rmax. Cross-reactivity to cynomolgus monkey IL-4R was measured using the same setup as for the analysis of human IL-4R kinetics, with the difference that recombinant cynomolgus monkey IL-4R (ECD with His-tag, Acro Biosystems) protein was used as analyte instead of human IL-4R.

As shown in Table 40 high affinity binding to human IL-4R was demonstrated for the Morrison-H and Morrison-L antibodies. The calculated $K_D$ values are very similar ranging from 291 pM to 48 pM, with Morrison-H antibody PRO2198 having 291±136 pM affinity for binding to human IL-4R. Kinetic affinities to cynomolgus monkey IL-4R are also similar among the tested molecules (209 to 11 pM), with 144±49 pM affinity measured for PRO2198 Morrison-H antibody, thus demonstrating cross-reactivity of all the molecules to IL-4R of cynomolgus monkey origin.

Affinity to Human and Cyno IL-31

Binding kinetics (including affinity) of the bispecific Morrison-H (PRO2198, PRO2199) and Morrison-L (PRO2206, PRO2207) molecules to recombinant human IL-31 protein (Peprotech) were determined by SPR analysis on a T200 device (Biacore, Cytiva). In this SPR experiment, Morrison antibodies were injected over a carboxylmethylated dextran surface (CM5 sensorchip; Biacore, Cytiva) immobilized with human recombinant IL-4R protein (ECD with Fc Tag, R&D Systems) and a titration series of human IL-31 was injected as analyte. The affinity to human IL-31 was measured using a single-cycle kinetic assay with injections of five sequential analyte concentrations, ranging from 0.05 to 30 nM diluted in running buffer (HEPES buffered saline, 0.05% Tween-20, pH 7.5), without regeneration of the sensorchip surface after injection of the analyte. The calculation of the kinetics and the apparent dissociation equilibrium constant ($K_D$) as well as the measurement for the quality of curve fitting were done as described above for IL-4R. The binding level was calculated as the maximum stability binding achieved normalized to the theoretical Rmax. Cross-reactivity to cynomolgus monkey IL-31 was measured using the same setup as for the analysis of human IL-31 affinities, with the difference that recombinant cynomolgus monkey IL-31 (ECD with His Tag, Sino Biological) protein was used as analytes instead of human IL-31.

A prerequisite of the SPR setup employed to measure binding kinetics to recombinant IL-31 is the capture of Morrison-H and Morrison-L antibodies via immobilized human IL-4R. All previously tested Morrison antibodies showed stable binding to immobilized human IL-4R, and thus the setup was proven valid. The rationale to use this SPR setup is to guarantee a homogeneous orientation of the captured Morrison molecules, while minimizing steric hindrance for the IL-31 binding site.

After having shown a stable capture of Morrison antibodies via recombinant human IL-4R protein, IL-31 was injected as analyte and the kinetics of the binding of IL-31 to captured Morrison molecules were calculated. As shown in Table 41, all tested Morrison-H and Morrison-L molecule bind to human IL-31 and cynomolgus monkey IL-31 with similar affinities (152 to 52 pM and 169 to 103 pM, respectively). PRO2198 Morrison-H antibody demonstrated binding to human IL-31 with a calculated $K_D$ of 52±18 pM and binding to recombinant cynomolgus monkey IL-31 protein with a binding affinity of 10±1 pM, therefore confirming good cross-reactivity.

Concomitant Binding to Human IL-4R and IL-31 and to Cyno IL-4R and IL-31

Concomitant binding of Morrison-H and Morrison-L antibodies was assessed by SPR analysis on a T200 device (Biacore, Cytiva). As described above, binding of Morrison antibodies to IL-31 (both human and cynomolgus monkey) is best measured when the Morrison antibody is captured on the sensorchip surface via IL-4R interaction, due to homogenous molecular orientation of the antibody as well as minimal steric hindrance of IL-31 binding sites. Therefore, concomitant binding of the tested Morrisons to both human IL-4R and human IL-31 was assessed by injecting the Morrison antibodies over a carboxylmethylated dextran surface (CM5 sensorchip; Biacore, Cytiva) immobilized with human recombinant IL-4R protein (Fc Tag, R&D Systems), followed by injecting a single high concentration (45 nM) of human IL-31 as analyte. PRO2199, PRO2206 and PRO2207 concomitant binding was assessed during the kinetic measurement of human IL-31 as reported above, by using the binding levels from the injection of human IL-31 at 45 nM. Concomitant binding of PRO2198 to both cynomolgus monkey IL-4R and cynomolgus monkey IL-31 was measured similarly to human IL-4R and human IL-31, except for using recombinant cynomolgus monkey IL-4R (ECD with His-tag, Acro Biosystems) immobilized on the sensorchip surface and recombinant cynomolgus monkey IL-31 (ECD with His Tag, Sino Biological) protein as analyte.

Concomitant binding to human IL-4R and human IL-31 was demonstrated by SPR for all tested Morrison antibodies, i.e. PRO2198, PRO2199, PRO2206 and PRO2207, as exemplarily shown for PRO2198 in FIG. 5. For PRO2198, also concomitant binding to cynomolgus monkey IL-4R and cynomolgus monkey IL-31 was shown (see FIG. 5).

TABLE 40

Binding kinetics of Morrison antibodies to human IL-4R and cynomolgus monkey IL-4R

| Protein | Fab arm | scFv domain | Affinity by SPR measurement | | | |
|---|---|---|---|---|---|---|
| ID | Clone ID | Clone ID | Antigen | $k_a$ ($M^{-1}$ $s^{-1}$) | $k_d$ ($s^{-1}$) | $K_D$ (M) |
| PRO2198 | 44-34-C10-sc08 | 50-09-D07-sc04 | human IL-4R | 3.52E+05 | 1.01E−04 | 2.91E−10 |
| PRO2199 | 44-34-C10-sc09 | 50-09-D07-sc04 | human IL-4R | 2.93E+05 | 5.76E−05 | 1.97E−10 |
| PRO2206 | 44-34-C10-sc08 | 50-09-D07-sc04 | human IL-4R | 4.09E+05 | 1.95E−05 | 4.77E−11 |
| PRO2207 | 44-34-C10-sc09 | 50-09-D07-sc04 | human IL-4R | 2.44E+05 | 4.61E−05 | 1.89E−10 |
| PRO2198 | 44-34-C10-sc08 | 50-09-D07-sc04 | cynomolgus IL-4R | 3.70E+05 | 4.90E−05 | 1.44E−10 |
| PRO2199 | 44-34-C10-sc09 | 50-09-D07-sc04 | cynomolgus IL-4R | 9.80E+05 | 3.44E−05 | 3.51E−11 |
| PRO2206 | 44-34-C10-sc08 | 50-09-D07-sc04 | cynomolgus IL-4R | 1.16E+05 | 2.42E−05 | 2.09E−10 |
| PRO2207 | 44-34-C10-sc09 | 50-09-D07-sc04 | cynomolgus IL-4R | 2.53E+06 | 2.77E−05 | 1.10E−11 |

TABLE 41

Binding kinetics of Morrison antibodies to human IL-31 and cynomolgus monkey IL-31

| Protein ID | Fab arm Clone ID | scFv domain Clone ID | Affinity by SPR measurement Antigen | $k_a$ ($M^{-1}$ $s^{-1}$) | $k_d$ ($s^{-1}$) | $K_D$ (M) |
|---|---|---|---|---|---|---|
| PRO2198 | 44-34-C10-sc08 | 50-09-D07-sc04 | human IL-31 | 2.75E+05 | 1.60E−05 | 5.20E−11 |
| PRO2199 | 44-34-C10-sc09 | 50-09-D07-sc04 | human IL-31 | 2.51E+05 | 1.75E−05 | 6.97E−11 |
| PRO2206 | 44-34-C10-sc08 | 50-09-D07-sc04 | human IL-31 | 2.20E+05 | 2.36E−05 | 1.07E−10 |
| PRO2207 | 44-34-C10-sc09 | 50-09-D07-sc04 | human IL-31 | 1.63E+05 | 2.47E−05 | 1.52E−10 |
| PRO2198 | 44-34-C10-sc08 | 50-09-D07-sc04 | cynomolgus IL-31 | 9.92E+04 | <1.00E−05 | 1.03E−10 |
| PRO2199 | 44-34-C10-sc09 | 50-09-D07-sc04 | cynomolgus IL-31 | 8.10E+04 | <1.00E−05 | 1.23E−10 |
| PRO2206 | 44-34-C10-sc08 | 50-09-D07-sc04 | cynomolgus IL-31 | 5.93E+04 | <1.00E−05 | 1.69E−10 |
| PRO2207 | 44-34-C10-sc09 | 50-09-D07-sc04 | cynomolgus IL-31 | 6.09E+04 | <1.00E−05 | 1.64E−10 |

6.3. Binding to Human or Cynomolgus IL-4R-Expressing Cells (FACS)

To test binding of the Morrison-H and Morrison-L antibodies PRO2198, PRO2199, PRO2206 and PRO2207 to human or cynomolgus IL-4R-expressing HEK293T cells, HEK293T cells were transfected with human and cynomolgus IL-4R plasmids and mock plasmid using Lipofectamine3000. Binding of an antibody targeting V5 Tag, which is fused to the N-terminus of human and cynomolgus IL-4R expression constructs, would confirm successful expression of both targets and was thus used as a positive control for plasma membranous binding. The Morrison-H molecule PRO2077 was used as negative control for cynomolgus IL-4R binding since this molecule had not shown any cross-reactivity to cynomolgus IL-4R (see section 5.3).

50,000 transfected HEK293T cells per well were seeded in a 96-well plate. 5-fold serial dilutions of the Morrison-H and Morrison-L antibodies PRO2198, PRO2199, PRO2206 and PRO2207 and of the control molecule PRO2077, which is not cross-reactive to cynomolgus IL-4R, were added at concentrations ranging from 5,000 to 0.32 ng/ml to the plates and incubated for 60 min at 4° C. on a shaker. Supernatants were removed and detection reagent was added for flow cytometry analysis. The geometric mean of the APC fluorescence intensity of single cells was calculated.

All potency data are summarized in Table 42. Mean relative $IC_{50}$ values from repeated analysis are indicated in pM. Morrison-H and Morrison-L antibodies PRO2198, PRO2199, PRO2206 and PRO2207 efficiently bound to human and cynomolgus IL-4R on transfected HEK293T cells (see FIG. 6).

6.4. Potency Assessment to Inhibit Human IL-4 and IL-13 Signaling (HEK-Blue™ IL-4™ L-13 Cells Stat-6 Reporter Gene Assay)

The HEK-Blue assay has been used to test the ability of the Morrison-H and Morrison-L antibodies PRO2198, PRO2199, PRO2206 and PRO2207 to inhibit IL-4- and IL-13-induced signaling via IL-4R. 50,000 cells per well were seeded in a 96-well plate. Three-fold serial dilutions of the Morrison molecules and of the reference antibody dupilumab at concentrations ranging from 100 to 0.002 ng/ml were added to the plates in presence of either 0.05 ng/ml IL-4 or 0.3 ng/ml IL-13. After 24 h incubation at 37° C. and 5% $CO_2$, supernatants were transferred to a new plate and secreted embryonic alkaline phosphatase was quantified using the Quanti-Blue substrate. The Morrison-H and Morrison-L antibodies PRO2198, PRO2199, PRO2206 and PRO2207 were also tested for inhibition of IL-4-induced signaling with an excess of IL-31 (10 nM) in the assay medium.

Figure 8:
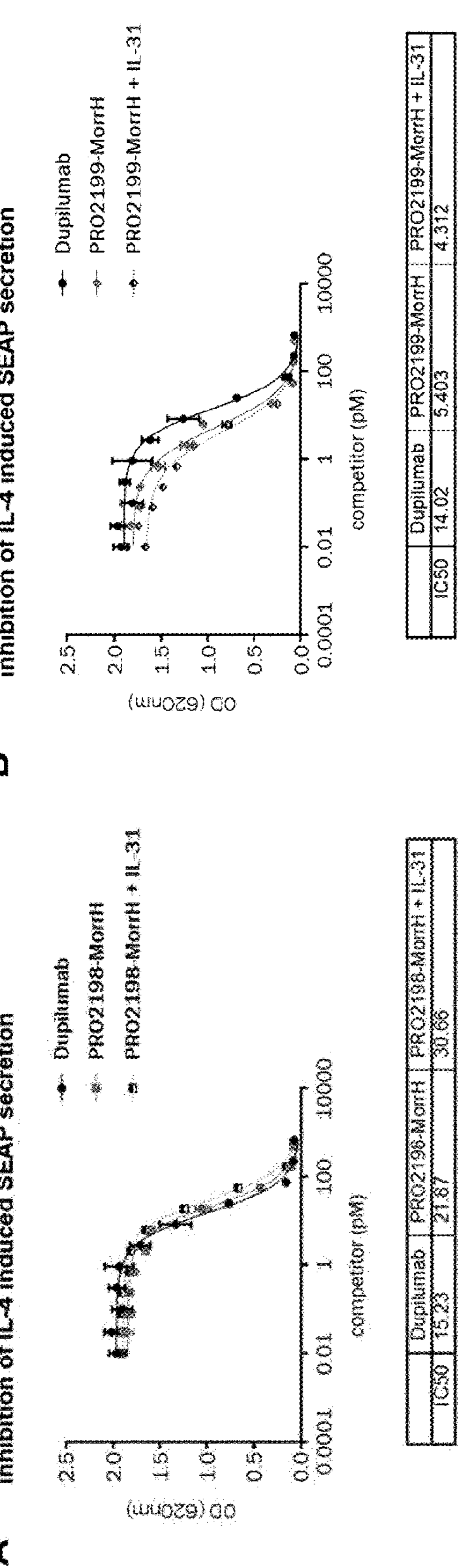
FIG. 8 shows the potencies of Morrison-H (MorrH) antibodies PRO2198 (A) and PRO2199 (B) to neutralize human IL-4-induced signaling in the stat-6 reporter gene assay with or without an excess of IL-31 in the assay medium. No potency loss is observed in presence of an excess of IL-31. The $IC_{50}$ values depicted in the FIGS. 6A and 6B represent single point measurements.

All potency data are summarized in Table 43 (IL-4/IL-4R inhibition) and Table 44 (IL-13/IL-4R inhibition). Mean relative $IC_{50}$ values from repeated analyses are also indicated in pM. Morrison-H and Morrison-L antibodies PRO2198, PRO2199, PRO2206 and PRO2207 efficiently blocked the interaction between IL-4 or IL-13 and IL-4R, with comparable potency to dupilumab (see FIG. 7). Efficient IL-4R blockage was maintained when IL-31 was bound to the anti-IL-31 domains of the Morrison-H molecules (see FIG. 8).

6.5. Potency Assessment to Inhibit Human IL-31-Induced Receptor Dimerization (PathHunter® eXpress IL31RA/OSMRb Assay)

PathHunter IL-31RA/OSMRb Dimerization Assay

In the IL-31RA/OSMR dimerization assay the ability of the Morrison-H and Morrison-L antibodies PRO2198, PRO2199, PRO2206 and PRO2207 to inhibit IL-31-induced signaling via the IL-31RA/OSMR heterodimer was assessed. 10,000 cells per well were seeded in a 96-well plate. 3-fold serial dilutions of the molecules and of the control antibody BMS-981164 at concentrations ranging from 1,000 to 0.2 ng/ml were added to the plates on the next day in presence of 10 ng/ml IL-31. After 6 h incubation at 37° C. and 5% CO2, detection solution was added, the plates were incubated for another hour and luminescence was measured. All antibodies were also tested for inhibition of IL-31-induced signaling with an excess of IL-4R (at 50 nM) in the assay medium.

Inhibition of Human IL-31

Figure 9:
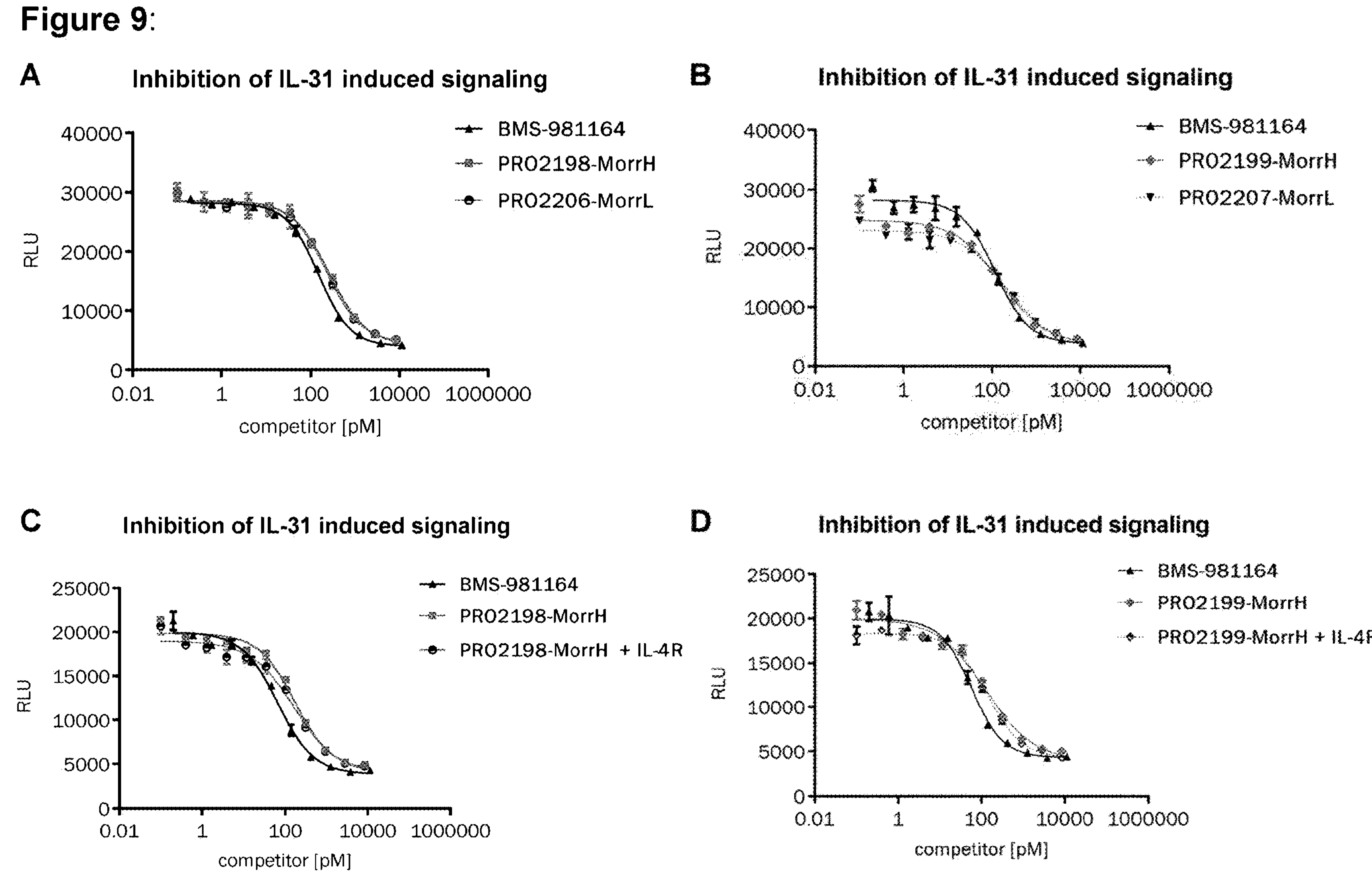
FIG. 9 shows the potencies of Morrison-H (MorrH) and Morrison-L (MorrL) antibodies PRO2198, PRO2199, PRO2206 and PRO2207 to neutralize human IL-31-induced signaling in the IL-31 RA/OSMR dimerization assay with or without an excess of IL-4R extracellular domain in the assay medium. The Morrison antibodies blocked the interaction between IL-31 and IL-31 RA with similar potency when compared to BMS-981164 (A and B). No potency loss was determined in presence of an excess of IL-4R (C and D).

In Table 45, a summary of all potency data is shown. Mean relative $IC_{50}$ values from repeated analysis are indicated in pM. All Morrison-H and Morrison-L antibodies inhibited IL-31-induced signaling with similar potency when compared to BMS-981164. Efficient blockage of the interaction of IL-31 with IL-31R was maintained when the anti-IL-4R domains were bound to IL-4R (see FIG. 9).

Inhibition of Cynomolgus IL-31

Figure 10:
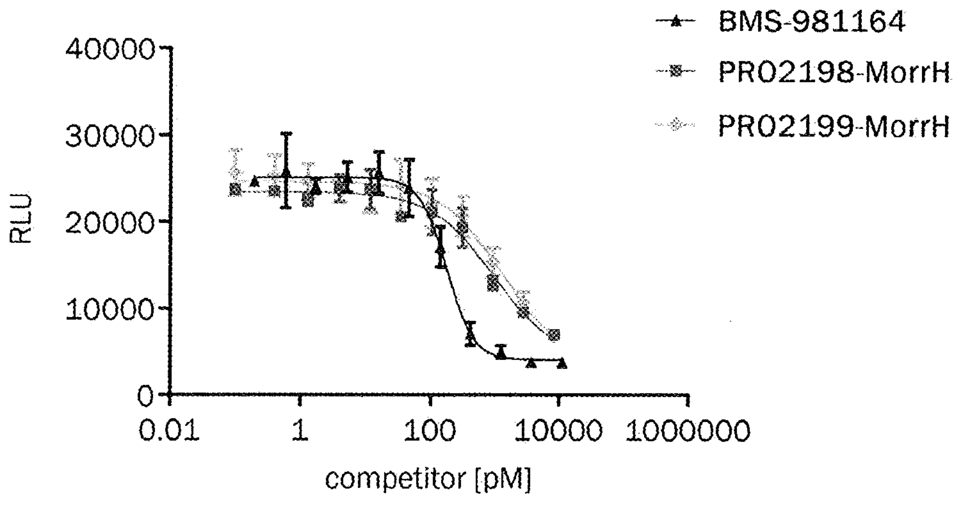
FIG. 10 shows the potency of the Morrison-H antibodies PRO2198 and PRO2199 to neutralize cynomolgus IL-31-induced signaling in the IL-31RA/OSMR dimerization assay. The antibodies PRO2198 and PRO2199 were able to block the interaction between cynomolgus IL-31 and IL-31RA.

To assess inhibition of signaling induced by cynomolgus IL-31, the IL-31RA/OSMR dimerization assay was used as described above with the difference that 10 ng/ml cynomolgus IL-31 were used instead of 10 ng/ml human IL-31, and only the Morrison-H antibodies PRO2198 and PRO2199 were tested for inhibition. Both PRO2198 and PRO2199 efficiently blocked the interaction between cynomolgus IL-31 and human IL-31RA (see FIG. 10).

6.6. Potency Assessment for Simultaneous Inhibition of Human IL-4 and IL-31 Signaling (BEAS-2B Assay; CCL2)

To assess potency of the Morrison-H antibodies PRO2198 and PRO2199 to inhibit both IL-4- and IL-31-induced signaling simultaneously, a cell-based assay using BEAS-2B (Human bronchial epithelial) cells with a Sandwich ELISA for readout was implemented. In this assay, blockage of both signaling pathways results in decreased CCL2 secretion by BEAS-2B cells.

25,000 cells per well were seeded in 96 well plate in 100 μl growth medium and incubated overnight at 37° C. with 5% $CO_2$. The following day, cells were washed and 1 ng/ml IL-4 and 10 ng/ml IL-31 were added with serial dilutions of a combination of dupilumab and BMS-981164 or of the Morrison-H antibodies PRO2198 or PRO2199. The cells were then incubated for 24 h, supernatants were collected, and the concentration of secreted CCL-2 was measured by means of a Sandwich ELISA adapted from a commercial kit.

The BEAS-2B assay is the only available assay that allows for the assessment of the combined inhibition of IL-4 and IL-31. Both PRO2198 and PRO2199 were able to simultaneously block IL-4 and IL-31 signaling with similar potency when compared to the combination of dupilumab and BMS-981164. They reached a level of inhibition comparable to the combination of the reference molecules (see FIG. 1).

6.7. Potency Assessment to Inhibit Human IL-4-Induced CD23 Upregulation on Human PBMC Subsets Human PBMCs were used to assess IL-4-induced upregulation of CD23 in monocytes and naïve and memory B cells. Human PBMC were isolated from fresh whole blood according to an adapted Leucosep protocol, using Leucosep tubes with an integrated porous barrier and gradient density centrifugation.

400,000 PBMCs per well were seeded in a 96-well plate in 100 ml assay medium. Three-fold serial dilutions of the Morrison-H antibodies PRO2198 and PRO2199, of the reference anti-IL-4R IgG4 antibodies PRO2209 and PRO2210, which have no anti-IL-31 scFv domains attached, and of the reference antibody dupilumab at concentrations ranging from 10,000 to 0.169 ng/ml were added to the plates in presence of 2 ng/ml IL-4. After 48 h incubation at 37° C. and 5% $CO_2$, PBMCs were stained for flow cytometry analysis using mouse anti-human CD19-PE, mouse anti-human CD14-PerCP/Cy5.5, mouse anti-human CD14-PerCP/Cy5.5 and mouse anti-human CD23-APC dyes. Following FACS analysis, the geometric mean of gated CD23 monocytes, CD23 naïve B cells and CD23 memory B cells was used for calculations. A four-parameter logistic (4PL) curve fit was applied to calculate $IC_{50}$ values of inhibition-curve using GraphPad Prism software.

PBMC assay data are summarized in Table 46. $IC_{50}$ values obtained for different blood donors are shown in picomolar. The Morrison-H antibodies PRO2198 and PRO2199 as well as the reference IgG4 antibodies PRO2209 and PRO2210 showed similar potency when compared to dupilumab to inhibit IL-4-induced upregulation of CD23 in monocytes and naïve and memory B cells. When formatted as IgG4 molecules without the anti-IL-31 domains attached, the molecules blocked IL-4-induced signaling with the same potency when compared to dupilumab (see FIG. 11). Thus, the addition of the anti-IL-31 domains has little effect on IL-4 inhibition potency.

6.8. Potency Assessment to Inhibit Human IL-4-Induced TARC Production in Human Whole Blood To determine potency of inhibiting IL-4-induced secretion of thymus activation regulated chemokine (TARC, also CCL17), a whole blood assay based on a commercial ELISA as readout was used. Blockage of both signaling pathways leads to decreased TARC levels in whole blood.

Whole human peripheral blood collected in sterile tubes containing the anticoagulant EDTA was used for the assay. 160 μl per well of serial dilutions of dupilumab, PRO2198 or PRO2199 ranging from 64,800 to 1.10 pM were added to a 96 well plate with round bottom wells with either 1 ng/ml IL-4 or 1 ng/ml IL-13. Following addition of 40 μl whole blood per well, the plates were incubated for 24 h at 37° C. with 5% $CO_2$. On the next day, the plates were centrifuged for 10 min at 1,000 g, supernatants were collected and frozen at −20° C. The supernatants were then analyzed using the human TARC/CCL17 DuoSet ELISA Kit from R&D systems, and TARC levels were determined.

The TARC assay was performed with blood from three different donors for IL-4-induced TARC secretion. PRO2198 and PRO2199 neutralized IL-4-induced TARC in human whole blood with a potency comparable to dupilumab, i.e. with $IC_{50}$ values of less than 500 pM.

Example 7: Biophysical Characterization

The Morrison-H and Morrison-L antibodies PRO2198, PRO2199, PRO2206 and PRO2207 were subjected to several biophysical characterization procedures. The following biophysical properties were investigated:

1. Confirmation of identity
2. Multi-pH stress study
   a. Chemical stability and charge heterogeneity
   b. Thermal stability
3. High concentration feasibility (HCF) study 7.1. Confirmation of identity:

Mass Determination

Masses were analyzed by intact mass analysis using ESI-MS. All tested Morrison-H and Morrison-L antibodies, i.e. PRO2198, PRO2199, PRO2206 and PRO2207, showed the expected masses for the light chain and the heavy chain. In addition, the heavy chain shows the expected glycosylation. The determined mass for each Morrison antibody is shown in Table 47.

TABLE 42

Plasma membranous binding to human and cynomolgus IL-4R on transfected HEK293T-cells.

| | | | | Human IL-4R | | Cynomolgus IL-4R | |
|---|---|---|---|---|---|---|---|
| PRO ID | Fab-arm domain | Constant | scFv-domain | $EC_{50}$ [nM] | rel. $IC_{50}$ rel. $EC_{50}$ ($EC_{50}$ V5 antibody/ $EC_{50}$ sample) | $EC_{50}$ [nM] | rel. $IC_{50}$ rel. $EC_{50}$ ($EC_{50}$ V5 antibody/ $EC_{50}$ sample) |
| PRO2198 | 44-34-C10-sc08 | IgG4 (S228P) | 50-09-D07-sc04 | 1.11 | 3.31 | 0.97 | 21.56 |
| PRO2199 | 44-34-C10-sc09 | IgG4 (S228P) | 50-09-D07-sc04 | 0.85 | 4.33 | 1.78 | 11.73 |
| PRO2206 | 44-34-C10-sc08 | IgG4 (S228P) | 50-09-D07-sc04 | 0.83 | 4.46 | 0.90 | 23.18 |
| PRO2207 | 44-34-C10-sc09 | IgG4 (S228P) | 50-09-D07-sc04 | 0.60 | 6.15 | 0.65 | 32.22 |
| PRO2077 | 44-18-C11-sc14 | kappa/IgG1 (silent) | 50-09-D07-sc04 | 0.60 | 6.18 | no binding | no binding |

TABLE 43

Potencies of the Morrison-H and Morrison-L antibodies to neutralize human IL-4-induced signaling in the stat-6 reporter gene assay without and with IL-31 in the assay medium.

| PRO ID | Fab-arm domain | scFv-domain | Mean $IC_{50}$ [pM] | Mean rel. $IC_{50}$ [$IC_{50}$ dupilumab/ $IC_{50}$ sample] | Retained $IC_{50}$ with and without IL-31 excess (n = 1) [$IC_{50}$, no IL-31/$IC_{50}$, with IL-31] ng/ml values |
|---|---|---|---|---|---|
| PRO2198 | 44-34-C10-sc08 | 50-09-D07-sc04 | 23.9** | 0.42 | 0.71 |
| PRO2199 | 44-34-C10-sc09 | 50-09-D07-sc04 | 11.5** | 0.72 | 1.25 |
| PRO2206* | 44-34-C10-sc08 | 50-09-D07-sc04 | 11.8 | 0.45 | not measured |
| PRO2207* | 44-34-C10-sc09 | 50-09-D07-sc04 | 9.4 | 0.52 | not measured |

N = number of repeated analyses.
*$IC_{50}$ or relative $IC_{50}$ (single analysis)/NA: not applicable
**average value

TABLE 44

Potencies of the Morrison-H and Morrison-L molecules to neutralize human IL-13-induced signaling in the stat-6 reporter gene assay.

| PRO ID | Fab-arm domain | scFv-domain | Mean $IC_{50}$ [pM] | Mean rel. $IC_{50}$ [$IC_{50}$ dupilumab/ $IC_{50}$ sample] |
|---|---|---|---|---|
| PRO2198 | 44-34-C10-sc08 | 50-09-D07-sc04 | 22.1** | 0.42 |
| PRO2199* | 44-34-C10-sc09 | 50-09-D07-sc04 | 11.3 | 0.69 |
| PRO2206* | 44-34-C10-sc08 | 50-09-D07-sc04 | 29.5 | 0.26 |
| PRO2207* | 44-34-C10-sc09 | 50-09-D07-sc04 | 12.6 | 0.62 |

N = number of repeated analyses.
*$IC_{50}$ or relative $IC_{50}$ (single analysis)/NA: not applicable
**average value.

TABLE 45

Potencies of the Morrison-H and Morrison-L molecules to neutralize human IL-31-induced signaling in IL-31RA/OSMR dimerization assay without and with IL-4R in the medium.

| PRO ID | Fab-arm domain | scFv-domain | Mean $IC_{50}$ [pM] | Mean rel. $IC_{50}$ [$IC_{50}$ BMS-981164/ $IC_{50}$ sample] | Retained $IC_{50}$ with and without IL-4R excess (n = 1) [$IC_{50}$, no IL-4R/$IC_{50}$, with IL-4R] ng/ml values |
|---|---|---|---|---|---|
| PRO2198 | 44-34-C10-sc08 | 50-09-D07-sc04 | 198 | 0.70 | 1.02 |
| PRO2199 | 44-34-C10-sc09 | 50-09-D07-sc04 | 142 | 0.61 | 0.90 |
| PRO2206* | 44-34-C10-sc08 | 50-09-D07-sc04 | 230 | 0.65 | not measured |
| PRO2207* | 44-34-C10-sc09 | 50-09-D07-sc04 | 215 | 0.55 | not measured |

N = number of repeated analyses.
*$IC_{50}$ or relative $IC_{50}$ (single analysis)/NA: not applicable

TABLE 46

Ability of the Morrison antibodies to neutralize IL-4-induced CD23 expression on human PBMCs

| | | | | | monocytes | | naive B cells | | memory B cells | |
|---|---|---|---|---|---|---|---|---|---|---|
| PRO ID | Fab-arm domain | Constant | scFv-domain | blood donor | $IC_{50}$ [pM] | [$IC_{50\ dupilumab}$/ $IC_{50\ sample}$] | $IC_{50}$ [pM] | [$IC_{50\ dupilumab}$/ $IC_{50\ sample}$] | $IC_{50}$ [pM] | [$IC_{50\ Dupilumab}$/ $IC_{50\ sample}$] |
| PRO2198 | 44-34-C10-sc08 | IgG4 (S228P) | 50-09-D07-sc04 | 1 | 90.37 | 0.11 | 1366 | 0.31 | 4470 | 0.14 |
| PRO2199 | 44-34-C10-sc09 | IgG4 (S228P) | 50-09-D07-sc04 | 1 | 69.74 | 0.15 | 1099 | 0.38 | 2531 | 0.25 |

TABLE 46-continued

Ability of the Morrison antibodies to neutralize IL-4-induced CD23 expression on human PBMCs

| PRO ID | Fab-arm domain | Constant | scFv-domain | blood donor | monocytes $IC_{50}$ [pM] | monocytes $[IC_{50\ dupilumab}/IC_{50\ sample}]$ | naive B cells $IC_{50}$ [pM] | naive B cells $[IC_{50\ dupilumab}/IC_{50\ sample}]$ | memory B cells $IC_{50}$ [pM] | memory B cells $[IC_{50\ Dupilumab}/IC_{50\ sample}]$ |
|---|---|---|---|---|---|---|---|---|---|---|
| PRO2206 | 44-34-C10-sc08 | IgG4 (S228P) | 50-09-D07-sc04 | 2 | 110.5 | 0.12 | 1480 | 0.45 | 4339 | 0.13 |
| PRO2207 | 44-34-C10-sc09 | IgG4 (S228P) | 50-09-D07-sc04 | 3 | *54.47 | 0.02 | 1036 | 0.12 | 1580 | 0.20 |

*approximate values, top constraint applied when fitting curves

TABLE 47

Masses for light and heavy chain of each Morrison antibody found under reducing condition

| Masses in [Da] | PRO2198 | PRO2199 | PRO2206 | PRO2207 |
|---|---|---|---|---|
| Calculated mass Light chain (LC) | 23582 | 23458 | 51028 | 50904 |
| Detected mass | 23580 | 23453 | 51019 | 50895 |
| Calculated mass Heavy chain (HC) | 77368.8 | 77169 | 49923 | 49743 |
| Detected mass Main species | 78798 (+1429) | 78618 (+1429) | 51358 (+1435) | 51179 (+1436) |
| Comments | HC: Not fully reduced and glycosylated | LC: Not fully reduced HC: Not fully reduced and glycosylated | LC: Not fully reduced HC: Not fully reduced and glycosylated | LC: Not fully reduced HC: Not fully reduced and glycosylated |

Glycosylation Pattern

PRO2198 and PRO2199 were analyzed in more details for their glycosylation pattern. Both molecules show a similar glycosylation. An approximation of the relative glycosylation of the respective heavy chain is shown in Table 48. Both molecules are glycosylated mainly with G0F sugar. Lower amounts of G1F and G2F are also found. No non-glycosylated mass for the heavy chain was observed.

TABLE 48

Type and relative abundance of heavy chain glycosylation

| Glycosylation | PRO2198 | PRO2199 |
|---|---|---|
| G0F (+1445 Da) | 65% | 65% |
| G1F (+1608 Da) | 30% | 30% |
| G2F (+1770 Da) | 5% | 5% |

SDS Page

Figure 12:
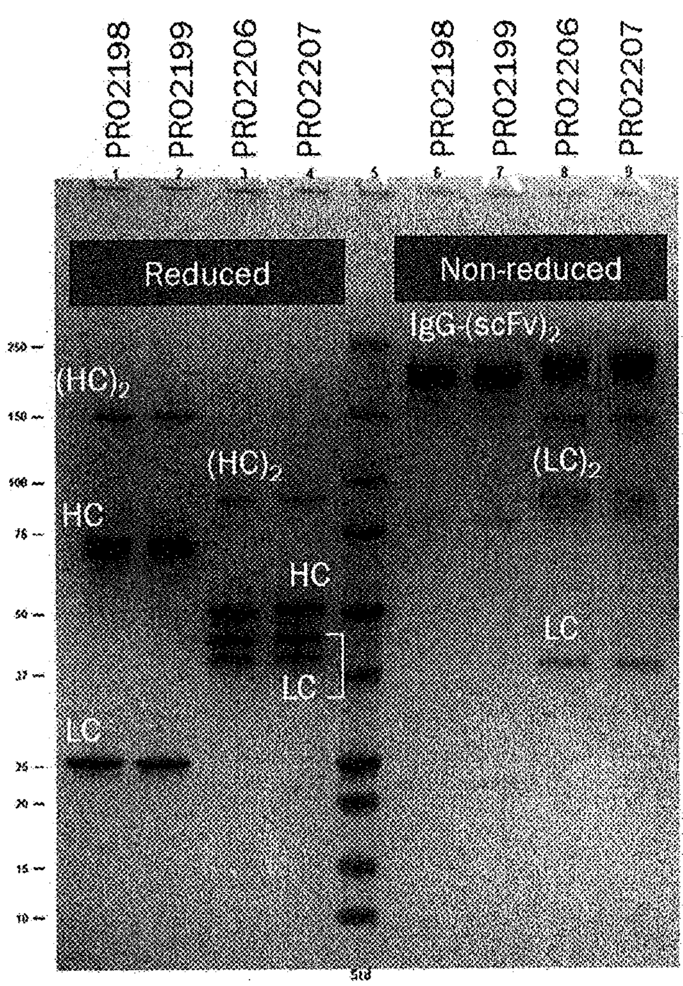
FIG. 12 shows an SDS-Page analysis of PRO2198, PRO2199, PRO2206 and PRO2207 under reducing and non-reducing conditions.

The identity of the Morrison-H and Morrison-L antibodies PRO2198, PRO2199, PRO2206 and PRO2207 was additionally analyzed by SDS-PAGE under reducing and non-reducing condition (see FIG. 12).

For the Morrison-H molecules, the expected bands were observed both under reducing as well as non-reducing conditions. Some HC dimer is observed under reducing conditions, presumably due to incomplete reduction of the interchain disulfide.

In case of the Morrison-L molecules, all expected bands are visible under both reducing and non-reducing conditions and represent the most prominent species. An additional band between 37 kDa and 50 kDa is observed under reducing conditions suggesting the LC or HC not being fully denatured or reduced under the chosen condition. The band running between 75 kDa and 100 kDa presumably originates from a LC dimer. Under non-reducing conditions, LC and LC dimers are visible. For IgG molecules it is known that the LC and LC dimers are soluble and can be present using a generic purification process.

7.2. Multi-pH Stress Study:

Aim of the multi-pH stress study was to examine the chemical and thermal stability of the Morrison-H and Morrison-L antibodies PRO2198, PRO2199, PRO2206 and PRO2207. The molecules were dialyzed into a 20 mM MES/Acetate/Hepes buffer with pH 3.5, 5, 7, and 8.5. In the latter three conditions, samples were incubated for 10 days at 40° C. to force chemical degradation such as oxidation and clipping. pH 3.5 is a harsh stress condition leading to rapid degradation and hydrolysis, therefore these samples were incubated at 25° C. for 10 days. The formation of charge variants was analyzed by CEX-HPLC and clipping was investigated by SDS-PAGE. The molecules were incubated at a concentration of 1 mg/ml. Thermal stability was analyzed by nDSF (NanoTemper) determining the onset of unfolding ($T_{onset}$), midpoint of unfolding ($T_{m1}$) and onset of aggregation ($T_{Scattering}$).

Charge Variants Profile

During later DSP development, purification in high yields is an important measure. One of the main techniques used to purify IgG like molecules is ion exchange chromatography. Therefore, IgG antibodies showing a high target purity by CEX-HPLC are likely to be less challenging during the development of an ion exchange purification step.

All tested antibodies, i.e. PRO2198, PRO2199, PRO2206 and PRO2207, exhibited a comparable complexity (charge heterogeneity), whereby the Morrison-L molecules showed a slightly smaller complexity than the Morrison-H molecules. In addition, the molecules PRO2199 and PRO2207 that are based on the IL-4R clone sc09 had a slightly higher target purity.

In summary, all molecules showed a low charge heterogeneity after a generic purification process without substantial differences.

Formation of Charge Variants

The formation of charge variants was analyzed for PRO2198, PRO2199, PRO2206 and PRO2207 after incubation in 20 mM MES/Acetate/Hepes buffer at pH 3.5, pH 5, pH 7 and pH 8.5. A specific importance is given to the chemical stability at pH 5 and pH 7 as these pH values define approximate limits for the later formulation space. Table 49 shows the results obtained. At pH 5, all molecules showed a good stability towards chemical degradation. For higher pH values, chemical degradation towards the formation of acidic variants increased. All molecules showed similar stabilities except PRO2206, which had a higher target loss at pH 8.5. At pH 3.5, only minor amounts of chemical degradation were observed.

TABLE 49

| Formation of charge variants at different pH | | | | |
|---|---|---|---|---|
| Values in [rel. %] | PRO2198 | PRO2199 | PRO2206 | PRO2207 |
| t0 | 76.4 | 81.4 | 78.1 | 84.1 |
| ΔTarget after 10 days of storage at 40° C.[#1] | | | | |
| pH 3.5 | 3.1 | 1.9 | 1.0 | 1.3 |
| pH 5.0 | 1.1 | 0.2 | −1.0 | −0.7 |
| pH 7.0 | −5.5 | −7.2 | −6.8 | −7.2 |
| pH 8.5 | −12.9 | −11.8 | −22.0 | −15.5 |

([#1]Storage temperature at pH 3.5 is 25° C.)

Analysis of Clipping by SDS-PAGE

Figure 13:
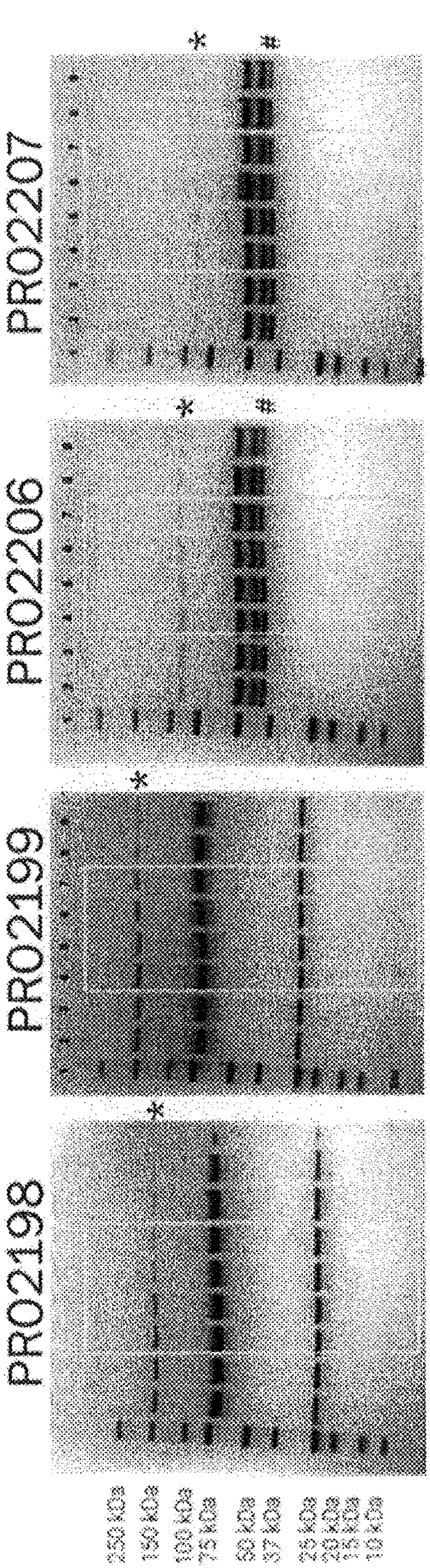
FIG. 13 shows an analysis of clipping by SDS-PAGE. $1^{st}$ lane: Marker—$2^{nd}$: pH 3.5, t0—$3^{rd}$: pH 3.5, t10d—$4^{th}$: pH 5, t0—$5^{th}$: pH 5, t10d—$6^{th}$: pH 7, t0d—$7^{th}$: pH 7, t10d—$8^{th}$: pH 8.5, t0—$9^{th}$: pH 8.5, t10d. *Presumably, incomplete reduction of HC dimer. #Presumably, incomplete reduction of LC.

All proteins were analyzed for clipping using SDS-PAGE analysis (see FIG. 13). No fragmentation was observed for any of the Morrison antibodies at pH 3.5, pH 5 and pH 7. Only little fragmentation of the HC of PRO2198 and PRO2199 was observed at pH 8.5. Although no HC clipping was observed for the Morrison-L molecules, it could be overlaid by the closely running LC.

In summary, all molecules showed a good resistance towards clipping.

Thermal Stability

Within the pH stress study, PRO2198, PRO2199, PRO2206 and PRO2207 were analyzed for their thermal stability between pH 3.5 and pH 8.5. Both thermal unfolding as well as the onset of thermal aggregation were determined. During thermal unfolding, all molecules showed more than one transition due to the multi domain architecture of the molecules. For simplicity, only the first melting midpoint is shown. Table 50 summarizes the results.

TABLE 50

| Thermal stability | | | | |
|---|---|---|---|---|
| pH | PRO2198 | PRO2199 | PRO2206 | PRO2207 |
| Onset of unfolding ($T_{onset}$) by nDSF [° C.] | | | | |
| 3.5 | 45.6 | 43.4 | 42.4 | 40.9 |
| 5 | 55.4 | 55.1 | 55.8 | 56.3 |
| 7 | 60.5 | 59.3 | 58.7 | 57.5 |
| 8.5 | 59.7 | 58.3 | 57.0 | 55.1 |
| Midpoint of the first unfolding transition ($T_{m1}$) by nDSF [° C.] | | | | |
| 3.5 | 50.7 | 50.6 | 49.7 | 50.0 |
| 5 | 62.9 | 62.8 | 62.1 | 62.0 |
| 7 | 66.9 | 66.7 | 66.2 | 66.1 |
| 8.5 | 66.5 | 66.2 | 65.1 | 65.1 |
| Onset of aggregation ($T_{scattering}$) by nDSF [° C.] | | | | |
| 3.5 | No aggregation observed | | | |
| 5 | No aggregation observed | | | |
| 7 | 73.5 | 71.6 | 72.2 | 69.0 |
| 8.5 | 71.4 | 68.4 | 68.8 | 65.2 |

The onset of unfolding ($T_{onset}$) as well as the first melting point ($T_{m1}$) was highest at pH 7 for all molecules. A change to pH 8.5 decreased the thermal stability only slightly. Towards acidic pH, the thermal stability decreased. However, at pH 5 all onsets of unfolding were above 55° C. At pH 3.5, the thermal stability decreased to a $T_{onset}$ below 50° C.

Thermal aggregation was only observed at pH 7 and pH 8.5. At acidic pH, both pH 3.5 and pH 5.0, all Morrison antibodies did not form larger aggregates, even in the unfolded state. At neutral and basic pH, the aggregation onset was above the first melting point, suggesting a non-native aggregation mechanism.

Although the differences between the molecules were not substantially, PRO2198 has overall the highest stability. This was most prominent at pH 3.5 with a 5° C. higher $T_{onset}$ compared to PRO2207. This pH is relevant in the production process for a viral inactivation step.

7.3. High Concentration Study

For the concentration feasibility tests PRO2198 was formulated in two formulation buffers:

Formulation buffer F1: 20 mM acetate at pH 5.5;

Formulation buffer F2: 20 mM citrate with 50 mM NaCl at pH 5.5.

Solubility—Protein Concentration

PRO2198 could be concentrated above 100 mg/ml, without signs of precipitation or reaching the limit of solubility. Furthermore, PRO2198 showed no detectable decrease in protein concentration, i.e. PRO2198 was sufficiently soluble to reach and keep a target concentration of above 100 mg/ml for at least four weeks at 4° C. and 25° C.

Monomer Stability at Different Temperatures

PRO2198 was formulated in F1 and F2 and concentrated to >100 mg/ml. The concentrated samples were stored at 4° C., 25° C. and 40° C. for up to 4 weeks. At different time points, the monomeric content was analyzed by means of SE-HPLC. The results are summarized in Table 51.

TABLE 51

| Monomer stability for PRO2198 at a concentration of >100 mg/ml | | | | | |
|---|---|---|---|---|---|
| Storage temperature | time | Formulation F1 Monomer [rel. %] | | Formulation F2 Monomer [rel. %] | |
| [° C.] | [weeks] | Absolut | Delta | Absolut | Delta |
| N/A | 0 | 99.0 | 0.0 | 99.1 | 0.0 |
| 4.0 | 4 | 98.1 | −0.9 | 98.3 | −0.8 |
| 25.0 | 4 | 96.1 | −2.9 | 96.2 | −2.9 |
| 40.0 | 2 | 83.1 | −15.9 | 82.0 | −17.1 |
| | 4 | 72.4 | −26.6 | 70.9 | −28.2 |

7.4. General Methods Used in the Biophysical Characterization of the Morrison-H and Morrison-L Antibodies Buffer Exchange Buffer exchange was carried out by dialysis. The antibodies were dialyzed in Spectra Pro 3 dialysis membranes (Spectrum Laboratories) with at least a 200-fold excess of dialysis buffer.

Concentrating of the Antibodies

Antibodies were concentrated using centrifugal concentrators with a molecular weight cut-off (MWCO) of 10 kDa or 30 kDa. Samples were centrifuged in 5 min steps at 22° C. until target concentration was reached. In between steps, the samples are resuspended.

Determination of Protein Concentration

The concentration of the protein samples was determined using a Tecan plate reader and a NanoQuant Plate. The buffer was used as blank to be subtracted from the absorbance measured at 280 nm. Each measurement was corrected for scattering caused by visible particles determined at 310 nm. The corrected value was normalized to a path length of 1 cm and the protein concentration calculated using the theoretical extinction coefficient of the corresponding protein. For protein samples with a concentration higher than 10 mg/ml, the sample was diluted in the corresponding buffer at least 10 times or to 1 mg/ml nominal concentration.

SDS-PAGE

SDS-PAGE was done under reducing conditions. After denaturation and reduction 5 μg of the sample were applied on a gradient gel (4%-20%). After separation, protein bands were stained with Coomassie Blue and the gel destained with purified water.

Storage

To assess the protein stability at different temperatures, samples were incubated at 4° C., 25° C. and 40° C. Storage at 4° C. was carried out in a fridge at a nominal temperature of 4° C. For storage at 25° C. and 40° C. samples were placed in cabinets with controlled humidity of 65% rH and 75% rH, respectively.

Thermal Unfolding by nanoDSF

Thermal unfolding using a thermal shift assay was determined by the change in fluorescence intensity of Sypro Orange. The fluorescence of the dye is sensitive to hydrophobic interactions. As the protein unfolds, hydrophobic amino acids are exposed to the solvent leading to an increased fluorescence of Sypro Orange. The resulting midpoint of thermal unfolding (Tm) as well as the onset temperature calculated at 10% of the maximal signal ($T_{onset}$ is the temperature at: min. signal+0.1*(max. signal−min. signal)) was determined by fitting the data to a Boltzmann equation.

Monomeric Content by SE-HPLC

The monomeric content was determined by analytical size-exclusion chromatography using a Shodex KW403-4F column running in 50 mM sodium phosphate, 300 mM NaCl, pH 6.5. For analysis, 5 μg of sample were injected and the absorption recorded at 280 nm. The quality of the sample is stated as relative percentages of monomer, HMWS, and LMWS.

Cation Exchange HPLC (CEX-HPLC)

For the quantification of charge variants, analytical cation exchange chromatography was applied. The samples were analyzed on a MAbPac™ SCX-10 column. The charge variants were separated using a pH gradient from pH 4 to pH 10. For analysis, 30 μg of sample were injected and the absorption recorded at 280 nm. The quality of the sample is stated as relative percentages of target, acidic charge variants, and basic charge variants.

Mass Spectrometry

For identification and the exclusion of severe post-translational modifications, the intact mass of the Morrison antibodies was determined. Samples were reduced with DTT prior to ESI-MS analyses, desalted and analyzed in MeOH:2-PrOH:0.2% FA (30:20:50). Nano ESI-MS analyses of the samples were performed on a Syn-apt G2-Si mass spectrometer. The recorded m/z data were then deconvoluted into mass spectra by applying the maximum entropy algorithm MaxEnt1 (MaxLynx) with a resolution of the output mass 0.5 Da/channel and Uniform Gaussian Damage Model at the half height of 0.7 Da.

The invention claimed is:

1. A multispecific antibody comprising:

a) one or two binding domains, which specifically bind to IL-4R (IL4R-BD), and b) one or two binding domains, which specifically bind to IL-31 (IL31-BD), wherein the multispecific antibody comprises an immunoglobulin Fc region;

each of said IL4R-BDs comprise an HCDR1 sequence of SEQ ID NO: 1,

HCDR2 sequence of SEQ ID NO: 2, an HCDR3 sequence of SEQ ID NO: 3, an LCDR1 sequence of SEQ ID NO: 7, an LCDR2 sequence of SEQ ID NO: 8, and an LCDR3 sequence of SEQ ID NO: 9; and each of said IL31-BDs comprises an HCDR1 sequence of SEQ ID NO: 12, an HCDR2 sequence of SEQ ID NO: 13, an HCDR3 sequence of SEQ ID NO: 14, an LCDR1 sequence of SEQ ID NO: 17, an LCDR2 sequence of SEQ ID NO: 19, and an LCDR3 sequence of SEQ ID NO: 20.

2. The multispecific antibody of claim 1, wherein the format of said multispecific antibody is selected from bivalent bispecific IgG formats, trivalent bispecific IgG formats and tetravalent bispecific IgG formats.

3. The multispecific antibody of claim 1, wherein the format of said multispecific antibody is a Morrison format.

4. The multispecific antibody of claim 1, wherein said multispecific antibody comprises two IL4R-BDs and two IL31-BDs.

5. The multispecific antibody of claim 3, wherein the IL4R-BDs are located in a Fab of the Morrison format, and the IL31-BDs are located in an scFv of the Morrison format.

6. The multispecific antibody of claim 3, wherein the format of the multispecific antibody is selected from a Morrison-L and a Morrison-H format.

7. The multispecific antibody of claim 1, wherein said IL4R-BDs comprise a) a heavy chain variable domain comprising an amino acid sequence that is at least 90, 91, 92, 93, 94, 95, 96, 97, 98 or 99 percent identical to SEQ ID NO: 4 and a light chain variable domain comprising an amino acid sequence that is at least 90, 91, 92, 93, 94, 95, 96, 97, 98 or 99 percent identical to SEQ ID NO: 11; or b) a heavy chain variable domain comprising an amino acid sequence of SEQ ID NO: 4 and a light chain variable domain comprising an amino acid sequence of SEQ ID NO: 11.

8. The multispecific antibody of claim 1, wherein said IL31-BDs comprise a) a heavy chain variable domain comprising an amino acid sequence that is at least 90, 91, 92, 93, 94, 95, 96, 97, 98 or 99 percent identical to SEQ ID NO: 16 and a light chain variable domain comprising an amino acid sequence that is at least 90, 91, 92, 93, 94, 95, 96, 97, 98 or 99 percent identical to SEQ ID NO: 21; or b) a heavy chain variable domain comprising an amino acid sequence of SEQ ID NO: 16 and a light chain variable domain comprising an amino acid sequence of SEQ ID NO: 21.

9. The multispecific antibody of claim 1, wherein the immunoglobulin Fc region is selected from IgG subclasses IgG1 and IgG4.

10. The multispecific antibody of claim 9, wherein the immunoglobulin Fc region is selected from IgG subclass IgG4.

11. The multispecific antibody of claim 2, wherein the format of said multispecific antibody is selected from KiH-based IgGs; DVD-1g; CODV-IgG and Morrison (IgG CH3-scFv fusion (Morrison-H) or IgG CL-scFv fusion (Morrison-L)).

12. The multispecific antibody of claim 6, wherein the format of the multispecific antibody is the Morrison-H format.

13. The multispecific antibody of claim 1, comprising a Morrison antibody having a heavy chain comprising an amino acid sequence of SEQ ID NO: 38 and a light chain comprising an amino acid sequence of SEQ ID NO: 37.

14. A multispecific antibody comprising two IL-4R binding domains (IL4R-BD) and two IL-31 binding domains (IL31-BD), wherein (a) each of said IL4R-BDs comprise an HCDR1 sequence of SEQ ID NO: 1, an HCDR2 sequences of SEQ ID NO: 2, an HCDR3 sequence of SEQ ID NO: 3, an LCDR1 sequence of SEQ ID NO: 7, an LCDR2 sequence of SEQ ID NO: 8, and an LCDR3 sequence of SEQ ID NO: 9; and (b) each of said IL31-BDs comprises an HCDR1 sequence of SEQ ID NO: 12, an HCDR2 sequence of SEQ ID NO: 13, an HCDR3 sequence of SEQ ID NO: 14, an LCDR1 sequence of SEQ ID NO: 17, an LCDR2 sequence of SEQ ID NO: 19, and an LCDR3 sequence of SEQ ID NO: 20.

15. A multispecific antibody comprising (a) a first heavy chain variable domain comprising an amino acid sequence of SEQ ID NO: 4;

(b) a first light chain variable domain comprising an amino acid sequence of SEQ ID NO: 11;

(c) a second heavy chain variable domain comprising an amino acid sequence of SEQ ID NO: 16; and (d) a second light chain variable domain comprising an amino acid sequence of SEQ ID NO: 21.

16. A multispecific antibody comprising (a) two heavy chains, each heavy chain comprising an amino acid sequence of SEQ ID NO: 38; and (b) two light chains, each light chain comprising an amino acid sequence of SEQ ID NO: 37.

17. A nucleic acid or two nucleic acids encoding the multispecific antibody of claim 1.

18. A vector or two vectors comprising the nucleic acid or the two nucleic acids of claim 17.

19. A host cell or host cells comprising the vector or the two vectors of claim 18.

20. A nucleic acid or two nucleic acids encoding the multispecific antibody of claim 14.

21. A vector or two vectors comprising the nucleic acid or the two nucleic acids of claim 20.

22. A host cell or host cells comprising the vector or the two vectors of claim 21.

23. A pharmaceutical composition comprising the multispecific antibody of claim 14 and a pharmaceutically acceptable carrier.

24. A nucleic acid or two nucleic acids encoding the multispecific antibody of claim 15.

25. A vector or two vectors comprising the nucleic acid or the two nucleic acids of claim 24.

26. A host cell or host cells comprising the vector or the two vectors of claim 25.

27. A pharmaceutical composition comprising the multispecific antibody of claim 15 and a pharmaceutically acceptable carrier.

28. A nucleic acid or two nucleic acids encoding the multispecific antibody of claim 16.

29. A vector or two vectors comprising the nucleic acid or the two nucleic acids of claim 28.

30. A host cell or host cells comprising the vector or the two vectors of claim 29.

31. A method for producing the multispecific antibody of claim 1, comprising providing the nucleic acid or the two nucleic acids encoding the multispecific antibody of claim 1, expressing said nucleic acid or said two nucleic acids, and collecting said multispecific antibody from an expression system.

32. A pharmaceutical composition comprising the multispecific antibody of claim 1 and a pharmaceutically acceptable carrier.

33. A pharmaceutical composition comprising the multispecific antibody of claim 13 and a pharmaceutically acceptable carrier.

34. A pharmaceutical composition comprising the multispecific antibody of claim 16 and a pharmaceutically acceptable carrier.

35. A method of treating a condition comprising the administration of the multispecific antibody of claim 16 to a subject in need thereof, wherein the condition is selected from the group consisting of pruritus-causing allergic diseases, pruritus-causing inflammatory diseases, pruritus-causing autoimmune diseases, atopic dermatitis, acute allergic contact dermatitis, chronic spontaneous urticaria, bullous pemphigoid, alopecia areata, dermatomyositis, prurigo nodularis, psoriasis or atopic asthma.

36. A method of treating a condition comprising the administration of the antibody of claim 16 to a subject in need thereof, wherein the condition is selected from the group consisting of pruritus, atopic dermatitis, acute allergic contact dermatitis, chronic spontaneous urticaria, bullous pemphigoid, alopecia areata, dermatomyositis, prurigo nodularis, psoriasis and atopic asthmas.

* * * * *

SEQUENCE LISTING

```
<160> NUMBER OF SEQ ID NOS: 50

<210> SEQ ID NO 1
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 1

Gly Phe Ser Ser Ser Ser Ala His Tyr Met Cys
1               5                   10


<210> SEQ ID NO 2
<211> LENGTH: 18
<212> TYPE: PRT
<213> ORGANISM: Artificial sequence
<220> FEATURE:
<223> OTHER INFORMATION: artificial antibody-related sequence

<400> SEQUENCE: 2

Cys Ile Tyr Ala Gly Ser Arg Gly Ser Thr Tyr Tyr Ala Ser Trp Ala
1               5                   10                  15

Lys Gly
```

<210> SEQ ID NO 3
<211> LENGTH: 19
<212> TYPE: PRT
<213> ORGANISM: Artificial sequence
<220> FEATURE:
<223> OTHER INFORMATION: artificial antibody-related sequence

<400> SEQUENCE: 3

```
Arg Ala Ala Phe Val Asn Arg Gly Val Ser Trp Ile Trp Pro Tyr Tyr
1               5                   10                  15

Phe Ser Leu
```

<210> SEQ ID NO 4
<211> LENGTH: 129
<212> TYPE: PRT
<213> ORGANISM: Artificial sequence
<220> FEATURE:
<223> OTHER INFORMATION: artificial antibody-related sequence

<400> SEQUENCE: 4

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ser Ser Ser Ala
            20                  25                  30

His Tyr Met Cys Trp Val Arg Gln Ala Pro Gly Lys Gly Leu Glu Trp
        35                  40                  45

Ile Gly Cys Ile Tyr Ala Gly Ser Arg Gly Ser Thr Tyr Tyr Ala Ser
    50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ala Ala Phe Val Asn Arg Gly Val Ser Trp Ile Trp
            100                 105                 110

Pro Tyr Tyr Phe Ser Leu Trp Gly Gln Gly Thr Leu Val Thr Val Ser
        115                 120                 125

Ser
```

<210> SEQ ID NO 5
<211> LENGTH: 128
<212> TYPE: PRT
<213> ORGANISM: Artificial sequence
<220> FEATURE:
<223> OTHER INFORMATION: artificial antibody-related sequence

<400> SEQUENCE: 5

```
Glu Val Gln Leu Val Glu Ser Gly Gly Gly Arg Val Gln Pro Gly Gly
1               5                   10                  15

Ser Leu Arg Leu Ser Cys Ala Ala Ser Gly Phe Ser Ser Ser Ser Ala
            20                  25                  30

His Tyr Met Cys Trp Val Arg Gln Ala Pro Gly Lys Gly Leu Glu Trp
        35                  40                  45

Ile Gly Cys Ile Tyr Ala Gly Ser Arg Gly Ser Thr Tyr Tyr Ala Ser
    50                  55                  60

Trp Ala Lys Gly Arg Phe Thr Ile Ser Lys Ala Ser Ser Thr Thr Val
65                  70                  75                  80

Tyr Leu Gln Met Asn Ser Leu Arg Ala Glu Asp Thr Ala Thr Tyr Tyr
                85                  90                  95
```

```
Cys Ala Arg Ala Ala Phe Val Asn Arg Gly Val Ser Trp Ile Trp Pro
            100                 105                 110

Tyr Tyr Phe Ser Leu Trp Gly Gln Gly Thr Gln Val Thr Val Ser Ser
        115                 120                 125


<210> SEQ ID NO 6
<211> LENGTH: 128
<212> TYPE: PRT
<213> ORGANISM: Artificial sequence
<220> FEATURE:
<223> OTHER INFORMATION: artificial antibody-related sequence

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ser Ser Ser Ala
            20                  25                  30

His Tyr Met Cys Trp Val Arg Gln Ala Pro Gly Lys Gly Leu Glu Trp
        35                  40                  45

Ile Gly Cys Ile Tyr Ala Gly Ser Arg Gly Ser Thr Tyr Tyr Ala Ser
    50                  55                  60

Trp Ala Lys Gly Arg Phe Thr Ile Ser Lys Ala Ser Ser Thr Thr Val
65                  70                  75                  80

Tyr Leu Gln Met Asn Ser Leu Arg Ala Glu Asp Thr Ala Val Tyr Tyr
                85                  90                  95

Cys Ala Arg Ala Ala Phe Val Asn Arg Gly Val Ser Trp Ile Trp Pro
            100                 105                 110

Tyr Tyr Phe Ser Leu Trp Gly Gln Gly Thr Leu Val Thr Val Ser Ser
        115                 120                 125


<210> SEQ ID NO 7
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 7

Gln Ala Ser Glu Asp Ile Glu Ser Tyr Leu Ala
1               5                   10


<210> SEQ ID NO 8
<211> LENGTH: 7
<212> TYPE: PRT
<213> ORGANISM: Artificial sequence
<220> FEATURE:
<223> OTHER INFORMATION: artificial antibody-related sequence

<400> SEQUENCE: 8

Arg Ala Ser Thr Leu Ala Tyr
1               5


<210> SEQ ID NO 9
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 9

Leu Gly Ser Ser Tyr Ser Thr Gly Ser Asn Ile
1               5                   10
```

```
<210> SEQ ID NO 10
<211> LENGTH: 99
<212> TYPE: PRT
<213> ORGANISM: Artificial sequence
<220> FEATURE:
<223> OTHER INFORMATION: artificial antibody-related sequence

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gly Ser Ser Tyr Ser Thr Gly
                85                  90                  95

Ser Asn Ile


<210> SEQ ID NO 11
<211> LENGTH: 99
<212> TYPE: PRT
<213> ORGANISM: Artificial sequence
<220> FEATURE:
<223> OTHER INFORMATION: artificial antibody-related sequence

<400> SEQUENCE: 11

Asp Ile Gln Met Thr Gln Ser Pro Ser Ser Leu Ser Ala Arg Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Tyr Gly Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Phe Ala Thr Tyr Tyr Cys Leu Gly Ser Ser Tyr Ser Thr Gly
                85                  90                  95

Ser Asn Ile


<210> SEQ ID NO 12
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 12

Gly Phe Ser Phe Ser Ala Asn Tyr Trp Ile Cys
1               5                   10


<210> SEQ ID NO 13
<211> LENGTH: 18
<212> TYPE: PRT
<213> ORGANISM: Artificial sequence
```

```
<220> FEATURE:
<223> OTHER INFORMATION: artificial antibody-related sequence

<400> SEQUENCE: 13

Cys Ile Tyr Ile Gly Ser Arg Ala Asp Thr Tyr Tyr Ala Pro Trp Ala
1               5                   10                  15

Lys Gly


<210> SEQ ID NO 14
<211> LENGTH: 14
<212> TYPE: PRT
<213> ORGANISM: Artificial sequence
<220> FEATURE:
<223> OTHER INFORMATION: artificial antibody-related sequence

<400> SEQUENCE: 14

Arg Phe Ser Ser Gly Ile Tyr Asp Leu Asp Arg Phe Phe Leu
1               5                   10


<210> SEQ ID NO 15
<211> LENGTH: 124
<212> TYPE: PRT
<213> ORGANISM: Artificial sequence
<220> FEATURE:
<223> OTHER INFORMATION: artificial antibody-related sequence

<400> SEQUENCE: 15

Gln Ser Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ala Asn
            20                  25                  30

Tyr Trp Ile Cys Trp Val Arg Gln Ala Pro Gly Lys Gly Leu Glu Trp
        35                  40                  45

Ile Val Cys Ile Tyr Ile Gly Ser Arg Ala Asp Thr Tyr Tyr Ala Pro
    50                  55                  60

Trp Ala Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Val Tyr
                85                  90                  95

Phe Cys Ala Arg Phe Ser Ser Gly Ile Tyr Asp Leu Asp Arg Phe Phe
            100                 105                 110

Leu Trp Gly Gln Gly Thr Leu Val Thr Val Ser Ser
        115                 120


<210> SEQ ID NO 16
<211> LENGTH: 124
<212> TYPE: PRT
<213> ORGANISM: Artificial sequence
<220> FEATURE:
<223> OTHER INFORMATION: artificial antibody-related sequence

<400> SEQUENCE: 16

Gln Ser Gln Leu Val Glu Ser Gly Gly Gly Arg Val Gln Pro Gly Gly
1               5                   10                  15

Ser Leu Arg Leu Ser Cys Ala Ala Ser Gly Phe Ser Phe Ser Ala Asn
            20                  25                  30

Tyr Trp Ile Cys Trp Val Arg Gln Ala Pro Gly Lys Gly Leu Glu Trp
        35                  40                  45

Ile Val Cys Ile Tyr Ile Gly Ser Arg Ala Asp Thr Tyr Tyr Ala Pro
    50                  55                  60
```

```
Trp Ala Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Thr Tyr
                85                  90                  95

Phe Cys Ala Arg Phe Ser Ser Gly Ile Tyr Asp Leu Asp Arg Phe Phe
            100                 105                 110

Leu Trp Gly Gln Gly Thr Gln Val Thr Val Ser Ser
        115                 120


<210> SEQ ID NO 17
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 17

Gln Ala Ser Gln Ser Ile Asp Ser Trp Leu Ala
1               5                   10


<210> SEQ ID NO 18
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 18

Gln Ala Ser Gln Ser Ile Glu Ser Trp Leu Ala
1               5                   10


<210> SEQ ID NO 19
<211> LENGTH: 7
<212> TYPE: PRT
<213> ORGANISM: Artificial sequence
<220> FEATURE:
<223> OTHER INFORMATION: artificial antibody-related sequence

<400> SEQUENCE: 19

Gln Ala Ser Lys Leu Ala Ser
1               5


<210> SEQ ID NO 20
<211> LENGTH: 12
<212> TYPE: PRT
<213> ORGANISM: Artificial sequence
<220> FEATURE:
<223> OTHER INFORMATION: artificial antibody-related sequence

<400> SEQUENCE: 20

Gln Thr Tyr Tyr Gly Gly Gly His Ile Gly Trp Gly
1               5                   10


<210> SEQ ID NO 21
<211> LENGTH: 100
<212> TYPE: PRT
<213> ORGANISM: Artificial sequence
<220> FEATURE:
<223> OTHER INFORMATION: artificial antibody-related sequence

<400> SEQUENCE: 21

Ala Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asp Ser Trp
            20                  25                  30
```

```
Leu Ala Trp Tyr Gln Gln Lys Pro Gly Lys Pro Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Thr Tyr Tyr Gly Gly Gly His
                85                  90                  95

Ile Gly Trp Gly
            100


<210> SEQ ID NO 22
<211> LENGTH: 100
<212> TYPE: PRT
<213> ORGANISM: Artificial sequence
<220> FEATURE:
<223> OTHER INFORMATION: artificial antibody-related sequence

<400> SEQUENCE: 22

Ala Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Glu Ser Trp
            20                  25                  30

Leu Ala Trp Tyr Gln Gln Lys Pro Gly Lys Pro Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Thr Tyr Tyr Gly Gly Gly His
                85                  90                  95

Ile Gly Trp Gly
            100


<210> SEQ ID NO 23
<211> LENGTH: 122
<212> TYPE: PRT
<213> ORGANISM: Artificial sequence
<220> FEATURE:
<223> OTHER INFORMATION: artificial antibody-related sequence

<400> SEQUENCE: 23

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ala Asn
            20                  25                  30

Tyr Tyr Pro Cys Trp Val Arg Gln Ala Pro Gly Lys Gly Leu Glu Trp
        35                  40                  45

Ile Gly Cys Ile Tyr Gly Gly Ser Ser Asp Ile Thr Tyr Asp Ala Asn
    50                  55                  60

Trp Thr Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ser Ala Trp Tyr Ser Gly Trp Gly Gly Asp Leu Trp
            100                 105                 110

Gly Gln Gly Thr Leu Val Thr Val Ser Ser
```

```
        115                 120


<210> SEQ ID NO 24
<211> LENGTH: 124
<212> TYPE: PRT
<213> ORGANISM: Artificial sequence
<220> FEATURE:
<223> OTHER INFORMATION: artificial antibody-related sequence

<400> SEQUENCE: 24

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Asn Ser
            20                  25                  30

Tyr Trp Ile Cys Trp Ile Arg Gln Pro Pro Gly Lys Gly Leu Glu Trp
        35                  40                  45

Ile Gly Cys Thr Phe Val Gly Ser Ser Asp Ser Thr Tyr Tyr Ala Asn
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg His Pro Ser Asp Ala Val Tyr Gly Tyr Ala Asn Asn
            100                 105                 110

Leu Trp Gly Gln Gly Thr Leu Val Thr Val Ser Ser
        115                 120


<210> SEQ ID NO 25
<211> LENGTH: 108
<212> TYPE: PRT
<213> ORGANISM: Artificial sequence
<220> FEATURE:
<223> OTHER INFORMATION: artificial antibody-related sequence

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly
            100                 105


<210> SEQ ID NO 26
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 26

Phe Gly Thr Gly Thr Lys Val Thr Val Leu Gly
1               5                   10
```

<210> SEQ ID NO 27
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 27

Phe Gly Gly Gly Thr Lys Leu Thr Val Leu Gly
1               5                   10

<210> SEQ ID NO 28
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 28

Phe Gly Gly Gly Thr Gln Leu Ile Ile Leu Gly
1               5                   10

<210> SEQ ID NO 29
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 29

Phe Gly Glu Gly Thr Glu Leu Thr Val Leu Gly
1               5                   10

<210> SEQ ID NO 30
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 30

Phe Gly Ser Gly Thr Lys Val Thr Val Leu Gly
1               5                   10

<210> SEQ ID NO 31
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 31

Phe Gly Gly Gly Thr Gln Leu Thr Val Leu Gly
1               5                   10

<210> SEQ ID NO 32
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 32

Phe Gly Gly Gly Thr Gln Leu Thr Ala Leu Gly
1               5                   10

<210> SEQ ID NO 33
<211> LENGTH: 11
<212> TYPE: PRT
<213> ORGANISM: Artificial sequence
<220> FEATURE:
<223> OTHER INFORMATION: artificial antibody-related sequence

<400> SEQUENCE: 33

Phe Gly Cys Gly Thr Lys Val Thr Val Leu Gly
1               5                   10

<210> SEQ ID NO 34
<211> LENGTH: 20
<212> TYPE: PRT
<213> ORGANISM: Artificial sequence
<220> FEATURE:
<223> OTHER INFORMATION: artificial antibody-related sequence

<400> SEQUENCE: 34

Gly Gly Gly Gly Ser Gly Gly Gly Gly Ser Gly Gly Gly Gly Ser Gly
1               5                   10                  15

Gly Gly Gly Ser
            20

<210> SEQ ID NO 35
<211> LENGTH: 5
<212> TYPE: PRT
<213> ORGANISM: Artificial sequence
<220> FEATURE:
<223> OTHER INFORMATION: artificial antibody-related sequence

<400> SEQUENCE: 35

Gly Gly Gly Gly Ser
1               5

<210> SEQ ID NO 36
<211> LENGTH: 10
<212> TYPE: PRT
<213> ORGANISM: Artificial sequence
<220> FEATURE:
<223> OTHER INFORMATION: artificial antibody-related sequence

<400> SEQUENCE: 36

Gly Gly Gly Gly Ser Gly Gly Gly Gly Ser
1               5                   10

<210> SEQ ID NO 37
<211> LENGTH: 216
<212> TYPE: PRT
<213> ORGANISM: Artificial sequence
<220> FEATURE:
<223> OTHER INFORMATION: artificial antibody-related sequence

<400> SEQUENCE: 37

Asp Ile Gln Met Thr Gln Ser Pro Ser Ser Leu Ser Ala Arg Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Tyr Gly Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

```
Glu Asp Phe Ala Thr Tyr Tyr Cys Leu Gly Ser Ser Tyr Ser Thr Gly
                85                  90                  95

Ser Asn Ile Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215
```

<210> SEQ ID NO 38
<211> LENGTH: 720
<212> TYPE: PRT
<213> ORGANISM: Artificial sequence
<220> FEATURE:
<223> OTHER INFORMATION: artificial antibody-related sequence

<400> SEQUENCE: 38

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ser Ser Ser Ala
            20                  25                  30

His Tyr Met Cys Trp Val Arg Gln Ala Pro Gly Lys Gly Leu Glu Trp
        35                  40                  45

Ile Gly Cys Ile Tyr Ala Gly Ser Arg Gly Ser Thr Tyr Tyr Ala Ser
    50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ala Ala Phe Val Asn Arg Gly Val Ser Trp Ile Trp
            100                 105                 110

Pro Tyr Tyr Phe Ser Leu Trp Gly Gln Gly Thr Leu Val Thr Val Ser
        115                 120                 125

Ser Ala Ser Thr Lys Gly Pro Ser Val Phe Pro Leu Ala Pro Cys Ser
    130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Lys
        195                 200                 205

Thr Tyr Thr Cys Asn Val Asp His Lys Pro Ser Asn Thr Lys Val Asp
    210                 215                 220
```

```
Lys Arg Val Glu Ser Lys Tyr Gly Pro Pro Cys Pro Pro Cys Pro Ala
225                 230                 235                 240

Pro Glu Phe Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Glu Asp Pro Glu Val Gln Phe Asn Trp Tyr Val
        275                 280                 285

Asp Gly Val Glu Val His Asn Ala Lys Thr Lys Pro Arg Glu Glu Gln
    290                 295                 300

Phe Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Gly
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Gln Glu Glu Met Thr
        355                 360                 365

Lys Asn Gln Val Ser Leu Thr Cys Leu Val Lys Gly Phe Tyr Pro Ser
    370                 375                 380

Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Arg Leu Thr Val Asp Lys Ser Arg Trp Gln Glu Gly Asn Val Phe
            420                 425                 430

Ser Cys Ser Val Met His Glu Ala Leu His Asn His Tyr Thr Gln Lys
        435                 440                 445

Ser Leu Ser Leu Ser Leu Gly Gly Gly Gly Gly Ser Gly Gly Gly Gly
    450                 455                 460

Ser Ala Phe Gln Leu Thr Gln Ser Pro Ser Ser Leu Ser Ala Ser Val
465                 470                 475                 480

Gly Asp Arg Val Thr Ile Thr Cys Gln Ala Ser Gln Ser Ile Asp Ser
                485                 490                 495

Trp Leu Ala Trp Tyr Gln Gln Lys Pro Gly Lys Pro Pro Lys Leu Leu
            500                 505                 510

Ile Tyr Gln Ala Ser Lys Leu Ala Ser Gly Val Pro Ser Arg Phe Ser
        515                 520                 525

Gly Ser Gly Ser Gly Thr Asp Tyr Thr Leu Thr Ile Ser Ser Leu Gln
    530                 535                 540

Pro Glu Asp Phe Ala Thr Tyr Tyr Cys Gln Thr Tyr Tyr Gly Gly Gly
545                 550                 555                 560

His Ile Gly Trp Gly Phe Gly Thr Gly Thr Lys Val Thr Val Leu Gly
                565                 570                 575

Gly Gly Gly Gly Ser Gly Gly Gly Gly Ser Gly Gly Gly Gly Ser Gly
            580                 585                 590

Gly Gly Gly Ser Gln Ser Gln Leu Val Glu Ser Gly Gly Gly Arg Val
        595                 600                 605

Gln Pro Gly Gly Ser Leu Arg Leu Ser Cys Ala Ala Ser Gly Phe Ser
    610                 615                 620

Phe Ser Ala Asn Tyr Trp Ile Cys Trp Val Arg Gln Ala Pro Gly Lys
625                 630                 635                 640
```

```
Gly Leu Glu Trp Ile Val Cys Ile Tyr Ile Gly Ser Arg Ala Asp Thr
            645                 650                 655

Tyr Tyr Ala Pro Trp Ala Lys Gly Arg Phe Thr Ile Ser Lys Asp Asn
        660                 665                 670

Ser Lys Asn Thr Val Tyr Leu Gln Met Asn Ser Leu Arg Ala Glu Asp
    675                 680                 685

Thr Ala Thr Tyr Phe Cys Ala Arg Phe Ser Ser Gly Ile Tyr Asp Leu
    690                 695                 700

Asp Arg Phe Phe Leu Trp Gly Gln Gly Thr Gln Val Thr Val Ser Ser
705                 710                 715                 720


<210> SEQ ID NO 39
<211> LENGTH: 216
<212> TYPE: PRT
<213> ORGANISM: Artificial sequence
<220> FEATURE:
<223> OTHER INFORMATION: artificial antibody-related sequence

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gly Ser Ser Tyr Ser Thr Gly
                85                  90                  95

Ser Asn Ile Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215


<210> SEQ ID NO 40
<211> LENGTH: 719
<212> TYPE: PRT
<213> ORGANISM: Artificial sequence
<220> FEATURE:
<223> OTHER INFORMATION: artificial antibody-related sequence

<400> SEQUENCE: 40

Glu Val Gln Leu Val Glu Ser Gly Gly Gly Arg Val Gln Pro Gly Gly
1               5                   10                  15
```

```
Ser Leu Arg Leu Ser Cys Ala Ala Ser Gly Phe Ser Ser Ser Ser Ala
            20                  25                  30

His Tyr Met Cys Trp Val Arg Gln Ala Pro Gly Lys Gly Leu Glu Trp
        35                  40                  45

Ile Gly Cys Ile Tyr Ala Gly Ser Arg Gly Ser Thr Tyr Tyr Ala Ser
    50                  55                  60

Trp Ala Lys Gly Arg Phe Thr Ile Ser Lys Ala Ser Ser Thr Thr Val
65                  70                  75                  80

Tyr Leu Gln Met Asn Ser Leu Arg Ala Glu Asp Thr Ala Thr Tyr Tyr
                85                  90                  95

Cys Ala Arg Ala Ala Phe Val Asn Arg Gly Val Ser Trp Ile Trp Pro
            100                 105                 110

Tyr Tyr Phe Ser Leu Trp Gly Gln Gly Thr Gln Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430
```

```
Cys Ser Val Met His Glu Ala Leu His Asn His Tyr Thr Gln Lys Ser
        435                 440                 445

Leu Ser Leu Ser Leu Gly Gly Gly Gly Gly Ser Gly Gly Gly Gly Ser
    450                 455                 460

Ala Phe Gln Leu Thr Gln Ser Pro Ser Ser Leu Ser Ala Ser Val Gly
465                 470                 475                 480

Asp Arg Val Thr Ile Thr Cys Gln Ala Ser Gln Ser Ile Asp Ser Trp
                485                 490                 495

Leu Ala Trp Tyr Gln Gln Lys Pro Gly Lys Pro Pro Lys Leu Leu Ile
            500                 505                 510

Tyr Gln Ala Ser Lys Leu Ala Ser Gly Val Pro Ser Arg Phe Ser Gly
        515                 520                 525

Ser Gly Ser Gly Thr Asp Tyr Thr Leu Thr Ile Ser Ser Leu Gln Pro
    530                 535                 540

Glu Asp Phe Ala Thr Tyr Tyr Cys Gln Thr Tyr Tyr Gly Gly Gly His
545                 550                 555                 560

Ile Gly Trp Gly Phe Gly Thr Gly Thr Lys Val Thr Val Leu Gly Gly
                565                 570                 575

Gly Gly Gly Ser Gly Gly Gly Gly Ser Gly Gly Gly Gly Ser Gly Gly
            580                 585                 590

Gly Gly Ser Gln Ser Gln Leu Val Glu Ser Gly Gly Gly Arg Val Gln
        595                 600                 605

Pro Gly Gly Ser Leu Arg Leu Ser Cys Ala Ala Ser Gly Phe Ser Phe
    610                 615                 620

Ser Ala Asn Tyr Trp Ile Cys Trp Val Arg Gln Ala Pro Gly Lys Gly
625                 630                 635                 640

Leu Glu Trp Ile Val Cys Ile Tyr Ile Gly Ser Arg Ala Asp Thr Tyr
                645                 650                 655

Tyr Ala Pro Trp Ala Lys Gly Arg Phe Thr Ile Ser Lys Asp Asn Ser
            660                 665                 670

Lys Asn Thr Val Tyr Leu Gln Met Asn Ser Leu Arg Ala Glu Asp Thr
        675                 680                 685

Ala Thr Tyr Phe Cys Ala Arg Phe Ser Ser Gly Ile Tyr Asp Leu Asp
    690                 695                 700

Arg Phe Phe Leu Trp Gly Gln Gly Thr Gln Val Thr Val Ser Ser
705                 710                 715
```

<210> SEQ ID NO 41
<211> LENGTH: 217
<212> TYPE: PRT
<213> ORGANISM: Artificial sequence
<220> FEATURE:
<223> OTHER INFORMATION: artificial antibody-related sequence

<400> SEQUENCE: 41

```
Ala Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asp Ser Trp
            20                  25                  30

Leu Ala Trp Tyr Gln Gln Lys Pro Gly Lys Pro Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80
```

```
Glu Asp Phe Ala Thr Tyr Tyr Cys Gln Thr Tyr Tyr Gly Gly Gly His
                85                  90                  95

Ile Gly Trp Gly Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 42
<211> LENGTH: 719
<212> TYPE: PRT
<213> ORGANISM: Artificial sequence
<220> FEATURE:
<223> OTHER INFORMATION: artificial antibody-related sequence

<400> SEQUENCE: 42

Gln Ser Gln Leu Val Glu Ser Gly Gly Gly Arg Val Gln Pro Gly Gly
1               5                   10                  15

Ser Leu Arg Leu Ser Cys Ala Ala Ser Gly Phe Ser Phe Ser Ala Asn
            20                  25                  30

Tyr Trp Ile Cys Trp Val Arg Gln Ala Pro Gly Lys Gly Leu Glu Trp
        35                  40                  45

Ile Val Cys Ile Tyr Ile Gly Ser Arg Ala Asp Thr Tyr Tyr Ala Pro
    50                  55                  60

Trp Ala Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Thr Tyr
                85                  90                  95

Phe Cys Ala Arg Phe Ser Ser Gly Ile Tyr Asp Leu Asp Arg Phe Phe
            100                 105                 110

Leu Trp Gly Gln Gly Thr Gln Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220
```

```
Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
        435                 440                 445

Leu Gly Gly Gly Gly Gly Ser Gly Gly Gly Gly Ser Asp Ile Gln Met
    450                 455                 460

Thr Gln Ser Pro Ser Ser Leu Ser Ala Arg Val Gly Asp Arg Val Thr
465                 470                 475                 480

Ile Thr Cys Gln Ala Ser Glu Asp Ile Glu Ser Tyr Leu Ala Trp Tyr
                485                 490                 495

Gln Gln Lys Pro Gly Lys Ala Pro Lys Leu Leu Ile Tyr Arg Ala Ser
            500                 505                 510

Thr Leu Ala Tyr Gly Val Pro Ser Arg Phe Ser Gly Ser Gly Ser Gly
        515                 520                 525

Arg Asp Phe Thr Leu Thr Ile Ser Ser Leu Gln Pro Glu Asp Phe Ala
    530                 535                 540

Thr Tyr Tyr Cys Leu Gly Ser Ser Tyr Ser Thr Gly Ser Asn Ile Phe
545                 550                 555                 560

Gly Thr Gly Thr Lys Val Thr Val Leu Gly Gly Gly Gly Ser Gly
                565                 570                 575

Gly Gly Gly Ser Gly Gly Gly Gly Ser Gly Gly Gly Gly Ser Glu Val
            580                 585                 590

Gln Leu Val Glu Ser Gly Gly Gly Leu Val Gln Pro Gly Gly Ser Leu
        595                 600                 605

Arg Leu Ser Cys Ala Ala Ser Gly Phe Ser Ser Ser Ser Ala His Tyr
    610                 615                 620

Met Cys Trp Val Arg Gln Ala Pro Gly Lys Gly Leu Glu Trp Ile Gly
625                 630                 635                 640

Cys Ile Tyr Ala Gly Ser Arg Gly Ser Thr Tyr Tyr Ala Ser Trp Ala
```

```
                645                 650                 655

Lys Gly Arg Phe Thr Ile Ser Arg Asp Asn Ser Lys Asn Thr Val Tyr
            660                 665                 670

Leu Gln Met Asn Ser Leu Arg Ala Glu Asp Thr Ala Val Tyr Tyr Cys
        675                 680                 685

Ala Arg Ala Ala Phe Val Asn Arg Gly Val Ser Trp Ile Trp Pro Tyr
    690                 695                 700

Tyr Phe Ser Leu Trp Gly Gln Gly Thr Leu Val Thr Val Ser Ser
705                 710                 715


<210> SEQ ID NO 43
<211> LENGTH: 217
<212> TYPE: PRT
<213> ORGANISM: Artificial sequence
<220> FEATURE:
<223> OTHER INFORMATION: artificial antibody-related sequence

<400> SEQUENCE: 43

Ala Phe Gln Leu Thr Gln Ser Pro Ser Ser Leu Ser Ala Ser Val Gly
1               5                   10                  15

Asp Arg Val Thr Ile Thr Cys Gln Ala Ser Gln Ser Ile Asp Ser Trp
            20                  25                  30

Leu Ala Trp Tyr Gln Gln Lys Pro Gly Lys Pro Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln Thr Tyr Tyr Gly Gly Gly His
                85                  90                  95

Ile Gly Trp Gly Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160

Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 44
<211> LENGTH: 718
<212> TYPE: PRT
<213> ORGANISM: Artificial sequence
<220> FEATURE:
<223> OTHER INFORMATION: artificial antibody-related sequence

<400> SEQUENCE: 44

Gln Ser Gln Leu Val Glu Ser Gly Gly Gly Arg Val Gln Pro Gly Gly
1               5                   10                  15
```

```
Ser Leu Arg Leu Ser Cys Ala Ala Ser Gly Phe Ser Phe Ser Ala Asn
            20                  25                  30

Tyr Trp Ile Cys Trp Val Arg Gln Ala Pro Gly Lys Gly Leu Glu Trp
        35                  40                  45

Ile Val Cys Ile Tyr Ile Gly Ser Arg Ala Asp Thr Tyr Tyr Ala Pro
    50                  55                  60

Trp Ala Lys Gly Arg Phe Thr Ile Ser Lys Asp Asn Ser Lys Asn Thr
65                  70                  75                  80

Val Tyr Leu Gln Met Asn Ser Leu Arg Ala Glu Asp Thr Ala Thr Tyr
                85                  90                  95

Phe Cys Ala Arg Phe Ser Ser Gly Ile Tyr Asp Leu Asp Arg Phe Phe
            100                 105                 110

Leu Trp Gly Gln Gly Thr Gln Val Thr Val Ser Ser Ala Ser Thr Lys
        115                 120                 125

Gly Pro Ser Val Phe Pro Leu Ala Pro Cys Ser Arg Ser Thr Ser Glu
    130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Lys Thr Tyr Thr Cys Asn
        195                 200                 205

Val Asp His Lys Pro Ser Asn Thr Lys Val Asp Lys Arg Val Glu Ser
    210                 215                 220

Lys Tyr Gly Pro Pro Cys Pro Pro Cys Pro Ala Pro Glu Phe Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser Gln
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Gly Leu Pro Ser Ser Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Gln Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Arg Leu Thr Val
                405                 410                 415

Asp Lys Ser Arg Trp Gln Glu Gly Asn Val Phe Ser Cys Ser Val Met
            420                 425                 430

His Glu Ala Leu His Asn His Tyr Thr Gln Lys Ser Leu Ser Leu Ser
```

```
        435                 440                 445

Leu Gly Gly Gly Gly Gly Ser Gly Gly Gly Gly Ser Asp Ile Gln Met
    450                 455                 460

Thr Gln Ser Pro Ser Ser Leu Ser Ala Ser Val Gly Asp Arg Val Thr
465                 470                 475                 480

Ile Thr Cys Gln Ala Ser Glu Asp Ile Glu Ser Tyr Leu Ala Trp Tyr
                485                 490                 495

Gln Gln Lys Pro Gly Lys Ala Pro Lys Leu Leu Ile Tyr Arg Ala Ser
            500                 505                 510

Thr Leu Ala Tyr Gly Val Pro Ser Arg Phe Ser Gly Ser Gly Ser Gly
        515                 520                 525

Thr Asp Phe Thr Leu Thr Ile Ser Ser Leu Gln Pro Glu Asp Phe Ala
    530                 535                 540

Thr Tyr Tyr Cys Leu Gly Ser Ser Tyr Ser Thr Gly Ser Asn Ile Phe
545                 550                 555                 560

Gly Thr Gly Thr Lys Val Thr Val Leu Gly Gly Gly Gly Gly Ser Gly
                565                 570                 575

Gly Gly Gly Ser Gly Gly Gly Gly Ser Gly Gly Gly Gly Ser Glu Val
            580                 585                 590

Gln Leu Val Glu Ser Gly Gly Gly Arg Val Gln Pro Gly Gly Ser Leu
        595                 600                 605

Arg Leu Ser Cys Ala Ala Ser Gly Phe Ser Ser Ser Ser Ala His Tyr
    610                 615                 620

Met Cys Trp Val Arg Gln Ala Pro Gly Lys Gly Leu Glu Trp Ile Gly
625                 630                 635                 640

Cys Ile Tyr Ala Gly Ser Arg Gly Ser Thr Tyr Tyr Ala Ser Trp Ala
                645                 650                 655

Lys Gly Arg Phe Thr Ile Ser Lys Ala Ser Ser Thr Thr Val Tyr Leu
            660                 665                 670

Gln Met Asn Ser Leu Arg Ala Glu Asp Thr Ala Thr Tyr Tyr Cys Ala
        675                 680                 685

Arg Ala Ala Phe Val Asn Arg Gly Val Ser Trp Ile Trp Pro Tyr Tyr
    690                 695                 700

Phe Ser Leu Trp Gly Gln Gly Thr Gln Val Thr Val Ser Ser
705                 710                 715


<210> SEQ ID NO 45
<211> LENGTH: 481
<212> TYPE: PRT
<213> ORGANISM: Artificial sequence
<220> FEATURE:
<223> OTHER INFORMATION: artificial antibody-related sequence

<400> SEQUENCE: 45

Asp Ile Gln Met Thr Gln Ser Pro Ser Ser Leu Ser Ala Arg Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Tyr Gly Val Pro Ser Arg Phe Ser Gly
    50                  55                  60

Ser Gly Ser Gly Arg Asp Phe Thr Leu Thr Ile Ser Ser Leu Gln Pro
65                  70                  75                  80

Glu Asp Phe Ala Thr Tyr Tyr Cys Leu Gly Ser Ser Tyr Ser Thr Gly
```

```
                85                  90                  95

Ser Asn Ile Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Gly Gly Ser Gly Gly Gly
    210                 215                 220

Gly Ser Ala Phe Gln Leu Thr Gln Ser Pro Ser Ser Leu Ser Ala Ser
225                 230                 235                 240

Val Gly Asp Arg Val Thr Ile Thr Cys Gln Ala Ser Gln Ser Ile Asp
                245                 250                 255

Ser Trp Leu Ala Trp Tyr Gln Gln Lys Pro Gly Lys Pro Pro Lys Leu
            260                 265                 270

Leu Ile Tyr Gln Ala Ser Lys Leu Ala Ser Gly Val Pro Ser Arg Phe
        275                 280                 285

Ser Gly Ser Gly Ser Gly Thr Asp Tyr Thr Leu Thr Ile Ser Ser Leu
    290                 295                 300

Gln Pro Glu Asp Phe Ala Thr Tyr Tyr Cys Gln Thr Tyr Tyr Gly Gly
305                 310                 315                 320

Gly His Ile Gly Trp Gly Phe Gly Thr Gly Thr Lys Val Thr Val Leu
                325                 330                 335

Gly Gly Gly Gly Gly Ser Gly Gly Gly Gly Ser Gly Gly Gly Gly Ser
            340                 345                 350

Gly Gly Gly Gly Ser Gln Ser Gln Leu Val Glu Ser Gly Gly Gly Arg
        355                 360                 365

Val Gln Pro Gly Gly Ser Leu Arg Leu Ser Cys Ala Ala Ser Gly Phe
    370                 375                 380

Ser Phe Ser Ala Asn Tyr Trp Ile Cys Trp Val Arg Gln Ala Pro Gly
385                 390                 395                 400

Lys Gly Leu Glu Trp Ile Val Cys Ile Tyr Ile Gly Ser Arg Ala Asp
                405                 410                 415

Thr Tyr Tyr Ala Pro Trp Ala Lys Gly Arg Phe Thr Ile Ser Lys Asp
            420                 425                 430

Asn Ser Lys Asn Thr Val Tyr Leu Gln Met Asn Ser Leu Arg Ala Glu
        435                 440                 445

Asp Thr Ala Thr Tyr Phe Cys Ala Arg Phe Ser Ser Gly Ile Tyr Asp
    450                 455                 460

Leu Asp Arg Phe Phe Leu Trp Gly Gln Gly Thr Gln Val Thr Val Ser
465                 470                 475                 480

Ser


<210> SEQ ID NO 46
<211> LENGTH: 455
```

<212> TYPE: PRT
<213> ORGANISM: Artificial sequence
<220> FEATURE:
<223> OTHER INFORMATION: artificial antibody-related sequence

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ser Ser Ser Ala
            20                  25                  30

His Tyr Met Cys Trp Val Arg Gln Ala Pro Gly Lys Gly Leu Glu Trp
        35                  40                  45

Ile Gly Cys Ile Tyr Ala Gly Ser Arg Gly Ser Thr Tyr Tyr Ala Ser
    50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ala Ala Phe Val Asn Arg Gly Val Ser Trp Ile Trp
            100                 105                 110

Pro Tyr Tyr Phe Ser Leu Trp Gly Gln Gly Thr Leu Val Thr Val Ser
        115                 120                 125

Ser Ala Ser Thr Lys Gly Pro Ser Val Phe Pro Leu Ala Pro Cys Ser
    130                 135                 140

Arg Ser Thr Ser Glu Ser Thr Ala Ala Leu Gly Cys Leu Val Lys Asp
145                 150                 155                 160

Tyr Phe Pro Glu Pro Val Thr Val Ser Trp Asn Ser Gly Ala Leu Thr
                165                 170                 175

Ser Gly Val His Thr Phe Pro Ala Val Leu Gln Ser Ser Gly Leu Tyr
            180                 185                 190

Ser Leu Ser Ser Val Val Thr Val Pro Ser Ser Ser Leu Gly Thr Lys
        195                 200                 205

Thr Tyr Thr Cys Asn Val Asp His Lys Pro Ser Asn Thr Lys Val Asp
    210                 215                 220

Lys Arg Val Glu Ser Lys Tyr Gly Pro Pro Cys Pro Pro Cys Pro Ala
225                 230                 235                 240

Pro Glu Phe Leu Gly Gly Pro Ser Val Phe Leu Phe Pro Pro Lys Pro
                245                 250                 255

Lys Asp Thr Leu Met Ile Ser Arg Thr Pro Glu Val Thr Cys Val Val
            260                 265                 270

Val Asp Val Ser Gln Glu Asp Pro Glu Val Gln Phe Asn Trp Tyr Val
        275                 280                 285

Asp Gly Val Glu Val His Asn Ala Lys Thr Lys Pro Arg Glu Glu Gln
    290                 295                 300

Phe Asn Ser Thr Tyr Arg Val Val Ser Val Leu Thr Val Leu His Gln
305                 310                 315                 320

Asp Trp Leu Asn Gly Lys Glu Tyr Lys Cys Lys Val Ser Asn Lys Gly
                325                 330                 335

Leu Pro Ser Ser Ile Glu Lys Thr Ile Ser Lys Ala Lys Gly Gln Pro
            340                 345                 350

Arg Glu Pro Gln Val Tyr Thr Leu Pro Pro Ser Gln Glu Glu Met Thr
        355                 360                 365

Lys Asn Gln Val Ser Leu Thr Cys Leu Val Lys Gly Phe Tyr Pro Ser
    370                 375                 380
```

```
Asp Ile Ala Val Glu Trp Glu Ser Asn Gly Gln Pro Glu Asn Asn Tyr
385                 390                 395                 400

Lys Thr Thr Pro Pro Val Leu Asp Ser Asp Gly Ser Phe Phe Leu Tyr
                405                 410                 415

Ser Arg Leu Thr Val Asp Lys Ser Arg Trp Gln Glu Gly Asn Val Phe
            420                 425                 430

Ser Cys Ser Val Met His Glu Ala Leu His Asn His Tyr Thr Gln Lys
        435                 440                 445

Ser Leu Ser Leu Ser Leu Gly
    450                 455


<210> SEQ ID NO 47
<211> LENGTH: 481
<212> TYPE: PRT
<213> ORGANISM: Artificial sequence
<220> FEATURE:
<223> OTHER INFORMATION: artificial antibody-related sequence

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Tyr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gly Ser Ser Tyr Ser Thr Gly
                85                  90                  95

Ser Asn Ile Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Gly Gly Ser Gly Gly Gly
    210                 215                 220

Gly Ser Ala Phe Gln Leu Thr Gln Ser Pro Ser Ser Leu Ser Ala Ser
225                 230                 235                 240

Val Gly Asp Arg Val Thr Ile Thr Cys Gln Ala Ser Gln Ser Ile Asp
                245                 250                 255

Ser Trp Leu Ala Trp Tyr Gln Gln Lys Pro Gly Lys Pro Pro Lys Leu
            260                 265                 270

Leu Ile Tyr Gln Ala Ser Lys Leu Ala Ser Gly Val Pro Ser Arg Phe
        275                 280                 285
```

```
Ser Gly Ser Gly Ser Gly Thr Asp Tyr Thr Leu Thr Ile Ser Ser Leu
    290                 295                 300

Gln Pro Glu Asp Phe Ala Thr Tyr Tyr Cys Gln Thr Tyr Tyr Gly Gly
305                 310                 315                 320

Gly His Ile Gly Trp Gly Phe Gly Thr Gly Thr Lys Val Thr Val Leu
                325                 330                 335

Gly Gly Gly Gly Gly Ser Gly Gly Gly Gly Ser Gly Gly Gly Gly Ser
            340                 345                 350

Gly Gly Gly Gly Ser Gln Ser Gln Leu Val Glu Ser Gly Gly Gly Arg
        355                 360                 365

Val Gln Pro Gly Gly Ser Leu Arg Leu Ser Cys Ala Ala Ser Gly Phe
    370                 375                 380

Ser Phe Ser Ala Asn Tyr Trp Ile Cys Trp Val Arg Gln Ala Pro Gly
385                 390                 395                 400

Lys Gly Leu Glu Trp Ile Val Cys Ile Tyr Ile Gly Ser Arg Ala Asp
                405                 410                 415

Thr Tyr Tyr Ala Pro Trp Ala Lys Gly Arg Phe Thr Ile Ser Lys Asp
            420                 425                 430

Asn Ser Lys Asn Thr Val Tyr Leu Gln Met Asn Ser Leu Arg Ala Glu
        435                 440                 445

Asp Thr Ala Thr Tyr Phe Cys Ala Arg Phe Ser Ser Gly Ile Tyr Asp
    450                 455                 460

Leu Asp Arg Phe Phe Leu Trp Gly Gln Gly Thr Gln Val Thr Val Ser
465                 470                 475                 480

Ser


<210> SEQ ID NO 48
<211> LENGTH: 454
<212> TYPE: PRT
<213> ORGANISM: Artificial sequence
<220> FEATURE:
<223> OTHER INFORMATION: artificial antibody-related sequence

<400> SEQUENCE: 48

Glu Val Gln Leu Val Glu Ser Gly Gly Gly Arg Val Gln Pro Gly Gly
1               5                   10                  15

Ser Leu Arg Leu Ser Cys Ala Ala Ser Gly Phe Ser Ser Ser Ser Ala
            20                  25                  30

His Tyr Met Cys Trp Val Arg Gln Ala Pro Gly Lys Gly Leu Glu Trp
        35                  40                  45

Ile Gly Cys Ile Tyr Ala Gly Ser Arg Gly Ser Thr Tyr Tyr Ala Ser
    50                  55                  60

Trp Ala Lys Gly Arg Phe Thr Ile Ser Lys Ala Ser Ser Thr Thr Val
65                  70                  75                  80

Tyr Leu Gln Met Asn Ser Leu Arg Ala Glu Asp Thr Ala Thr Tyr Tyr
                85                  90                  95

Cys Ala Arg Ala Ala Phe Val Asn Arg Gly Val Ser Trp Ile Trp Pro
            100                 105                 110

Tyr Tyr Phe Ser Leu Trp Gly Gln Gly Thr Gln Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
```

```
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365

Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly
    450


<210> SEQ ID NO 49
<211> LENGTH: 481
<212> TYPE: PRT
<213> ORGANISM: Artificial sequence
<220> FEATURE:
<223> OTHER INFORMATION: artificial antibody-related sequence

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Tyr Gly Val Pro Ser Arg Phe Ser Gly
    50                  55                  60

Ser Gly Ser Gly Thr Asp Phe Thr Leu Thr Ile Ser Ser Leu Gln Pro
```

```
65                  70                  75                  80

Glu Asp Phe Ala Thr Tyr Tyr Cys Leu Gly Ser Ser Tyr Ser Thr Gly
                85                  90                  95

Ser Asn Ile Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Gly Gly Gly Gly Ser Gly Gly Gly
    210                 215                 220

Gly Ser Ala Phe Gln Leu Thr Gln Ser Pro Ser Ser Leu Ser Ala Ser
225                 230                 235                 240

Val Gly Asp Arg Val Thr Ile Thr Cys Gln Ala Ser Gln Ser Ile Asp
                245                 250                 255

Ser Trp Leu Ala Trp Tyr Gln Gln Lys Pro Gly Lys Pro Pro Lys Leu
            260                 265                 270

Leu Ile Tyr Gln Ala Ser Lys Leu Ala Ser Gly Val Pro Ser Arg Phe
        275                 280                 285

Ser Gly Ser Gly Ser Gly Thr Asp Tyr Thr Leu Thr Ile Ser Ser Leu
    290                 295                 300

Gln Pro Glu Asp Phe Ala Thr Tyr Tyr Cys Gln Thr Tyr Tyr Gly Gly
305                 310                 315                 320

Gly His Ile Gly Trp Gly Phe Gly Thr Gly Thr Lys Val Thr Val Leu
                325                 330                 335

Gly Gly Gly Gly Gly Ser Gly Gly Gly Gly Ser Gly Gly Gly Gly Ser
            340                 345                 350

Gly Gly Gly Gly Ser Gln Ser Gln Leu Val Glu Ser Gly Gly Gly Arg
        355                 360                 365

Val Gln Pro Gly Gly Ser Leu Arg Leu Ser Cys Ala Ala Ser Gly Phe
    370                 375                 380

Ser Phe Ser Ala Asn Tyr Trp Ile Cys Trp Val Arg Gln Ala Pro Gly
385                 390                 395                 400

Lys Gly Leu Glu Trp Ile Val Cys Ile Tyr Ile Gly Ser Arg Ala Asp
                405                 410                 415

Thr Tyr Tyr Ala Pro Trp Ala Lys Gly Arg Phe Thr Ile Ser Lys Asp
            420                 425                 430

Asn Ser Lys Asn Thr Val Tyr Leu Gln Met Asn Ser Leu Arg Ala Glu
        435                 440                 445

Asp Thr Ala Thr Tyr Phe Cys Ala Arg Phe Ser Ser Gly Ile Tyr Asp
    450                 455                 460

Leu Asp Arg Phe Phe Leu Trp Gly Gln Gly Thr Gln Val Thr Val Ser
465                 470                 475                 480

Ser
```

<210> SEQ ID NO 50
<211> LENGTH: 454
<212> TYPE: PRT
<213> ORGANISM: Artificial sequence
<220> FEATURE:
<223> OTHER INFORMATION: artificial antibody-related sequence

<400> SEQUENCE: 50

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Ser Ser Ser Ala
            20                  25                  30

His Tyr Met Cys Trp Val Arg Gln Ala Pro Gly Lys Gly Leu Glu Trp
        35                  40                  45

Ile Gly Cys Ile Tyr Ala Gly Ser Arg Gly Ser Thr Tyr Tyr Ala Ser
    50                  55                  60

Trp Ala Lys Gly Arg Phe Thr Ile Ser Lys Ala Ser Ser Thr Thr Val
65                  70                  75                  80

Tyr Leu Gln Met Asn Ser Leu Arg Ala Glu Asp Thr Ala Val Tyr Tyr
                85                  90                  95

Cys Ala Arg Ala Ala Phe Val Asn Arg Gly Val Ser Trp Ile Trp Pro
            100                 105                 110

Tyr Tyr Phe Ser Leu Trp Gly Gln Gly Thr Leu Val Thr Val Ser Ser
        115                 120                 125

Ala Ser Thr Lys Gly Pro Ser Val Phe Pro Leu Ala Pro Cys Ser Arg
    130                 135                 140

Ser Thr Ser Glu Ser Thr Ala Ala Leu Gly Cys Leu Val Lys Asp Tyr
145                 150                 155                 160

Phe Pro Glu Pro Val Thr Val Ser Trp Asn Ser Gly Ala Leu Thr Ser
                165                 170                 175

Gly Val His Thr Phe Pro Ala Val Leu Gln Ser Ser Gly Leu Tyr Ser
            180                 185                 190

Leu Ser Ser Val Val Thr Val Pro Ser Ser Ser Leu Gly Thr Lys Thr
        195                 200                 205

Tyr Thr Cys Asn Val Asp His Lys Pro Ser Asn Thr Lys Val Asp Lys
    210                 215                 220

Arg Val Glu Ser Lys Tyr Gly Pro Pro Cys Pro Pro Cys Pro Ala Pro
225                 230                 235                 240

Glu Phe Leu Gly Gly Pro Ser Val Phe Leu Phe Pro Pro Lys Pro Lys
                245                 250                 255

Asp Thr Leu Met Ile Ser Arg Thr Pro Glu Val Thr Cys Val Val Val
            260                 265                 270

Asp Val Ser Gln Glu Asp Pro Glu Val Gln Phe Asn Trp Tyr Val Asp
        275                 280                 285

Gly Val Glu Val His Asn Ala Lys Thr Lys Pro Arg Glu Glu Gln Phe
    290                 295                 300

Asn Ser Thr Tyr Arg Val Val Ser Val Leu Thr Val Leu His Gln Asp
305                 310                 315                 320

Trp Leu Asn Gly Lys Glu Tyr Lys Cys Lys Val Ser Asn Lys Gly Leu
                325                 330                 335

Pro Ser Ser Ile Glu Lys Thr Ile Ser Lys Ala Lys Gly Gln Pro Arg
            340                 345                 350

Glu Pro Gln Val Tyr Thr Leu Pro Pro Ser Gln Glu Glu Met Thr Lys
        355                 360                 365
```

-continued

```
Asn Gln Val Ser Leu Thr Cys Leu Val Lys Gly Phe Tyr Pro Ser Asp
    370                 375                 380

Ile Ala Val Glu Trp Glu Ser Asn Gly Gln Pro Glu Asn Asn Tyr Lys
385                 390                 395                 400

Thr Thr Pro Pro Val Leu Asp Ser Asp Gly Ser Phe Phe Leu Tyr Ser
                405                 410                 415

Arg Leu Thr Val Asp Lys Ser Arg Trp Gln Glu Gly Asn Val Phe Ser
            420                 425                 430

Cys Ser Val Met His Glu Ala Leu His Asn His Tyr Thr Gln Lys Ser
        435                 440                 445

Leu Ser Leu Ser Leu Gly
    450
```